United States Patent
Bukshpan et al.

(10) Patent No.: US 7,354,733 B2
(45) Date of Patent: Apr. 8, 2008

(54) METHOD FOR SORTING AND SEPARATING LIVING CELLS

(75) Inventors: Shmuel Bukshpan, Ramat Hasharon (IL); Gleb Zilberstein, Rehovot (IL)

(73) Assignee: Cellect Technologies Corp., Tortola (VG)

( * ) Notice: Subject to any disclaimer, the term of this patent is extended or adjusted under 35 U.S.C. 154(b) by 520 days.

(21) Appl. No.: 10/105,628

(22) Filed: Mar. 26, 2002

(65) Prior Publication Data

US 2002/0198928 A1   Dec. 26, 2002

Related U.S. Application Data

(60) Provisional application No. 60/279,447, filed on Mar. 29, 2001.

(51) Int. Cl.
*C12Q 1/28* (2006.01)

(52) U.S. Cl. .................. 435/28; 435/7.2; 435/7.72; 435/7.9; 435/7.91; 435/7.92; 435/21; 435/23; 435/24; 435/29; 435/30; 435/168; 435/173.2; 435/173.4; 435/173.9; 435/174; 435/176; 435/177; 435/178; 435/192; 435/194; 435/207; 435/380; 435/308.1; 435/960; 435/968; 436/519; 436/525; 436/528; 436/529; 436/539; 436/63; 436/73; 436/80; 436/182; 436/801; 436/905; 210/702; 210/719; 210/721; 210/723; 210/748; 210/757; 210/758; 356/36; 356/38; 356/311; 356/317; 356/348; 356/349; 216/24; 216/84; 216/85; 216/87; 216/100; 427/2.11; 427/2.13; 427/581; 427/595; 427/123; 427/125; 427/126.1; 427/126.3; 427/126.5; 427/283; 427/352; 427/404; 427/419.1; 427/443.1; 430/8; 430/16; 430/264; 430/464; 250/462.1

(58) Field of Classification Search ............ 435/4–7.4, 435/7.92, 34, 173.1, 173.9, 174–182, 283.1, 435/287.1, 287.2, 287.7, 814, 7.72, 7.9, 7.91, 435/21, 23, 24, 28, 29, 30, 40.5, 40.51, 40.52, 435/168, 173.2, 173.4, 192, 194, 207, 347, 435/380, 402, 308.1, 817, 960, 968, 7.2; 436/518–535, 543–544, 546, 73, 80, 161, 436/539, 63, 182, 801, 905, 806; 210/656, 210/601, 632, 695, 702, 719, 721, 723, 729, 210/748, 757, 758, 759, 222; 356/450, 457, 356/36, 38, 311, 317, 337, 443, 444, 908, 356/931, 934, 947, 948, 949; 216/24–26, 216/85, 94, 100, 22, 54, 84, 87, 97; 430/199, 430/202, 217, 230, 249, 264, 8, 16, 464, 430/477, 492; 250/283, 284, 462.1; 427/2.11, 427/2.13, 487, 547, 550, 581, 595, 596, 597, 427/598, 123, 125, 126.1, 126.3, 126.5, 128, 427/132, 165, 169, 283, 287, 352, 404, 419.1, 427/439, 443.1; 106/1.05, 1.11, 1.18, 1.19, 106/1.26; 205/163, 167, 794; 438/1, 678; 209/45, 46, 47

See application file for complete search history.

(56) References Cited

U.S. PATENT DOCUMENTS

| | | | | |
|---|---|---|---|---|
| 2,289,367 A | * | 7/1942 | Kendall | 430/480 |
| 2,666,355 A | * | 1/1954 | Trurnit | 356/36 |
| 3,515,551 A | * | 6/1970 | Audran et al. | 430/270.1 |
| 3,600,182 A | * | 8/1971 | Matejec et al. | 430/642 |
| 3,684,511 A | * | 8/1972 | Weyde et al. | 430/290 |
| 3,689,391 A | * | 9/1972 | Ullman | 204/157.91 |
| 3,694,207 A | * | 9/1972 | Matejec et al. | 430/290 |
| 3,710,933 A | * | 1/1973 | Fulwyler et al. | 209/3.1 |
| 3,720,622 A | * | 3/1973 | Bollyky | 252/700 |
| 3,776,730 A | * | 12/1973 | Matejec et al. | 430/290 |
| 3,905,767 A | * | 9/1975 | Morris et al. | 436/515 |
| 4,054,646 A | * | 10/1977 | Giaever | 435/5 |
| 4,084,902 A | * | 4/1978 | Green | 356/38 |
| 4,084,967 A | * | 4/1978 | O'Brien | 430/202 |
| 4,097,278 A | * | 6/1978 | Bissonette | 430/223 |
| 4,103,073 A | * | 7/1978 | McAlear et al. | 428/478.2 |
| 4,135,976 A | * | 1/1979 | Kitajima | 75/713 |
| 4,188,538 A | * | 2/1980 | Diels | 250/423 P |
| 4,258,001 A | * | 3/1981 | Pierce et al. | 422/56 |
| 4,313,734 A | * | 2/1982 | Leuvering | 436/525 |

| | | | | | | | | |
|---|---|---|---|---|---|---|---|---|
| 4,315,998 | A | * | 2/1982 | Neckers et al. ............ 525/359.3 | 5,439,829 | A | * | 8/1995 | Anderson et al. ............ 436/518 |
| 4,331,444 | A | * | 5/1982 | Mihara et al. .............. 436/539 | 5,445,944 | A | * | 8/1995 | Ullman ....................... 435/28 |
| 4,337,063 | A | * | 6/1982 | Mihara et al. .............. 436/536 | 5,466,575 | A | * | 11/1995 | Cozzette et al. ............... 435/6 |
| 4,337,065 | A | * | 6/1982 | Hiratsuka et al. ............ 436/543 | 5,470,739 | A | * | 11/1995 | Akaike et al. .............. 435/402 |
| 4,356,256 | A | * | 10/1982 | O'Brien et al. .............. 430/332 | 5,476,796 | A | * | 12/1995 | Takahashi et al. .......... 436/526 |
| 4,385,119 | A | * | 5/1983 | Blakemore .................. 435/168 | 5,491,098 | A | * | 2/1996 | Noppe et al. ................ 436/525 |
| 4,404,289 | A | * | 9/1983 | Masuda et al. .............. 436/538 | 5,516,636 | A | * | 5/1996 | McCapra ....................... 435/6 |
| 4,405,711 | A | * | 9/1983 | Masuda et al. ................ 435/4 | 5,521,289 | A | * | 5/1996 | Hainfeld et al. .......... 530/391.5 |
| 4,414,323 | A | * | 11/1983 | Masuda ....................... 435/7.4 | 5,527,731 | A | * | 6/1996 | Yamamoto et al. ...... 250/492.3 |
| 4,414,325 | A | * | 11/1983 | Masuda et al. ................ 435/7.4 | 5,532,138 | A | * | 7/1996 | Singh et al. .............. 435/7.93 |
| 4,416,998 | A | * | 11/1983 | Adams et al. ................ 436/86 | 5,536,644 | A | * | 7/1996 | Ullman et al. .............. 435/7.25 |
| 4,420,558 | A | * | 12/1983 | De Mey et al. .......... 435/7.24 | 5,536,834 | A | * | 7/1996 | Singh et al. ................... 544/98 |
| 4,429,050 | A | * | 1/1984 | Yasuda et al. .............. 436/538 | 5,567,585 | A | * | 10/1996 | Caetano-Anolles et al. ..... 435/6 |
| 4,434,234 | A | * | 2/1984 | Adams et al. ................ 436/86 | 5,578,498 | A | * | 11/1996 | Singh et al. ................ 436/518 |
| 4,472,498 | A | * | 9/1984 | Masuda et al. .............. 435/7.7 | 5,593,814 | A | * | 1/1997 | Matsuda et al. ............ 430/320 |
| 4,473,652 | A | * | 9/1984 | Okazaki et al. .............. 436/536 | 5,595,878 | A | * | 1/1997 | Sood et al. ................... 435/6 |
| 4,478,817 | A | * | 10/1984 | Campbell et al. .............. 435/6 | 5,602,029 | A | * | 2/1997 | Miyamoto ................ 435/395 |
| 4,508,625 | A | * | 4/1985 | Graham ..................... 210/695 | 5,608,519 | A | * | 3/1997 | Gourley et al. ............. 356/318 |
| 4,508,820 | A | * | 4/1985 | Merril et al. .................. 435/29 | 5,616,719 | A | * | 4/1997 | Davalian et al. ............. 546/334 |
| 4,521,522 | A | * | 6/1985 | Lundstrom et al. ......... 436/525 | 5,618,732 | A | * | 4/1997 | Pease et al. .................... 436/8 |
| 4,582,808 | A | * | 4/1986 | Oosawa et al. ............... 436/86 | 5,637,508 | A | * | 6/1997 | Kidwell et al. ............. 436/525 |
| 4,621,063 | A | * | 11/1986 | Wyatt et al. ................. 436/501 | 5,672,478 | A | * | 9/1997 | Singh et al. ................... 435/6 |
| 4,634,628 | A | * | 1/1987 | Munakata et al. ........... 430/325 | 5,674,755 | A | * | 10/1997 | Noppe et al. ............. 436/525 |
| 4,657,646 | A | * | 4/1987 | Greenbaum ............. 204/157.5 | 5,681,755 | A | * | 10/1997 | Noppe et al. ............. 436/525 |
| 4,659,655 | A | * | 4/1987 | Rose ....................... 435/7.21 | 5,705,622 | A | * | 1/1998 | McCapra .................. 536/23.1 |
| 4,661,451 | A | * | 4/1987 | Hansen ....................... 435/174 | 5,709,994 | A | * | 1/1998 | Pease et al. .................... 435/4 |
| 4,666,862 | A |   | 5/1987 | Chan | 5,714,757 | A | * | 2/1998 | Itabashi et al. .............. 250/309 |
| 4,677,067 | A | * | 6/1987 | Schwartz et al. ............ 435/177 | 5,721,131 | A | * | 2/1998 | Rudolph et al. ............. 435/395 |
| 4,687,736 | A | * | 8/1987 | Newman et al. ................ 435/6 | 5,728,590 | A | * | 3/1998 | Powell ....................... 436/547 |
| 4,690,901 | A | * | 9/1987 | Giammara et al. .............. 435/6 | 5,752,606 | A | * | 5/1998 | Wilson et al. .................. 209/2 |
| 4,698,302 | A | * | 10/1987 | Whitehead et al. ........... 435/94 | 5,770,388 | A | * | 6/1998 | Vorpahl .................... 435/7.25 |
| 4,713,324 | A |   | 12/1987 | Fox et al. | 5,780,646 | A | * | 7/1998 | Singh et al. ................... 549/14 |
| 4,728,591 | A | * | 3/1988 | Clark et al. .................... 430/5 | 5,793,485 | A | * | 8/1998 | Gourley ..................... 356/318 |
| 4,732,736 | A | * | 3/1988 | Kobayashi et al. ........... 422/56 | 5,807,675 | A | * | 9/1998 | Davalian et al. ............... 435/6 |
| 4,734,375 | A | * | 3/1988 | Charlton ....................... 436/74 | 5,811,311 | A | * | 9/1998 | Singh et al. ................ 436/518 |
| 4,746,607 | A | * | 5/1988 | Mura et al. .................... 435/25 | 5,817,526 | A | * | 10/1998 | Kinoshita et al. ............ 436/526 |
| 4,777,145 | A | * | 10/1988 | Luotola et al. ................ 436/526 | 5,837,454 | A | * | 11/1998 | Cozzette et al. ................ 435/6 |
| 4,802,951 | A | * | 2/1989 | Clark et al. .................... 216/56 | 5,843,644 | A | * | 12/1998 | Liotta et al. .................... 435/6 |
| 4,853,186 | A | * | 8/1989 | Mura et al. .................... 422/55 | 5,843,657 | A | * | 12/1998 | Liotta et al. .................... 435/6 |
| 4,857,271 | A | * | 8/1989 | Belly et al. .................... 422/55 | 5,922,284 | A | * | 7/1999 | Kinoshita et al. ........... 422/68.1 |
| 4,888,278 | A | * | 12/1989 | Singer et al. ..................... 435/6 | 5,932,309 | A |   | 8/1999 | Smith et al. |
| 4,893,886 | A | * | 1/1990 | Ashkin et al. ................ 359/350 | 5,935,779 | A | * | 8/1999 | Massey et al. .................. 435/6 |
| 4,912,035 | A | * | 3/1990 | Belly et al. .................... 435/29 | 5,989,923 | A | * | 11/1999 | Lowe et al. ................. 436/518 |
| 4,935,147 | A | * | 6/1990 | Ullman et al. ............... 210/695 | 5,998,129 | A | * | 12/1999 | Schutze et al. .................. 435/4 |
| 4,966,856 | A | * | 10/1990 | Ito et al. ....................... 436/170 | 6,010,888 | A | * | 1/2000 | Liotta et al. ................. 435/100 |
| 5,028,339 | A | * | 7/1991 | Clark, III ................... 210/688 | 6,013,532 | A | * | 1/2000 | Liberti et al. ................. 436/526 |
| 5,037,762 | A | * | 8/1991 | Mura et al. .................. 436/164 | 6,060,237 | A | * | 5/2000 | Nygren et al. .................. 435/6 |
| 5,045,477 | A | * | 9/1991 | Belly et al. .................. 436/164 | 6,087,134 | A | * | 7/2000 | Saunders .................... 435/91.2 |
| 5,064,768 | A | * | 11/1991 | Ebata et al. ................. 436/164 | 6,121,027 | A | * | 9/2000 | Clapper et al. ............. 435/180 |
| 5,076,950 | A | * | 12/1991 | Ullman et al. ........ 252/62.51 R | 6,121,425 | A | * | 9/2000 | Hainfeld et al. .......... 530/391.5 |
| 5,093,238 | A | * | 3/1992 | Yamashoji et al. ............ 435/29 | 6,127,122 | A | * | 10/2000 | Park et al. ..................... 435/6 |
| 5,108,933 | A | * | 4/1992 | Liberti et al. ................ 436/501 | 6,134,747 | A | * | 10/2000 | Leibman ....................... 16/24 |
| 5,110,723 | A | * | 5/1992 | Mura et al. .................... 435/4 | 6,136,182 | A | * | 10/2000 | Dolan et al. .................. 210/94 |
| 5,116,734 | A | * | 5/1992 | Higgs et al. .................. 435/28 | 6,139,831 | A | * | 10/2000 | Shivashankar et al. ...... 530/351 |
| 5,141,855 | A | * | 8/1992 | Schmittou .................... 435/34 | 6,143,514 | A | * | 11/2000 | Ullman et al. ................ 435/28 |
| 5,176,999 | A | * | 1/1993 | McClune et al. ............ 435/7.5 | 6,149,789 | A | * | 11/2000 | Benecke et al. ............. 204/547 |
| 5,192,688 | A | * | 3/1993 | Switzer et al. ................. 436/63 | 6,159,681 | A | * | 12/2000 | Zebala ............................ 435/4 |
| 5,198,369 | A | * | 3/1993 | Itoh et al. ..................... 436/534 | 6,159,686 | A |   | 12/2000 | Kardos et al. |
| 5,202,227 | A | * | 4/1993 | Matsuda et al. ............ 430/320 | 6,159,689 | A | * | 12/2000 | Parton ........................... 435/6 |
| 5,206,122 | A | * | 4/1993 | Noppe et al. ............... 430/414 | 6,162,278 | A | * | 12/2000 | Hu ................................ 75/345 |
| 5,212,382 | A | * | 5/1993 | Sasaki et al. ................. 250/251 | 6,177,151 | B1 | * | 1/2001 | Chrisey et al. ............. 427/596 |
| 5,221,446 | A | * | 6/1993 | Eerkens ................. 204/157.22 | 6,180,354 | B1 | * | 1/2001 | Singh et al. ................. 435/7.1 |
| 5,256,271 | A | * | 10/1993 | Ikariyama et al. ........... 205/109 | 6,180,415 | B1 | * | 1/2001 | Schultz et al. .............. 436/518 |
| 5,266,498 | A | * | 11/1993 | Tarcha et al. ................ 436/525 | 6,194,157 | B1 | * | 2/2001 | Tsuchiya et al. ................ 435/6 |
| 5,269,903 | A | * | 12/1993 | Ikariyama et al. ...... 204/403.11 | 6,197,387 | B1 | * | 3/2001 | Fiedler et al. ................ 427/532 |
| 5,279,936 | A | * | 1/1994 | Vorpahl ........................ 435/6 | 6,204,030 | B1 | * | 3/2001 | Liotta et al. ................. 435/100 |
| 5,296,111 | A | * | 3/1994 | Suzuki et al. ................ 210/611 | 6,214,560 | B1 | * | 4/2001 | Yguerabide et al. .......... 435/7.1 |
| 5,306,624 | A | * | 4/1994 | Roelant ........................ 435/39 | 6,225,047 | B1 | * | 5/2001 | Hutchens et al. ................ 435/5 |
| 5,332,662 | A | * | 7/1994 | Ullman ....................... 435/28 | 6,228,248 | B1 | * | 5/2001 | Aksay et al. ................. 205/687 |
| 5,340,716 | A | * | 8/1994 | Ullman et al. .................. 435/6 | 6,251,467 | B1 | * | 6/2001 | Liotta et al. ................. 427/2.11 |
| 5,366,864 | A | * | 11/1994 | McClune et al. ............ 435/7.5 | 6,251,516 | B1 | * | 6/2001 | Bonner et al. ............... 428/346 |
| 5,428,451 | A |   | 6/1995 | Lea et al. | 6,251,581 | B1 | * | 6/2001 | Ullman et al. .................. 435/4 |
| 5,432,077 | A | * | 7/1995 | Farrah ....................... 435/244 | 6,251,691 | B1 |   | 6/2001 | Seul |

| | | | |
|---|---|---|---|
| 6,258,607 B1 * | 7/2001 | Saito et al. | 436/526 |
| 6,303,516 B1 * | 10/2001 | Morita et al. | 438/758 |
| 6,306,594 B1 * | 10/2001 | Cozzette et al. | 435/6 |
| 6,316,153 B1 * | 11/2001 | Goodman et al. | 430/8 |
| 6,316,267 B1 * | 11/2001 | Bhalgat et al. | 436/86 |
| 6,340,599 B1 * | 1/2002 | Singh et al. | 436/534 |
| 6,346,384 B1 * | 2/2002 | Pollner | 435/6 |
| 6,368,866 B1 * | 4/2002 | Lawlor et al. | 436/74 |
| 6,369,206 B1 * | 4/2002 | Leone et al. | 530/391.5 |
| 6,379,976 B1 * | 4/2002 | Tengvall et al. | 436/518 |
| 6,387,707 B1 * | 5/2002 | Seul et al. | 436/164 |
| 6,406,913 B1 * | 6/2002 | Ullman et al. | 435/41 |
| 6,444,453 B1 * | 9/2002 | Lauf et al. | 435/168 |
| 6,495,195 B2 * | 12/2002 | Baer et al. | 427/2.11 |
| 6,495,340 B2 * | 12/2002 | Huberman et al. | 435/30 |
| 6,501,071 B1 * | 12/2002 | Hatase | 250/251 |
| 6,514,734 B1 * | 2/2003 | Clapper et al. | 435/180 |
| 6,514,771 B1 | 2/2003 | Seul | |
| 6,541,022 B1 * | 4/2003 | Murphy et al. | 424/422 |
| 6,547,940 B2 * | 4/2003 | Aksay et al. | 204/450 |
| 6,558,448 B2 * | 5/2003 | Hu | 75/252 |
| 6,576,461 B2 * | 6/2003 | Heller et al. | 435/287.9 |
| 6,586,193 B2 * | 7/2003 | Yguerabide et al. | 435/7.92 |
| 6,613,578 B1 * | 9/2003 | Moller et al. | 436/172 |
| 6,623,983 B1 * | 9/2003 | Terstappen et al. | 436/526 |
| 6,635,489 B2 * | 10/2003 | Whitney | 436/86 |
| 6,645,464 B1 * | 11/2003 | Hainfeld | 424/1.29 |
| 6,670,113 B2 * | 12/2003 | Hainfeld | 435/4 |
| 6,692,975 B2 * | 2/2004 | Singh et al. | 436/534 |
| 6,703,235 B2 * | 3/2004 | Luebke et al. | 435/283.1 |
| 6,706,479 B2 * | 3/2004 | Saraf et al. | 435/6 |
| 6,713,772 B2 * | 3/2004 | Goodman et al. | 250/492.1 |
| 6,767,928 B1 * | 7/2004 | Murphy et al. | 521/51 |
| 6,770,488 B1 * | 8/2004 | Carron et al. | 436/525 |
| 6,852,425 B2 * | 2/2005 | Hu | 428/548 |
| 6,875,329 B2 * | 4/2005 | Washizu et al. | 204/547 |
| 6,881,589 B1 * | 4/2005 | Leland et al. | 436/501 |
| 6,887,703 B2 * | 5/2005 | Baer et al. | 435/325 |
| 6,893,850 B2 * | 5/2005 | Ostuni et al. | 435/174 |
| 6,897,015 B2 * | 5/2005 | Henderson et al. | 435/5 |
| 6,905,738 B2 * | 6/2005 | Ringeisen et al. | 427/596 |
| 6,916,667 B2 * | 7/2005 | Singh et al. | 436/534 |
| 6,955,639 B2 * | 10/2005 | Hainfeld et al. | 600/1 |
| 6,958,245 B2 * | 10/2005 | Seul et al. | 436/534 |
| 7,022,523 B2 * | 4/2006 | Tsuzuki et al. | 435/401 |
| 7,056,748 B1 * | 6/2006 | Braun et al. | 436/518 |
| 7,060,473 B2 * | 6/2006 | Phelps et al. | 435/168 |
| 7,067,104 B2 * | 6/2006 | Sandhage | 423/592.1 |
| 7,071,006 B2 * | 7/2006 | Tajima et al. | 436/526 |
| 7,074,622 B2 * | 7/2006 | Qiao et al. | 436/518 |
| 7,204,971 B2 * | 4/2007 | Sandhage | 423/592.1 |
| 7,229,842 B2 * | 6/2007 | Singh et al. | 436/546 |
| 7,285,412 B2 * | 10/2007 | Casagrande et al. | 435/297.1 |
| 2003/0060873 A1 * | 3/2003 | Gertner et al. | 623/1.15 |
| 2003/0203002 A1 * | 10/2003 | Murphy et al. | 424/423 |
| 2004/0053326 A1 * | 3/2004 | Emmert-Buck et al. | 435/7.1 |
| 2004/0175407 A1 * | 9/2004 | McDaniel | 424/423 |
| 2004/0231988 A1 * | 11/2004 | Pillar et al. | 204/451 |
| 2004/0265922 A1 * | 12/2004 | Bieniarz et al. | 435/7.5 |
| 2005/0100976 A1 * | 5/2005 | Bieniarz et al. | 435/7.92 |
| 2005/0176068 A1 * | 8/2005 | Emmert-Buck et al. | 435/7.2 |
| 2005/0233442 A1 * | 10/2005 | Toda et al. | 435/325 |
| 2006/0134692 A1 * | 6/2006 | Emmert-Buck et al. | 435/7.1 |
| 2006/0172278 A1 * | 8/2006 | Bonner et al. | 435/4 |

FOREIGN PATENT DOCUMENTS

| | | | |
|---|---|---|---|
| EP | 0 372 352 | * | 6/1990 |
| WO | WO 97/40385 | | 10/1997 |

OTHER PUBLICATIONS

Van de Sande, CC. Dye diffusion systems in color photography. Angew. Chem. Int. Ed. Engl. 1983;22:191-209.*

Reeves, S.G. & Hall, D.O. Higher plant chloroplasts and grana: general preparative procedures (excluding high carbon dioxide fixation ability chloroplasts. Methods Enzymol. 1980;69:85-94.*

Kodak, Inc. Materials Safety Data Sheet, Product code 1901859 (Kodak GBX Developer).*

Keller, K. et al. Photography. Ullmann's Encyclopedia of Industrial Chemistry, vol. 26, John Wiley & Sons, Inc. (2007). (publisher's online publication date, Jun. 15, 2000). pp. 1-169.*

Ilford Q Plates, Fact Sheet (Dec. 2005), Ilford Photo, Harman Technology, Ltd., available at <http://www.ilfordphoto.com> (retrieved Oct. 15, 2007). pp. 1-2.*

Vo-Dinh, T. Surface-enhanced Raman spectroscopy using metallic nanostructures. Trends Anal. Chem. 1998;17:557-582.*

Burton, M.P. et al. Comparison of histologic stains for use in PCR analysis of microdissected, paraffin-embedded tissues (Short technical reports). BIOTECHNIQUES. 1998;24:86-91.*

Halbhuber, K.J. et al. Reflectance enzyme histochemistry (REH): visualization of cerium-based and DAB primary reaction products of phosphatases and oxidases in cryostat sections by confocal laser scanning microscopy. Histochem. Cell Biol. 1996;105:239-249.*

Quinn, B. & Graybiel, A.M. A differentiated silver intensification procedure for the peroxidase-diaminobenzidine reaction. J. Histochem. Cytochem. 1996;44:71-74.*

Vo-Dinh, T. et al. Surface-enhanced Raman gene probes. Anal. Chem. 1994;66:3379-3383.*

Smiley, J.F. & Goldman-Rakic, P.S. Silver-enhanced diaminobenzidine-sulfide (SEDS): A technique for high-resolution immunoelectron microscopy demonstrated with monoamine immunoreactivity in monkey cerebral cortex and caudate. J. Histochem. Cytochem. 1993;41:1393-1404.*

Goto, S. et al. A simple enhancement method for the silver-gold-intensified diaminobenzidine reaction in the light microscopic immunoperoxidase technique. J. Histochem. Cytochem. 1992;40:1423-1425.*

Mullink, H. et al. Application and comparison of silver intensification methods for the diaminobenzidine and diaminobenzidine-nickel endproduct of the peroxidation reaction in immunohistochemistry and in situ hybridization. J. Histochem. Cytochem. 1992;40:495-504.*

Toni, R. & Lechan, R.M. 1-naphthol-pyronin B as a novel substrate for silver intensification: Application to light and electron microscopic immunocytochemistry of neuroendocrine systems. J. Histochem. Cytochem. 1990;38:1209-1214.*

Green, M.A. et al. Improved method for immunoperoxidase detection of membrane antigens in frozen sections. J. Clin. Pathol. 1989;42:875-880.*

Merchenthaler, I. et al. A highly sensitive one-step method for silver intensification of the nickel-diaminobenzidine endproduct of peroxidase reaction. J. Histochem. Cytochem. 1989;37:1563-1565.*

Konttinen, Y.T. et al. An immunoperoxidase-autoradiography double labeling method for analysis of lymphocyte activation markers and DNA synthesis. J. Immunol. Methods. 1988;110:19-27.*

Gallyas, F. & Merchenthaler, I. Copper-H2O2 oxidation strikingly improves silver intensification of the nickel-diaminobenzidine (Ni-DAB) end-product of the peroxidase reaction. J. Histochem. Cytochem. 1988;36:807-810.*

Ahern, A.M. & Garrell, R.L. In situ photoreduced silver nitrate as a substrate for surface-enhanced Raman spectroscopy. Anal. Chem. 1987;59:2813-2816.* van den Pol, A.N. Tyrosine hydroxylase immunoreactive neurons throughout the hypothalamus receive glutamate decarboxylase immunoreactive synapses: A double pre-embedding immunocytochemical study with particulate silver and HRP. J. Neurosci. 1986;6:877-891.*

Gorcs, T.J. et al. The use of gold-substituted silver-intensified diaminobenzidine (DAB) and non-intensified DAB for simultaneous electron microscopic immunoperoxidase labeling of tyrosine hydroxylase and glutamic acid decarboxylase immunoreactivity in the rat medial preoptic area. J. Histochem. Cytochem. 1986;34:1439-1447.*

Gallyas, F. & Wolff, J.R. Metal-catalyzed oxidation renders silver intensification selective. J. Histochem. Cytochem. 1986;34:1667-1672.*

Liposits, Z. et al. Ultrastructural analysis of central serotoninergic neurons immunolabeled by silver-gold-intensified diaminobenzidine chromogen. J. Histochem. Cytochem. 1985;33:604-610.*

Gallyas, F. et al. High-grade intensification of the end-product of the diaminobenzidine reaction for peroxidase histochemistry. J. Histochem. Cytochem. 1982;30:183-184.*

LeBouteiller, P.P. & Asherson, G.L. Detection of radiolabelled bone marrow cells bearing surface immunoglobulins by combined autoradiography and immunoperoxidase. J. Immunol. Methods. 1981;41:173-186.*

Lillie, R.D. Metal reduction reactions of the melanins: Histochemical studies. J. Histochem. Cytochem. 1957;5:325-333.*

Ilford, Ltd. New photographic emulsions of interest to physicists. J. Sci. Instrum. 1935;12:333-335.*

International Search Report for PCT/IL02/00256, mailed Dec. 7, 2004.

Gallyas: "supression of the argyrophil III reaction by mercapto compounds (A preequisite for the intesification of certain histochemical reactions by physical developers)" Acta Histochemica, vol. 70, No. 1, 1982, pp. 99-105, XP009062279 abstract p. 103, paragraph 2—p. 105, paragraph 2.

* cited by examiner

*Primary Examiner*—Long V. Le
*Assistant Examiner*—David J. Venci
(74) *Attorney, Agent, or Firm*—Pearl Cohen Zedek Latzer LLP

(57) ABSTRACT

We disclose methods of sorting or separating mixtures of living cells (e.g., eukaryotic, prokaryotic, mammalian, pathogenic, bacterial, viral, etc.). We perform our methods by activating cell-selective photophoric labels, which photosensitize and chemically reduce a photosensitive metal compound to form metal grains, particles or crystals. The metal adheres to the cells and forms the basis for sorting or separating different cell types. Photophoric labels may include chemiluminescent agents such as peroxidase enzymes activated with peroxidase substrates capable of luminescence. Photosensitive metal compounds may be present in a light-sensitive matrix or emulsion containing photosensitizable metal compounds, which form metal grains, particles or crystals upon exposure to a developer solution. Developer solutions are formulated to substantially allow living cells to remain viable after exposure to the developing solution. Our methods are useful in flow cytometry and fluorescence activated cell sorting (FACS) methods, microdissection methods, and for attracting, sedimenting, depositing, layering, attaching, adhering, bonding, binding, trapping or suspending cells on surfaces.

55 Claims, 15 Drawing Sheets

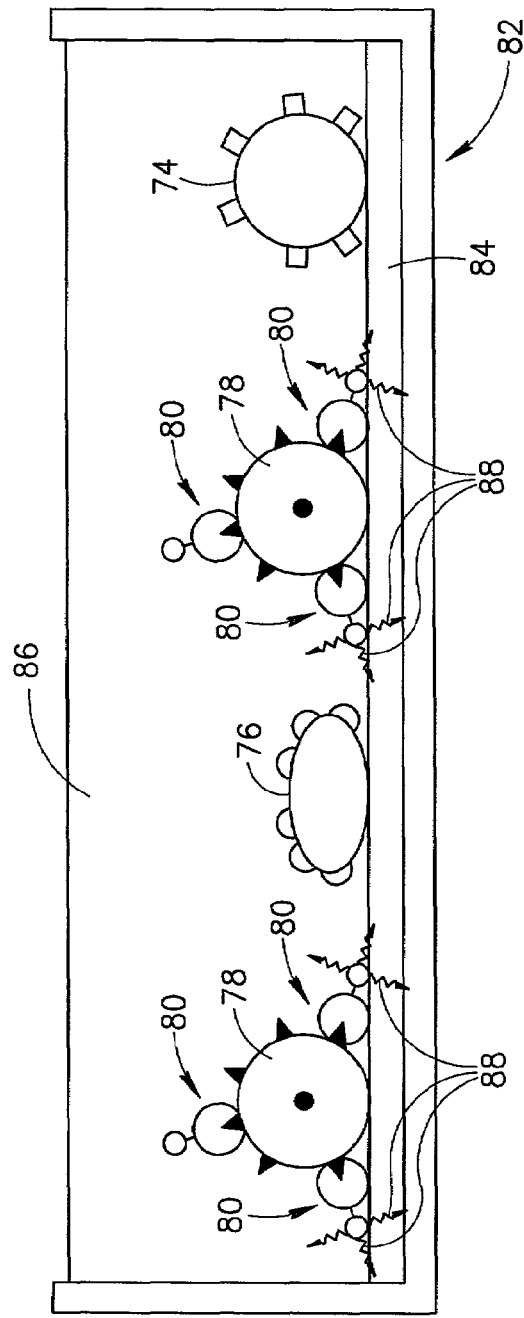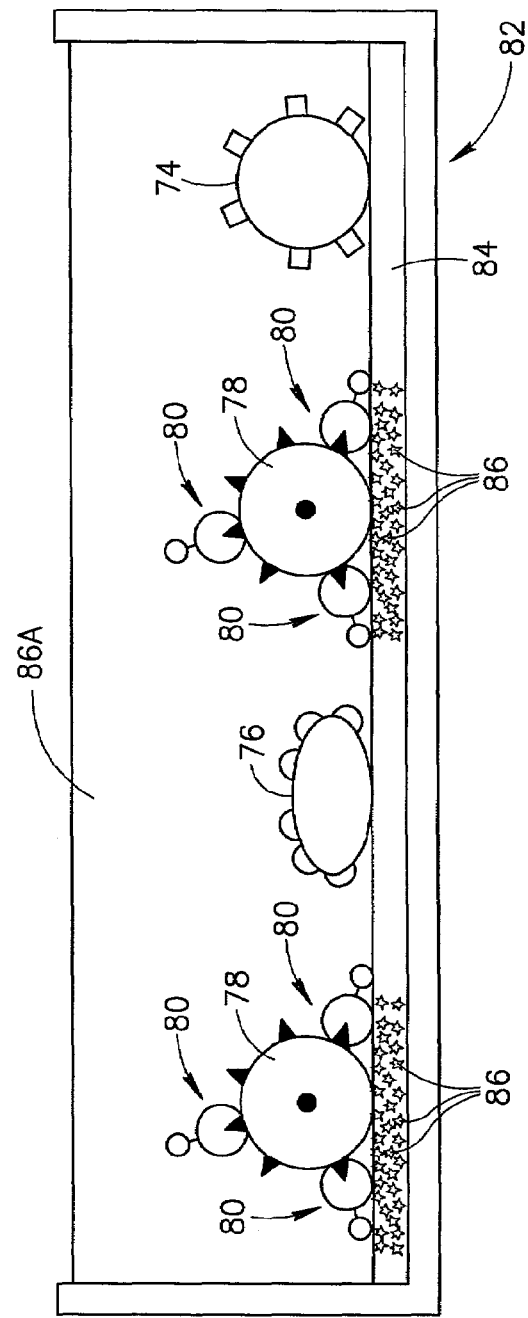

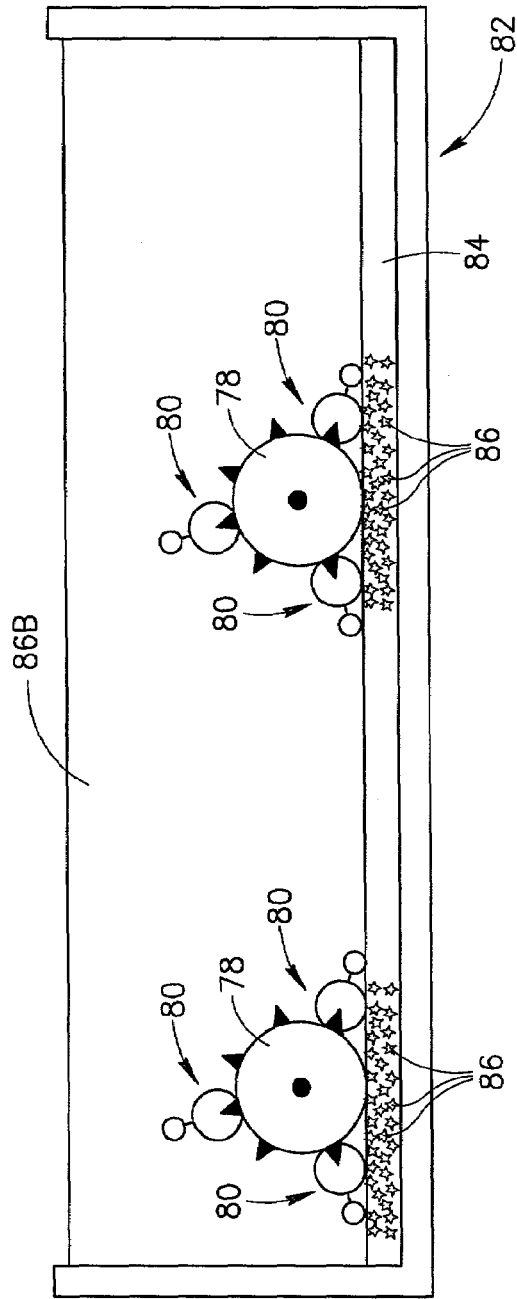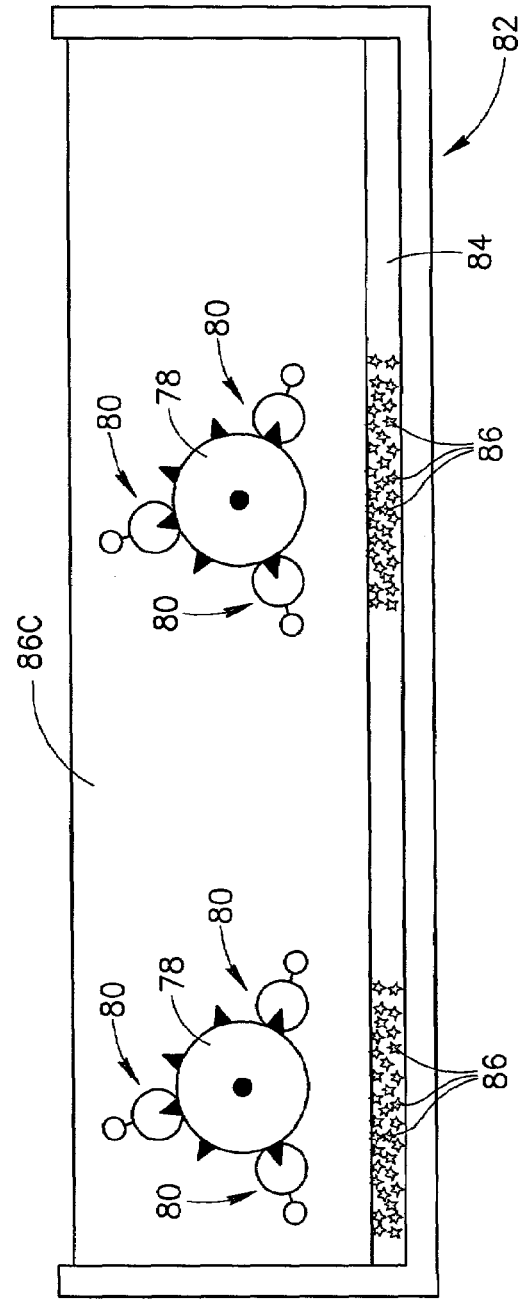

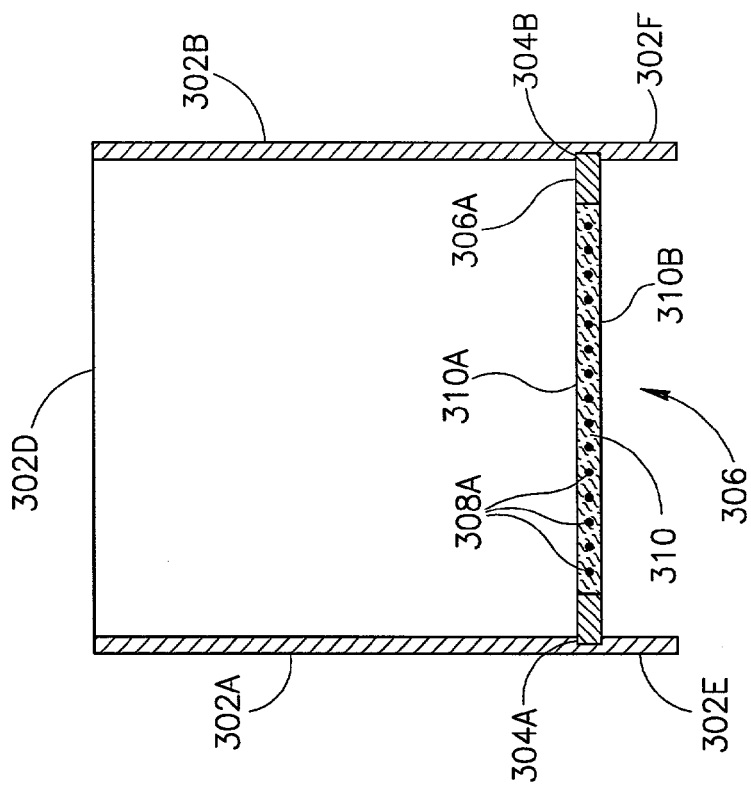
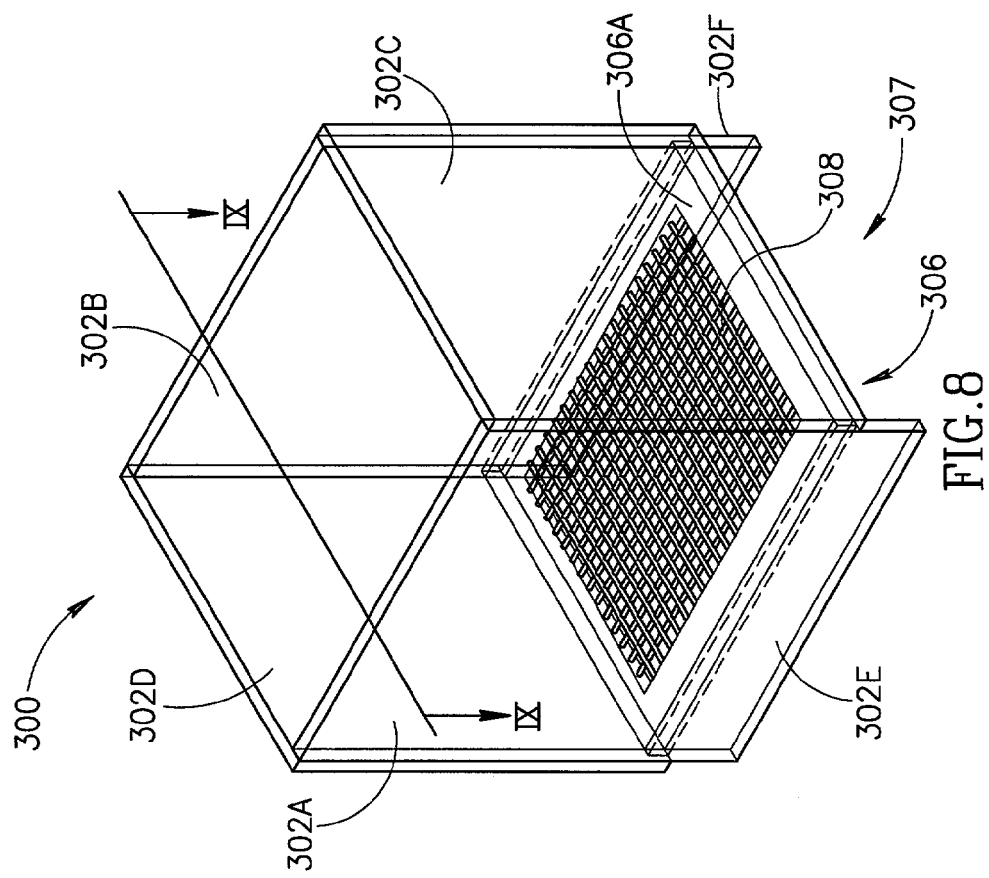
FIG. 9
FIG. 8

METHOD FOR SORTING AND SEPARATING LIVING CELLS

RELATED APPLICATIONS

This application claims the benefit of provisional application Ser. No. 60/279,447, filed on Mar. 29, 2001, which is incorporated in its entirety by reference herein for all purposes.

FIELD OF THE INVENTION

The present invention relates generally to the field of methods and devices for sorting and/or separating particles and more specifically to methods and devices based on adherence of the particles to metal grains locally formed in a light sensitive layer by localized irradiation with light.

BACKGROUND OF THE INVENTION

The separation and sorting of particles having different properties has many valuable industrial, medical, pharmaceutical, diagnostic, and scientific applications. Various different methods and devices for the separation and/or sorting of particles based on differences in physical or chemical properties of the particles are known in the art.

For example, methods for separating or sorting living cells, sub-cellular components and organelles, or other macromolecules or molecular complexes or multimolecular aggregates of biological or synthetic origin are often required in the fields of biotechnology, medicine, diagnostic tests, and processes associated with drug development and drug screening. Such sorting or separation methods may include, inter alia, centrifugation methods, density gradient separation methods, magnetic-based separation methods, flow cytometry (FC) methods, and fluorescence assisted cell sorting (FACS) methods. Advanced methods for cell sorting, separation, and manipulation may use various different methods of trapping and manipulation of particles, cells and sub-cellular organelles by using laser beam trapping and manipulation (also known as "laser tweezers").

SUMMARY OF THE INVENTION

There is therefore provided, in accordance with an embodiment of the present invention, a method for sorting or separating different particles.

The method includes the steps of providing a fluid containing a mixture of different particles suspended therein. The mixture of particles includes one or more target particle;

selectively labeling at least one target particle of the target particles with a photophoric probe to form at least one labeled target particle in the fluid. The photophoric probe is capable of being controllably activated to produce localized emission of light in the vicinity of the at least one labeled target particle;

providing a light sensitive substrate including at least one photosensitizable metal compound;

applying the fluid to the light sensitive substrate such that at least one labeled target particle is adjacent to the light sensitive substrate;

activating said photophoric probe to produce localized emission of light in the vicinity of the at least one labeled target particle, the light photosensitizes at least portions of the light sensitive substrate to form photosensitized portions of the substrate;

developing the photosensitized portions to form metal grains in the photosensitized portions;

allowing the at least one labeled target particle to adhere to the metal grains; and removing the particles of the mixture of different particles which do not adhere to the metal grains.

There is further provided, in accordance with an embodiment of the present invention, a system for sorting particles. The system includes:

optical means configured for identifying a selected particle type based on at least one property of the particle type;

light generating means configured for applying light to at least a portion of a light sensitive substrate. The portion is adjacent to or in contact with a target particle of the selected particle type. The light is adapted to photosensitize a metal compound included within the substrate. The photosensitized metal compound is capable of being developed to form metal grains within the portion of the substrate. The metal grains are capable of binding to or adhering to the target particle to attach the target particle to the substrate;

removing means for removing particles which are not attached to the substrate.

There is further provided, in accordance with an embodiment of the present invention, a method for attaching particles to a substrate, the method includes the steps of:

providing a light sensitive substrate comprises at least one photosensitizable metal compound;

contacting the substrate with a fluid having particles suspended therein such that at least some of the particles are in contact with the substrate;

selectively exposing to light portions of the light sensitive substrate to form photosensitized portions of the substrate. The portions are in the vicinity of or in contact with one or more of the particles;

developing the photosensitized portions to form metal grains in the photosensitized portions; and allowing at least one of the particles to adhere to the metal grains.

There is further provided, in accordance with an embodiment of the present invention, a method for sorting or separating different particles. The method includes the steps of:

providing a light sensitive substrate comprising at least one photosensitizable metal compound;

contacting the substrate with a mixture of different particles suspended in a fluid such that at least some of the particles are in contact with the substrate;

selectively exposing to light portions of the substrate, to form photosensitized portions of said substrate. The portions are in the vicinity of or in contact with one or more target particles included in the mixture of different particles;

developing the photosensitized portions to form metal grains in the photosensitized portions;

allowing at least one of the target particles to adhere to the metal grains; and removing particles which do not adhere to the metal grains.

There is further provided, in accordance with an embodiment of the present invention, a method for sorting or separating different particles. The method includes the steps of:

providing a light sensitive substrate including at least one photosensitizable metal compound;

contacting the substrate with a mixture of different particles suspended in a fluid such that most of the particles are in contact with the substrate. The particles include target particles and non-target particles;

selectively exposing to light portions of the substrate to form photosensitized portions of said substrate. The portions are in the vicinity of or in contact with one or more of the non-target particles included in the mixture of different particles;

developing the photosensitized portions to form metal grains in the photosensitized portions;

allowing at least some of the non-target particles to adhere to the metal grains; and collecting the target particles which do not adhere to the metal grains.

There is further provided, in accordance with an embodiment of the present invention, a method for sorting or separating different particles. The method includes the steps of:

providing a fluid containing a mixture of different particles suspended therein, the mixture of particles includes one or more target particles;

selectively labeling at least one target particle of the one or more target particles with a photophoric probe to form at least one labeled target particle in the fluid. The photophoric probe is capable of being controllably activated to produce localized emission of light in the vicinity of the at least one labeled target particle;

providing a light sensitive substrate. The substrate includes at least one photosensitizable metal compound;

applying the fluid to the light sensitive substrate such that at least one labeled target particle is adjacent to or in contact with the surface of the light sensitive substrate;

activating said photophoric probe to produce localized emission of light in the vicinity of the at least one labeled target particle, the light photosensitizes at least portions of the light sensitive substrate to form photosensitized portions of the substrate;

developing the photosensitized portions to form metal grains in the photosensitized portions;

allowing said at least one labeled target particle to adhere to the metal grains; and removing the particles which do not adhere to the metal grains.

There is further provided, in accordance with an embodiment of the present invention, a method for separating particles. The method includes the steps of:

providing a fluid containing a mixture of different particles suspended therein. The mixture of particles includes one or more target particles and one or more non-target particles;

selectively labeling most of the non-target particles of the fluid with a photophoric probe to form labeled non-target particles in the fluid. The photophoric probe is capable of being controllably activated to produce localized emission of light in the vicinity of the labeled non-target particles;

providing a light sensitive substrate. The substrate includes at least one photosensitizable metal compound;

applying the fluid to the light sensitive substrate such that most labeled non-target particles are adjacent to or in contact with the surface of the light sensitive substrate;

activating the photophoric probe to produce localized emission of light in the vicinity of the labeled non-target particles. The light photosensitizes at least portions of the light sensitive substrate to form photosensitized portions of the substrate;

developing the photosensitized portions to form metal grains in the photosensitized portions;

allowing the labeled non-target particle to adhere to the metal grains; and collecting the particles which do not adhere to the metal grains to obtain an enriched particle population having a higher ratio of the target particles to the non-target particles.

There is further provided, in accordance with an embodiment of the present invention, a method for attaching particles to a substrate. The method includes the steps of:

providing a light sensitive substrate including at least one photosensitizable metal compound;

contacting the substrate with a fluid having particles suspended therein such that at least some of the particles are in contact with the substrate;

exposing the light sensitive substrate to light, to photosensitive the substrate;

developing the photosensitized substrate to form metal grains in the substrate; and allowing at least one of the particles to adhere to the metal grains.

There is further provided, in accordance with an embodiment of the present invention, a method for attaching particles to a substrate. The method includes the steps of:

providing a light sensitive substrate including at least one photosensitizable metal compound;

contacting the substrate with a fluid having at least one particle suspended therein such that the at least one particle is in contact with the substrate;

exposing the light sensitive substrate to light, to photosensitive the substrate;

developing the photosensitized substrate to form metal grains in the substrate; and allowing the at least one particle to adhere to the metal grains.

Furthermore, in accordance with embodiments of the present invention, the particles may be inorganic particles, macromolecules, cellular aggregates, eukaryotic cells, prokaryotic cells, mammalian cells, non-mammalian cells, viable cells, dead cells, fixed cells, subcellular organelles, sub-cellular particles, cell membranes or fragments thereof, pathogenic organisms, non-pathogenic organisms, bacterial cells, viruses, prions, nanobacteria, unicellular organisms, multicellular organisms, isolated genes or fragments thereof, chromosomes, parts or fragments of chromosomes, single subunit or multi-subunit protein molecules, modified protein molecules, proteoglycans, glycoproteins, DNA, RNA, and olygonucleotides.

Furthermore, in accordance with an embodiment of the present invention, the photophoric probe includes a first affinity probe capable of specifically and selectively binding to a selected particle type or to at least a second affinity probe bound to a selected particle type, and a second portion linked to the first affinity probe and capable of being controllably induced to emit light or to cause the emission of light in the vicinity of a particle to which the photophoric probe is bound.

Furthermore, in accordance with an embodiment of the present invention, the first affinity probe is selected from an antibody or a fragment thereof, a toxin having an affinity for at least a portion of a selected particle type, an oligonucleotyde probe, a protein based affinity probe, a glycoprotein based affinity probe, and a hapten or molecule having an affinity for at least a portion of a selected particle type.

Furthermore, in accordance with an embodiment of the present invention, the second portion of the photophoric probe is selected from, a chemiluminescent moiety or agent, a fluorescent moiety or agent, an upconverting moeity or particle or agent, an inorganic two photon upconverting anti-stokes phosphor particle, a two photon upconverting dye, a bioluminescent protein, a bioluminescent or a chemiluminescent molecule, a thermoluminescent moiety or agent or particle, and an electroluminescent moiety or agent or particle.

Furthermore, in accordance with an embodiment of the present invention, the second portion of the photophoric probe comprises an enzyme capable of participating in a chemiluminescent chemical reaction, or capable of activating or catalyzing of a chemiluminescent chemical reaction resulting with the production of light, or capable of catalyzing a chemical reaction for producing a reaction product capable of reacting with at least one chemical in a chemiluminescent reaction resulting in the production of light.

Furthermore, in accordance with an embodiment of the present invention, the second portion of the photophoric probe includes aequorin or obelin.

Furthermore, in accordance with an embodiment of the present invention,the second portion of the photophoric probe comprises a an enzyme selected from the group including peroxidases, phosphatases, alkaline-phosphatases, galactosidases, and a β-glucuronidases.

BRIEF DESCRIPTION OF THE DRAWINGS

The invention is herein described, by way of example only, with reference to the accompanying drawings, in which like components are designated by like reference numerals, wherein:

FIGS. 5A-5F are schematic diagrams useful in understanding a method for separating, or sorting or purifying or isolating particles or cells, in accordance with another preferred embodiment of the present invention;

FIG. 8 is a schematic partially isometric view of a particle holder usable for separating cells or other particles, in accordance with one preferred embodiment of the present invention;

FIG. 9 is a schematic cross sectional view of the particle holder illustrated in FIG. 8 taken along the lines IX-IX;

DETAILED DESCRIPTION OF THE INVENTION

Figure 1A:
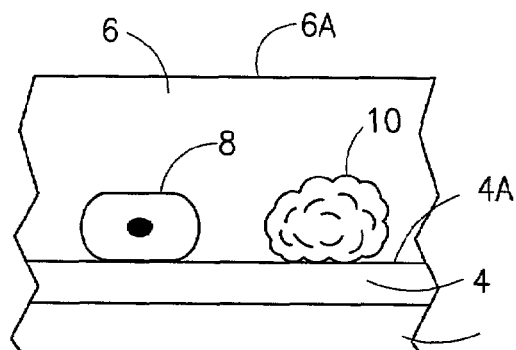
FIGS. 1A-1F are schematic diagrams illustrating a particle sorting and/or separating method, in accordance with one preferred embodiment of the present invention.

The following terms and abbreviations are used throughout the application:

| Term | Definition |
| --- | --- |
| APS | Ammonium persulfate |
| BSA | Bovine serum albumin |
| CFDA | Carboxyfluorescine diacetate |
| DDW | Doubly Deionized Water |
| DIC | Differential Interference Contrast |
| DMSO | Dimethylsulfoxide |
| EDTA | Ethylenediaminetetraacetic acid |
| FACS | Fluorescence Assisted Cell Sorting |
| FC | Flow Cytometry |
| FCS | Fetal Calf Serum |
| FISH | Fluorescence In-Situ Hybridization |
| M | molar |
| mg | milligrams |
| ml | milliliters |
| mM | millimolar |
| N | Normal |
| NRBC | Nucleated Red Blood cells |
| PBS | Phosphate Buffered Saline |
| PHA | Phytohemagglutinin-A |
| RBCs | Red Blood Cells |
| RPM | Revolutions per minute |
| SDS | Sodium dodecyl sulfate |
| TEMED | N,N,N',N' Tetramethylethylenediamine |
| WBC | White Blood Cells |

The present invention is related to novel methods and devices for sorting and/or separating particles. The method is generally based on selective induction by light of growth of metal grains or metal crystals on a surface of a light sensitive layer which may be disposed on a substrate, or may be suitably attached to a substrate, or coated on a substrate. The particle or particles may adhere or bind to the light sensitive surface by adhering or binding to metal grains or crystals formed on the light sensitive surface, and may become immobilized due to the adherence or binding to the metallic surfaces. The separation may then be completed by washing the surface to remove the non-adhering (non-immobilized) particles.

An aspect of the present invention is the ability of at least one type of particle or particles to interact with the metal surfaces of the metal grains, metal particles or metal crystals formed on the surface of the light sensitive layer resulting in the immobilization of the interacting particle or particles due to their adherence or binding to the metallic surfaces.

The immobilized particles may be (optionally) recovered from the surface, if required, by an appropriate treatment (Such as, but not limited to, treatment with a chemical) which may detach the immobilized particle(s) from the light sensitive surface and/or from the metal grains or metal crystals. In non-limiting examples, when the particles to be sorted or separated are isolated eukaryotic or prokaryotic cells (either viable or dead), the cells may typically adhere or bind to the metallic surface by physical, or chemical-physical, or chemical interactions between the metallic surface and molecules on the surface of the particle(s), such as, for example, surface proteins exposed on the outer side of the cell's membranes. In such a non-limiting exemplary case, detachment of the adhering cells from the light sensitive layer may be performed by subjecting the cells to a proteolytic enzyme, such as, but not limited to, trypsin, pepsin, papain, or the like, which cuts the extracellular proteins that bind the cells to the metallic surfaces, thus enabling harvest of the cells for further use or analysis. However, other different particle detachment methods may be used for various types of particles. Examples of other particle detachment methods may be, but are not limited to, the dissolution of the matrix constituting the light sensitive layer in order to release the particle(s) therefrom, and/or the direct dissolution of the metallic material bound to the particles. For example, if an agarose matrix is used as part of the light sensitive layer, the matrix may be melted by heating to 40°-50° C., and the particles may be harvested by filtration, or by centrifugation, or by other suitable methods.

Another exemplary method includes the use of a light sensitive matrix including a calcium-alginate gel which may be dissolved upon addition of suitable cation chelators or other calcium sequestering agents, such as, but not limited to, EDTA or sodium citrate, or the like. After gel dissolution, the metallic grains or crystals may be removed (if required) from the isolated particles, using an appropriate metal dissolving solution formulated for dissolving the metal grains. An example for such a metal dissolving solution formulated for dissolving silver metal grains is disclosed in detail hereinafter.

Such methods may be used with inorganic particles, or with dead or fixed cells, or with living cells which may survive the conditions used for cell attachment and detachment.

Additionally, in accordance with another preferred embodiment of the invention, the light sensitive matrix may be formed from paraffin in which a silver halide (or another light sensitive metal salt) is dispersed. After the cells (or other particles) adhere to the silver particles developed on this matrix, the matrix may be dissolved in glycerin to harvest the cells. This method has the advantage that glycerin is compatible with living cells, allowing the harvesting of live cells from the paraffin matrix.

In the example disclosed hereinabove describing the use of a calcium alginate matrix, the light sensitive matrix may include a matrix of calcium alginate gel in which a silver halide is dispersed. After the development of the silver metal grains and the adhering of the cells (or other particles) to the silver metal grains developed in the matrix, the cells may be harvested by applying a suitable solution containing EDTA to the matrix which dissolves the matrix by preferentially binding the calcium ions of the calcium alginate gel matrix. Experiments using alginate matrices are disclosed in detail hereinafter.

Another alternative, in accordance with another preferred embodiment of the invention, is to dissociate the cells or particles from the silver grains to which they are bound by treating the matrix with the bound cells or particles with a solution including one or more ligands or substances which may compete for the binding sites on the surface of the silver grains and in this way either completely detach the bound cells or particles from the silver grains or, alternatively, weaken the adhesion between the silver grains and the adhering cells sufficiently to make possible the detaching of the adhering cells or particles by washing or by other mechanical agitation methods. Such ligands may include substances or compounds having an ability to bind to the surface of silver grains such as but not limited to various amino acids, amines, organic or inorganic ions having an affinity for silver metal surfaces, or the like.

Generally, the method and devices of the present invention may be adapted for use in the separation or sorting of different particles types which are capable of adhering or binding to the metal grains, metal particles or metal crystals which are formed on the surface of the light sensitive layer.

The method may be adapted for sorting or separating, inter alia, inorganic particles, living or non-living cells (dead cells, fixed or non-fixed), such as but not limited to eukaryotic cells and prokaryotic cells, mammalian cells, cellular aggregates, various different sub-cellular organelles or sub-cellular particles, cell membranes or fragments thereof, various unicellular or multi-cellular microorganisms including, but not limited to, bacterial cells and cells of other different pathogenic organisms and non-pathogenic organisms, viruses, prions, nanobacteria, and macromolecules such as, but not limited to, DNA, RNA, various types of artificially made or naturally formed olygonucleotides, molecular probes, isolated genes, chromosomes, parts or fragments of chromosomes, single subunit or multi-subunit protein molecules, modified protein molecules, proteoglycans, glycoproteins, and the like.

Reference is now made to FIGS. 1A-1F which are schematic diagrams illustrating a particle sorting and/or separating method, in accordance with one preferred embodiment of the present invention.

FIG. 1A illustrates a substrate 2 coated with a light sensitive layer 4. The substrate 2 is preferably a flat substrate, but other types of substrates, such as but not limited to, curved substrates, stepped substrates, and other substrates having a surface which is not flat or is only partially flat may be used.

The light sensitive layer 4 has a surface 4A which is in contact with a fluid or liquid 6 which covers the surface 4A or a portion of the surface 4A. The surface 6A schematically represents the boundary or interface between the liquid 6 and the air or gas overlying the liquid 6. The substrate 2 is preferably made from a transparent substance, such as, but not limited to glass, quartz, or a suitable plastic material, but other substances or compositions may also be used. However, the material from which the substrate is made may also be opaque, or partially opaque, depending on the specific implementation or preferred embodiment of the present invention which is being used, and on the particular type of optical system used for implementing the invention, such as but not limited to, in optical systems using epi-illumination or reflected light, as is disclosed in detail hereinafter.

The substrate 2 (only a portion of which is illustrated in FIGS. 1A-1F), may be a part of a suitable member, such as but not limited to, a microscope slide (not shown), a Petri dish (not shown), an open container or vessel (not shown), or a covered container or vessel (not shown), or the like, depending on the specific implementation or preferred embodiment of the invention used, as is disclosed in detail hereinafter.

The light sensitive layer 4 may be any suitable type of suitable light sensitive layer such as a photosensitive emulsion which includes a photosensitizable metal salt dispersed in or disposed on a suspending or supporting matrix or substance. The matrix may be, for example, gelatin, agarose, a synthetic gel or polymer, such as but not limited to polyacrylamide based matrices known in the art, a natural gel or polymer or combinations of the above disclosed substances or any other suitable type of matrix known in the art. Preferably, the light sensitive layer 4 may include a photosensitive or photosensitizable silver salt or silver halide, such as, for example, silver bromide, silver chloride, silver iodide, or the like, or mixtures of such silver halides.

However, the suspending matrix may alternatively or additionally include other silver salts or suitable salts of other metals, such as, but not limited to light sensitive salts or complex salts or other light sensitive compounds of the following metals: Au (gold), Pt (platinum), Pd (palladium), Ni (nickel), Cu (copper), Re (Rhenium), Os (osmium), Ru (ruthenium), and Ir (Iridium), which may be photosensitized and suitably developed to form grains, or crystals or particles of the selected metals to which some of the particles to be separated may adhere or bind. For example, $K_2[Au\,Cl_4]$, $K_2[Au\,Cl_6]$ may be used as well as various light sensitive complexes or compounds of Re, and the like. It may also be possible to use mixtures of two or more different metal containing light sensitive compounds, in the methods and devices of the present invention.

The light sensitive layer 4 may also include one or more photosensitizing substances, as is known in the art, for modifying the light sensitivity of the emulsion or the layer 4, or to modify the sensitivity of the layer 4 to light having a selected or desired wavelength range. The light sensitive layer 4 may also include additional substances or compounds for controlling the properties of the metal grains or metal particles or metal crystals which are formed by developing the photosensitized metal salt (grain modifiers), as is known in the photographic art.

It is noted that the details of making, using and developing photosensitive emulsions, with or without such photosensitizing substances and grain modifiers are well known in the art, are not the subject matter of the present invention, and are therefore not disclosed in detail hereinafter, with the exception of the details described hereinbelow with respect to the exemplary experiments performed.

It is noted that care should be taken in the selection or the use of such photosensitive emulsions, to ensure that the emulsion is suitable for the specific application used. For example, when the method is implemented for sorting or separating living cells for the purpose of culturing or growing or proliferating the separated cells, the photosensitive emulsion, or the light sensitive layer 4 should not contain any substances which are lethal to the cells, or which may undesirably affect or modify the viability, or the proliferative properties, or the differentiation properties and capacities of the separated or sorted or isolated cells.

However, the presence of certain toxic substances or substances which may undesirably modify cell properties may be tolerated in applications of the method of the present invention if the time of exposure of the cells to such substances is sufficiently short, so as to prevent undesirable effects which may interfere with the separation itself or with the viability or proliferative or differentiation properties of the separated or sorted or isolated cells.

The light sensitive layer 4 may also be any suitable photographic emulsion, or photosensitizable emulsion which is capable of being exposed to suitable types of light and developed to form silver grains or silver grains or silver crystals in the emulsion and on the surface of the emulsion.

Two different cells (or particles) 8 and 10 are illustrated as being in contact with the surface 4A of the light sensitive layer 4. The cells 8 and 10 and the layer 4 are immersed in or covered with a suitable liquid 6 (it is noted that for the sake of clarity of illustration, only a part of the layer of liquid 6 is illustrated in FIGS. 1A-1F). In cases in which the cells 8 and 10 are viable cells, the liquid 6 may typically be a physiological solution or medium adapted for maintaining the viability of the cells 8 and 10 at least for the duration of the separation or sorting procedure disclosed herein, or for longer time periods. For example, the liquid 6 may be phosphate buffered saline (PBS), or any other suitable physiological solution, or similar medium, known in the art.

The liquid 6 may include a suitable developer therein. Alternatively, a suitable developer may be added to the liquid 6 at a later stage of the procedure as disclosed in detail hereinafter.

The developer may be any suitable developer, or developing agent or developing substance, or developing composition which is adapted for developing suitably photosensitized metal salt or metal salts included in the layer 4. In the cases in which the cells to be separated or sorted are viable cells, the composition of the developer is such that it will not substantially affect the desired properties of the cells such as the cells' viability, proliferative properties and functionality.

The cells 8 and 10 may be brought in contact with the surface 4A of the layer 4 by covering the layer 4 with an amount of the liquid 6 in which the cells 8 and 10 are suspended or contained and allowing the cells 8 and 10 to sediment or settle to the surface 4A, either by gravity alone or by centrifugation of the entire substrate 2, or the slide or vessel or container or other member (not shown) which comprises the substrate 2, or by using any other suitable type of method for assisting or accelerating the sedimentation of the cells 8 and 10, such as for example, by changing the ionic strength or the pH of the solution in which the cells or particles are suspended by adding suitable salt solutions or buffer solutions, or by using electrophoresis, by attracting the cells or particles to the surface using suitable electrical currents passed between the layer 4 or the substrate 2 and a suitable electrode (not shown) immersed in the liquid 6, or by any other suitable method known in the art for accelerating or assisting the sedimentation of cells (including living or dead cells) or other particles.

It is noted that, while the method is schematically illustrated with respect to only two cells 8, and 10, the method may be applied for sorting and or separating a plurality of cells (not shown) and is suitable for sorting and/or separating large populations of cells of different types, as is disclosed in detail hereinbelow. The cell 8 is different than the cell 10. The cell 8 may be distinguished from the cell 10 based on a detectable difference of at least one characteristic or property of the cells. For example, the cells 8 and 10 may be distinguished from one another on the basis of their shape, dimensions, color, optical density, structural or other morphological features, the presence or absence of a cell nucleus or differences in the shape of the nucleus, the presence or absence of sub-cellular components or compartments such as vacuoles, motile organelles such as a flagellum, cilia, and the like, or based on any other suitably detectable difference or differences in properties between the cells.

The desired type of cell is then identified based on the detectable difference between the cells 8 and 10. In the specific, non-limiting, example illustrated in FIGS. 1A-1F, the cell 8 has a smooth surface while the cell 10 has a crenate or "bumpy" surface which is detectably distinguishable from the smooth surface of the cell 8. Another property that distinguishes the cell 8 from the cell 8 is that the cell 8 has a nucleus 8A therewithin, while the cell 10 does not have a nucleus. It is noted that, while the presence of more than one detectable difference in properties between the cells 8 and 10 may assist or enhance or improve the distinguishing between the different cells, or the identification of a desired type of cell, generally, the method may be implemented based on a detectable difference in a detectable difference in a single property or single characteristic of the cells 8 and 10.

In accordance with one preferred embodiment of the present invention, the identification of a selected or desired type of cell, such as for example the cell 8 may be visually performed. For example, the substrate 2 may be a part of a microscope slide (not shown in FIGS. 1A-1F) which is visually inspected using an appropriate microscope (not shown), or other suitable microscopy devices (not shown), and the like. The user of the microscope visually observes the cells 8 and 10 and visually identifies the cell 8 based on one or more of the different property differences between the cell 8 and the cell 10. After the cell 8 is identified as the desired or selected cell (FIG. 1A), the user locally exposes a portion of the light sensitive layer 4 in the vicinity of the cell 8 to light by directing a beam of light 12 (FIG. 1B) to a portion of the layer 4 or the surface 4A of the layer 4, directly under the cell 8 or in the vicinity of the cell 8. The light beam 12 is produced by a light source 18. The light beam 12 photosensitizes the metal salt (such as, for example, silver bromide as disclosed in detail in the examples disclosed hereinafter) included in the layer 4. Once the light beam 12 photosensitizes the metal salt included in the layer 4, the developer included in the liquid 6 develops the photosensitized metal salt included in the layer 4 to form metal grains 16 (see FIG. 1C). The metal grains 16 may be grains of metal or metal crystals or any other form of metal particles which may be formed when a photosensitized metal salt is reacted with a developer as is known in the art. For example, in a preferred embodiment of the present invention in which the metal salt is silver bromide, the metal grains 16 are the silver metal grains or grains or crystals formed when the photosensitized silver bromide (not shown) included in the layer 4 are developed (for example, by being chemically reduced) by the developer.

After or during the formation of the metal grains 16 in the vicinity of the cell 8 by the development of the photosensitized region or regions of the light sensitive layer 4, the parts of the cell 8 which are in contact with the metal grains 16 interact with the surface of the metal grains 16 and become bound to or may adhere to parts of the surfaces of the metal grains 16. Thus, the cell 8 adheres to or becomes effectively attached to the layer 4. In contrast to the cell 8 which becomes attached to the layer 4, the cell 10 is not attached to the layer 4 because the region of the layer 4 which underlies the cell 10 has not been substantially illuminated by the light beam 12 and therefore has not been photosensitized and no metal grains were developed or formed in the region or parts of the layer 4 which underlie the cell 10. The separation of the cells may now be performed by suitably washing the layer 4 in such a way that the cell 10 which is not attached to the layer 4, is removed or carried away by a suitable washing liquid (not shown) applied to the layer 4 while the adhered cell 8 remains attached to the layer 4. The layer 4 may be washed out by additional amounts of a liquid having the same composition as the liquid 6 (preferably without the developer, to minimize the time of exposure of the cells to the developer). Alternatively, the washing may be performed by a liquid having a different composition than the liquid 6. The washing step washes the surface 4A of the layer 4, carries away the cell 10 and leaves behind the cell 8 adhered to the layer 4.

Figure 1B:
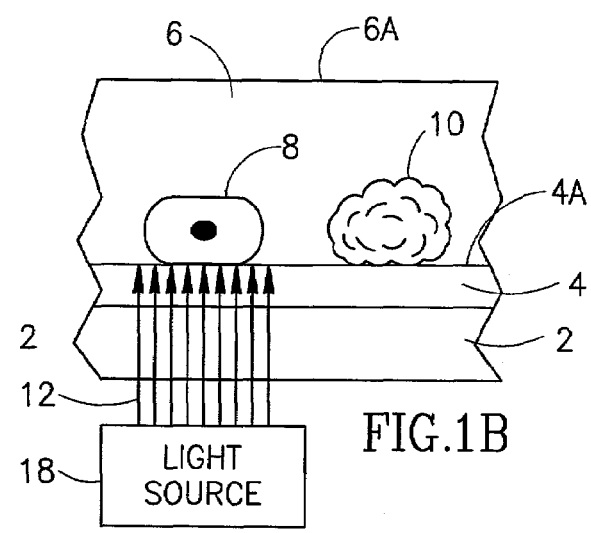
Figure 1C:
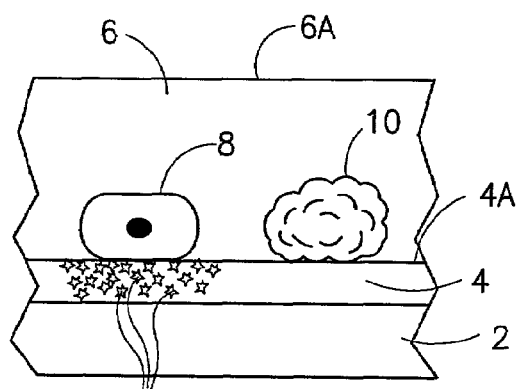
Figure 1D:
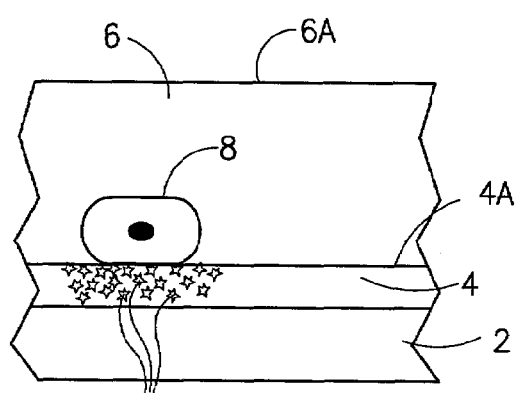

FIG. 1D illustrates the layer 4 and the cell 8 adhering to the metal grains 16 after the washing. The cell 10 is not illustrated in FIG. 1D since it has been washed away by the washing step. The washing liquid or fluid (not shown) including the cell 10 (not shown) may be collected for further utilization. Alternatively, the washing fluid may be discarded.

It is noted that the washing conditions may have to be suitably adapted to ensure a good separation of the cells. Thus, the washing parameters, such as but not limited to, the composition of the washing fluid, the total amount or volume of the washing fluid used, the washing rate or flow rate of the washing fluid (expressed as the volume of washing fluid per time unit), the degree of turbulence in the washing fluid, and other washing parameters, may have to be controlled to ensure that all or most of the non-adhering cells (such as for example the cell 10 of FIG. 1C) will be removed from the layer 4 in the washing step.

Figure 1E:
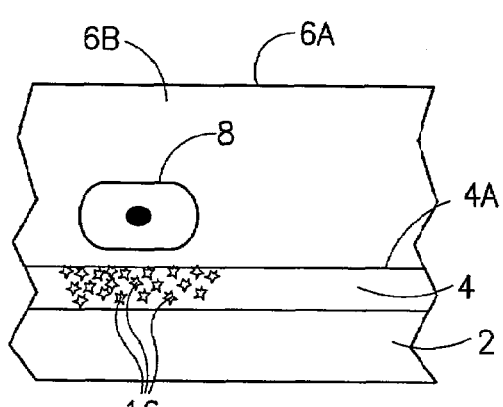

After the washing is completed, the cell 8 may be recovered by suitably dissociating it from the layer 4. For example, a fluid 6B (FIG. 1E) such as, but not limited to, a solution containing a proteolytic enzyme, such as, for example, trypsin, pepsin, papain or other suitable proteolytic enzymes known in the art, may be added on the layer 4. The layer 4 and the cells adhering to it (such as, but not limited to the cell 8), may then be incubated with the fluid 6B for a time period sufficient for the dissociation of the cell 8 from the metal grains 16 and from the layer 4 in which the grains 16 are included. The dissociation of the adhered cell by the proteolytic enzyme are believed to occur via the degradation or modification of the surface protein molecules on the surface of the cell 8 or on the surface of other cells or particles (not shown in FIG. 1E) adhering to the metal grains 16. As a result, the cell 8 may dissociate from the layer 4 (as illustrated in FIG. 1E), alternatively, the bond between the cell 8 to the metal grains 16 may be sufficiently weakened to enable the cell 8 to detach from the layer 4 with subsequent washings which removes the cell 8 or any other cells (not shown) which were previously immobilized on the layer 4 as disclosed hereinabove. The cell 8 or other cells (not shown) which were dissociated and washed out from the layer 4 may now be collected or harvested in the washing fluid. Alternatively, the cell 8 may be collected under visual control by observing the layer 4 under the microscope and using a suitable micro-pipette (not shown) or another suitable suction device to harvest the cell 8 or other cells that need to be collected.

Briefly turning to FIG. 1E, the cell 8 is shown as being dissociated from the layer 4 and the metal grains 16 included in the layer 4 and is floating free in the fluid 6B. If the cell 8 is required for further use, and if it includes proteinacious material, the proteolytic enzyme may have to be neutralized by means known in the art, such as, but not limited to, the addition of serum or a suitable tissue culture medium, followed by a wash, or by any other suitable neutralizing or washing method known in the art. Similar neutralization and/or washing methods may be used when the separated or sorted particles are of biological origin or contain proteinacious materials, such as but not limited to when the particles to be separated are bacteria, subcellular particles such as, but not limited to mitochondria, cell membranes or fragments thereof, genes or fragments thereof, or the like.

It is noted that while the light beam 12 of FIG. 1B is shown as directed towards the layer 4 by passing through the substrate 2, other alternatives may be used in which the light beam is directed at the light sensitive layer 4 from other directions, as is disclosed in detail hereinafter.

The beam of light 12 may be applied to the layer 4 or to the surface 4A thereof by a suitable light source 18. The light source 18 may be any suitable light source configured to direct a beam of light at a selected portion of the layer 4 or the surface 4A thereof, as disclosed in detail hereinafter. Briefly, the light source 18 may be integrated within the optical system of the microscope. Thus, for example, the light source 18 may be a source of visible light, coherent light, incoherent light, laser light, polychromatic light, monochromatic light, polarized light, non-polarized light, infrared light, ultraviolet light, or various different suitable combinations of types of light, depending, inter alia, on the type and degree of photosensitivity of the photosensitive material included in the layer 4, the specific types of cells to be sorted and optical and spectral properties thereof, the light tolerance of the cells to be sorted, and other different optical, design and manufacturing considerations. Preferably, but not necessarily, in a system having an integrated light source, the beam of light may be directed at a portion of the layer 4 or of the surface 4A thereof through the objective lens (not shown) of the microscope (not shown) as is known in the art. For example, the light source 18 may be a laser light source and the beam of light 12 may be a laser beam generated by the laser light source integrated with or operatively coupled to the optics of the system or microscope. Alternatively the light beam 12 may be a beam of incoherent light provided by a light source such as, but not limited to a suitable incandescent filament lamp (not shown), a suitable halogen lamp (not shown), a light emitting diode (LED) (not shown), a UV light source (not shown) such as, but not limited to a mercury lamp (not shown) or a deuterium lamp (not shown), a light source optically coupled to a suitable filter (not shown) or to a suitable monochromator device (not shown) for providing polychromatic light with a wide or narrow wavelength range, a suitable lamp emitting a preferred combination of light wavelengths, such as but not limited to a sodium vapor lamp (not shown), a suitable fluorescent light lamp (not shown), a flash lamp (not shown) or gas discharge lamp (not shown), such as but not limited to a xenon flash lamp, a source of infra-red radiation (not shown), or generally any other suitable type of light source known in the art which produces or emits light or electromagnetic radiation which is suitable for photosensitizing the metal salt included in the layer 4.

Alternatively, the light source 18 may be a separate light source which is not optically coupled or only partially optically coupled to the optics of the microscope or optical system being used, and which can controllably direct a beam of light 12 at a portion of the layer 4 or of the surface 4A thereof. For example, the system may include an optical fiber (not shown) which is suitably optically coupled to any of the light sources disclosed hereinabove (not shown) and which may be controllably moved or adjusted to direct a light beam 12 towards a desired portion of the layer 4 or the surface 4A thereof. The optical fiber may also be coupled to one or more suitable optical elements, such as, but not limited to, a micro-lens or other suitable beam collimating optical elements for collimating the light exiting the optical fiber such that the light beam 12 exiting the optical elements is suitably collimated to enable the directing of light to a selected portion of the layer 4 or the surface 4A.

Alternatively, the separate light source may be any other suitable light source known in the art, and may include any optical elements known in the art which are capable of controllably directing a beam of light at a selected portion of the layer 4 or the surface 4A thereof, or of suitably exposing to light a selected portion of the layer 4 or of the surface 4A of the layer 4.

The optical fiber or other separate light source capable of controllably producing and directing light, may direct the light beam 12 at the layer 4 from underneath the substrate 2 as is illustrated in FIG. 1B. For example, the optical fiber may be positioned under the substrate 2 and directs the light beam 12 through the substrate 2 towards a portion of the layer 4, as is illustrated in FIG. 1B. In another non-limiting example, the optical fiber my be separately and controllably moved to direct a light beam 12 through the condenser (not shown) of the microscope, and the condenser directs the light beam 12 through the substrate 2 towards a portion of the layer 4 as is illustrated in FIG. 1B.

Figure 1F:
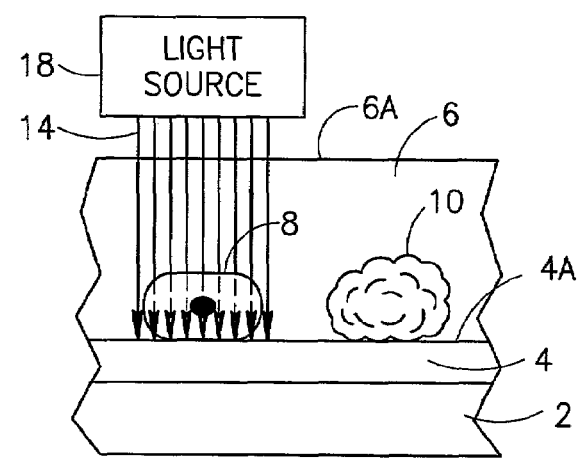

Briefly turning to FIG. 1F, the controlled localized photosensitization of a portion of the layer 4 or of the surface 4A may be performed by a light beam 14 produced by a light source 18 which may be directed at the surface 4A of the layer 4 from the side facing the surface 4A (from "above" the surface 4A). This may be the case, for example, when the microscope or the optical system used has an "inverted" configuration, such as in inverted microscopes known in the art and used, inter alia, in tissue culture examination, fluorescence microscopy applications, and various other microscopy applications. In such a case, the light source 18 (such as for example an optical fiber or other suitable light source) which produces the light beam 14 may be positioned above the surface 4A, preferably, but not necessarily within the fluid 6. However, the light source 18 or the light producing end (not shown) of the optical fiber or the other light source (not shown), may also be positioned above the surface 6A. The surface 6A schematically represents the boundary between the liquid 6 and the air or gas above it.

It is noted that directing the light beam 14 from the side facing the surface 4A of the layer 4 may be typically implemented in cases in which the particles are at least partially transparent to at least some of the wavelengths of light included in the light beam 14, such that a sufficient intensity of light passes through the particle (such as for example, through the cell 8 of FIG. 1F), to sufficiently photosensitize enough of the metal salt underlying the cell 8 or in contact therewith, to ensure the subsequent immobilization of the particle on the layer 4 after the development of the metal grains.

It is further noted that, while the optical system or microscope used for implementing some preferred embodiments of the present invention may use trans-illumination of the cells 8 and 10, or of other particles (not shown) which are to be sorted or separated, other different methods of visualization or different methods of illumination may be used for visualizing and identifying the cells or particles to be sorted. For example, among the methods and techniques which may be used to visualize and/or identify or distinguish different cells or particles are dark field illumination, epi-illumination, phase-contrast microscopy, differential interference contrast microscopy (DIC), polarization microscopy, multi-spectral or hyper-spectral microscopy involving the acquisition and analysis of pixel level spectrogram data as is known in the art, and any other suitable microscopy methods known in the art which may be adapted for use with the methods of the present invention.

In accordance with one preferred embodiment of the invention, if one uses epi-illumination microscopy for distinguishing and identifying different particles, the substrate to implement the substrate 2 may be opaque. In such an embodiment, the light used for visualizing the particles or cells (not shown) and the light used for photosensitizing the metal salts in the layer 4 (such as, for example, the light beam 14 of FIG. 1F) may both be directed at the layer 4 from above as is illustrated in FIG. 1F.

It is noted that the particles sorted by the method of the present invention such as but not limited to the cells 8 and 10 of FIG. 1A, should be applied to the layer 4 in a fluid having a suitable number of cell per unit volume of fluid, such that the distribution of the cells to be separated or sorted upon on the light sensitive surface 4A is a suitable spatial distribution. The mean inter-particle or inter-cell distance is preferably large enough to avoid cell aggregates (not shown) or clumps of cell (not shown) from being formed on the surface 4A of the light sensitive layer 4. For example, the distance between the cells 8 and 10 is preferably large enough to prevent the cell 10 from adhering to the metal grains 16 formed in the vicinity of the cell 8. If the cells 8 and 10 are deposited too close to each other, or if they touch each other of if one of the cells 8 and 10 is too close to the other cell, this may result in undesirable adherence of the cell 10 to metal grains formed by the illumination of the cell 8 by the light beam 12 and by the subsequent development of the sensitized region as disclosed hereinabove. Additionally, since at least some of the light of the light beam 12 may be scattered or deflected or reflected by the cell 8 and/or by the light sensitive layer 4 in the region illuminated by the light beam 12, the metal grains 16 may also be formed in regions surrounding the cell 8 which may not be directly under the cell 8. This light scattering and related optical phenomena may cause a certain spread of the region of formation of the metal grains 16 beyond the confines of the region towards which the light beam 12 was directed, even if the cross section (not shown) of the light beam 12 is smaller than the cross section of the cell 8 (A phenomenon known as fogging in the art of photography). Therefore, it is preferred to have a certain spatial separation between the cells (or particles) deposited on the surface 4A of the light sensitive layer 4, to prevent the adherence of cells which were not originally illuminated by the light beam 12, or which are undesirably disposed in contact with the metal grains.

Preferably, partial or full overlap of the cells or particles (as viewed from above or below the surface 4A) within the region illuminated by the light beams 12 or 14 should be avoided by proper adjustment of number of the cells or particles to avoid or minimize the adhering of the "wrong" cells or particles to the metal grains which are developed in the area of overlap. The number of the cells or particles is preferably optimized to avoid such undesirable adhering of cells or particles. However, the cell or particle number should be sufficiently high to allow the practical harvesting of the cells. Thus, the actual initial number of cells or particles in the fluid suspension applied to the light sensitive layer 4 may be a compromise which practically avoids contaminating undesired cells or particles, while still ensuring high yield of the required cells or particles harvested after separation. The initial number cells or particles may also depend, inter alia, on the type and optical and morphological parameters of the cells or particles, the type and optical characteristics of the light sensitive layer 4, the type, wavelength range, and intensity of the beam of light 12 or 14 used for photosensitizing the layer 4, the type and optical clarity and other characteristics of the fluid used to suspend the cells or particles, the degree of sensitivity of the light sensitive metal salt dispersed in the light sensitive layer 4, and on other different factors. It will be appreciated that for certain applications in which the isolation or separation of only a single cell or particle, or very few cells or particles is sufficient, a very low initial number of cells or particles may be utilized in implementing the method of the present invention.

It is further noted that the intensity of light of the light beam 12 or 14 should be controlled to avoid undesirable scattering and reflection of the light by different surfaces, such as, for example, the surfaces 6A and 4A of FIG. 1A, in order to reduce the amount of stray light to levels which results in acceptable sorting or separation criteria. The levels of acceptable stray light may vary, depending on the application. Thus, higher levels of stray light may be allowed in applications involving enrichment of a cell population, while low levels of stray light may be necessary for applications which require low error levels. For example, such applications may include the separation and isolation of fetal nucleated red blood cells (fNRBC) from other cells included in maternal blood, the separation and isolation of cancer cells in peripheral blood, the separation and isolation of stem cells or progenitor cells, and the like.

Figure 2:
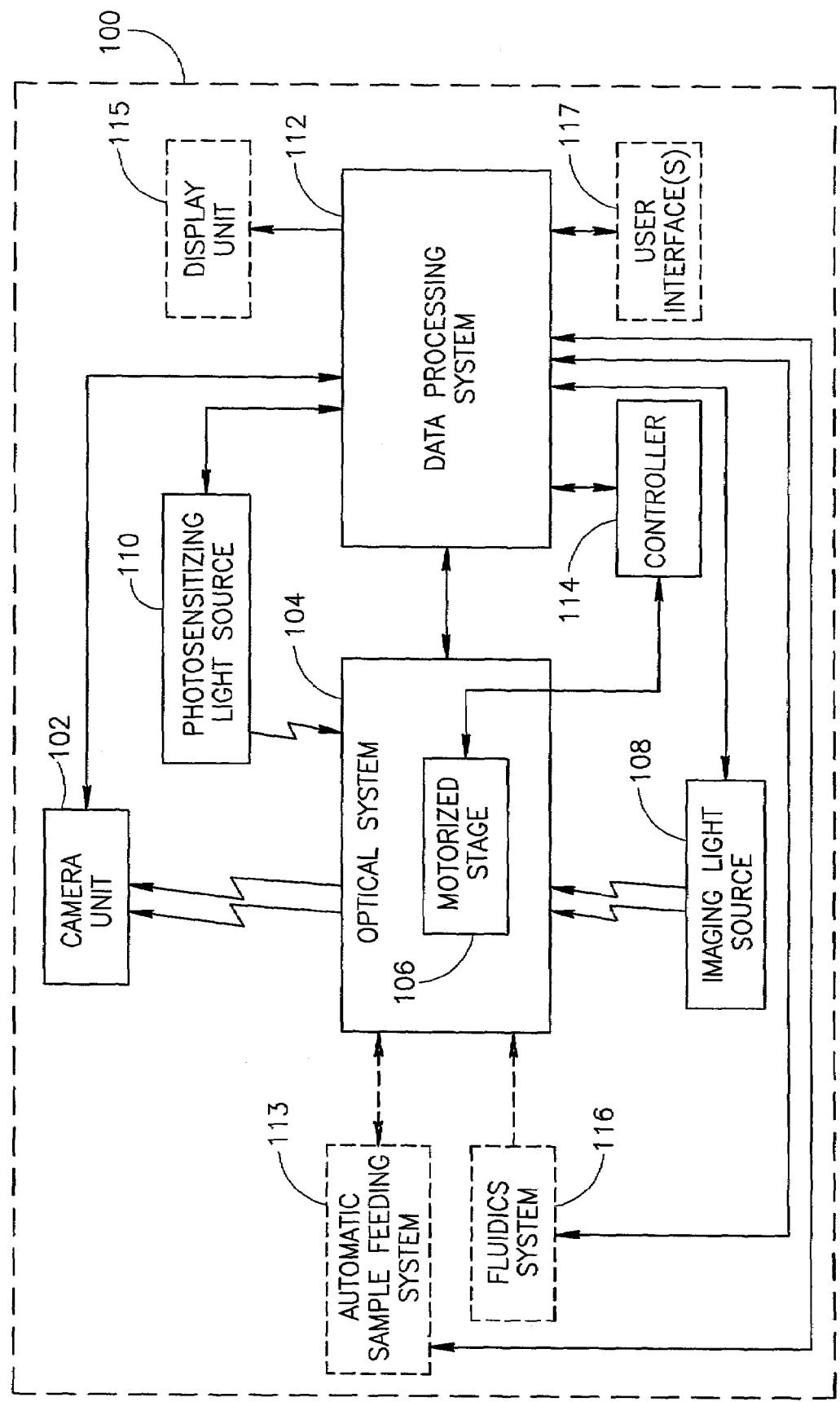
FIG. 2 is a schematic functional block diagram illustrating an automated cell sorting and/or separating system. In accordance with a preferred embodiment of the present invention.

Reference is now made to FIG. 2 which is a schematic functional block diagram illustrating an automated cell sorting and/or separating system. In accordance with a preferred embodiment of the present invention.

The cell sorting system 100 includes an optical system 104 therein. The optical system 104 may be any suitable optical system such as a regular microscope, an inverted microscope or any other type of optical system suitable for performing photo-micrography of the particles or cells to be sorted or separated. The optical system may include a motorized stage 106. The motorized stage may be an X-Y motorized stage, an X-Y-Z motorized stage or any other suitable controllable motorized stage known in the art. The motorized stage 106 may be adapted for receiving and controllably moving microscope slides, modified microscope slides, Petri dishes, or any other suitable vessel or container, or receptacle, or sample carrier for carrying a sample of the cells to be sorted or separated. The sample carrier(s) are not shown for the sake of clarity of illustration. In accordance with one non-limiting example, the sample carriers may include the substrate 2 and the light sensitive layer 4 of FIG. 1A. However, other types of sample carriers may also be used with the system 100.

The system 100 also includes an imaging light source 108 and a photosensitizing light source 110. The imaging light source 108 may be any suitable light source such as a suitable tungsten incandescent lamp (not shown), or any other suitable lamp, which is suitably coupled to a suitable condenser optics (not shown) through a suitable filter or filters (not shown). A suitable camera unit 102 is suitably optically coupled to the optical system 104. The camera 102 may be a digital camera or an analog video camera, or any other suitable type of camera capable of producing a digitizable or a digitized image of the sample within the optical system 104. The system 100 further includes a data processing system 112. The data processing system 112 is suitably coupled to the camera 102. The data processing system 112 may be any system known in the art which is capable of acquiring an images from the camera 102 and for processing and analyzing the acquired images to perform identification of the cells or other particles in the analyzed sample.

Preferably (but not necessarily), the data processing system 112 may be a computer, such as but not limited to a personal computer, a workstation, a minicomputer, a digital signal processor (DSP), a mainframe or any other suitable computer or processor or microprocessor which is capable of performing image analysis to identify different particles or cells based on the image analysis. Typically, the data processing system 112 may include a software program or programs adapted for performing particle or cell identification, as is known in the art. It is noted that, any type of image analysis may be used provided that it is capable of efficiently identifying a particular type of particle or cell based on the data of the image acquired by the camera 102 and by the data processing system 112. Exemplary systems and methods for automated microscopic detection of specific cells using image analysis methods, are disclosed in U.S. Pat. No. 5,978,497 to Lee et al., incorporated herein by reference in its entirety, U.S. Pat. No. 6,005,964 to Reid et al., incorporated herein by reference in its entirety, and in U.S. Pat. No. 6,026,174 to Palcic et al., incorporated herein by reference in its entirety. However, many other systems and devices for automated microscopic detection of specific cells or particles using image analysis methods, are known in the art. Such methods and devices may be adapted in implementing the cell or particle separation and/or sorting method of the present invention.

The details of image analysis software programs or the computing hardware which may be used therewith in the present invention are well known in the art, are not part of the present invention, and are therefore not disclosed in detail hereinafter, such software programs may be commercially available image analysis software or adaptations thereof.

The data processing system may be (optionally) coupled to a display unit 115 which may be used for displaying the acquired images and/or for displaying the image analysis results or any other required data. The display unit 115 may be any suitable type of display unit, such as but not limited to a computer monitor, a suitable cathode ray tube (CRT), a liquid crystal display (LCD) monitor, a plasma discharge display unit, a suitable light projector, or any other type of display device or display unit known in the art.

The data processing system 112 may be (optionally) coupled to one or more user interface 117 which may be used for feeding data or commands to the data processing unit 112, as in known in the art. The user interface(s) 117, may include but are not limited to, a keyboard, a keypad, a mouse, a light-pen, a touch sensitive screen, a graphic tablet, or any other suitable pointing device or data entry device, or other user interface device, known in the art. Thus, the user may used one or more of the user interface(s) 117 for operating and/or controlling the operation of the entire system 100, and also for entry of sample associated data, such as but nit limited to, patient identification data, or the like.

The data processing system 112 is suitably coupled to a controller 114. The controller 114 may be suitably coupled to the motorized stage 106 for controlling the movement of the motorized stage 104, as is known in the art. The data processing system 112 is suitably coupled to the imaging light source 108 and to the photosensitizing light source 110 for controlling the activation and the inactivation of the light sources 108 and 110 and/or for controlling the switching on and off of suitable shutters (not shown) for enabling or blocking, respectively, the passage of light from the light sources 108 and/or 110 through the optical system 104.

The imaging light source 108 is suitably optically coupled to the optical system 104 to provide light for imaging the samples carried in or on the microscope slides (not shown). The spectral characteristics and/or the intensity of the light produced by the light source 108 may be adapted such that the light is suitable for performing imaging of the sample (not shown) to be imaged without photosensitizing the photosensitizable metal salt (such as but not limited to the silver halide included in the light sensitive layer 4 of FIG. 1A).

Thus, in accordance with one non-limiting example of the present invention, the light source 108 may include a white incoherent light source, such as for example a quartz halogen lamp (not shown) coupled to a suitable bandpass optical filter (not shown) which passes only red light having a wavelength range to which the light sensitive layer 4 (of FIG. 1A) is not sensitive. Thus, the image acquisition of the particles or cells to be sorted or separated may be performed based on pattern recognition algorithms adapted for identifying the particles or cells based on the images acquired using the bandwidth limited red light provided by the light source 108.

The photosensitizing light source 110 is suitably optically coupled to the optical system 104 for providing light capable of photosensitizing the light sensitive layer 4 covering the substrate 2 (of FIG. 1A). For example, if the light sensitive layer 4 of FIG. 1A is not sensitive to the red light of the bandwidth used in imaging, but is sensitive by blue light, the photosensitizing light source 110 may include a solid state diode laser source (not shown in detail) producing a beam of blue light. The diode laser may be suitably optically coupled to the optical system 104 as disclosed in detail hereinafter.

The system 100 may (optionally) further include an automatic sample feeding system 113. The sample feeding system 113 may be an automatic slide feeder mechanism (not shown in detail) or any other suitable feeding mechanism for suitably feeding sample carriers (not shown), or sample receptacles (not shown) through the system, known in the art.

In operation, the sample feeding system 113 may position the slides or other sample carriers on the motorized stage 106 for performing the image acquisition and the data processing for identification of a specific type of desired cells (or particles). After the processing of the image data by the processing system 112. The processing system 112 sends suitable control signals to the controller 114 for moving the motorized stage 106 such that one of the identified cells is positioned at a specified position in the field of view of the optical system. Preferably (but not obligatorily), the identified cell or particle (not shown) is positioned at the optical center of the field of view as is disclosed in detail hereinafter. The data processing system 112 then sends suitable control signals to the photosensitizing light source 110. The photosensitizing light source 110 exposes the region of the light sensitive layer 4 (best seen in FIG. 1A) near or about or in the vicinity of the identified cell or particle (not shown) to photosensitizing light (blue light in the case of the non-limiting example disclosed hereinabove). After a suitable dose of photosensitizing light has been delivered, the data processing system 112 controls the motorized stage 104 to move the next identified cell or identified particle into the optical center of the field of view and again activates the photosensitizing light source 110 for photosensitizing the region of the light sensitive layer 4 about or near the next identified cell or particle. These steps are repeated until the layer 4 has been photosensitized about or near a desired number of identified cells or particles, or about or near all of the identified cells or particles. The photosensitized regions may be developed by a suitable developer as disclosed hereinabove, by a developer present in the solution in which the cells or particles are contained or, alternatively, by adding a suitable developer solution to the sample carrier after the photosensitizing exposures are completed. After or during the development of the silver grains (or other metal grains as disclosed in detail herein), the identified cells or particles will adhere to the silver grains as disclosed in detail hereinabove causing the identified cells or particles to become immobilized on the layer 4.

The system 100 may (optionally) further include a fluidics system 116. The fluidics system 116 may include suitable fluidics elements for controllably adding or removing fluids to the sample carriers (not shown). If a developer is not initially included in the solution including the sample cells or particles, the fluidics system 116 may add a suitable developer solution to the samples for performing the development of the photosensitized regions of the layer 4. The fluidics system 116 may also (optionally) apply a suitable one or more doses of a washing solution (such as for example, a suitable buffer solution or physiological solution or the like) to the sample carrier for washing the non-immobilized cells, in order to separate the immobilized cells (not shown) from the non-immobilized cells (not shown).

The fluidics system may also be used for harvesting the immobilized cells or particles to complete the cell or particle separation. This may be performed by applying a suitable digesting or dissociating solution, to the sample or sample carrier for dissociating the immobilized cells from the silver metal grains of the layer 4. For example if living cells are being sorted and separated, a solution of a proteolytic enzyme (such as, trypsin or papain, or the like) may be applied to the layer 4 and to the cells immobilized thereon by the fluidics system 116. After a suitable digestion period, the cells which dissociated from the layer 4 may be harvested by automatically aspirating or otherwise collecting the solution which includes the cells. The automatic feeding system 113 may then feed a new slide or sample carrier for performing sorting on the next sample.

It is noted that, while preferably, the entire process of sorting and/or separating the cells or particles of multiple samples may be automated, it is also possible to perform only some of the steps disclosed hereinabove automatically. For example, in order to increase the throughput of the system 100, the sample carriers may be (automatically or manually) removed from the motorized stage 104 after the development is completed, and the steps of washing and/or digesting and/or harvesting may be performed off the motorized stage, either within another part (not shown) of the system 100, or by using batch processing methods of the samples.

It will be appreciated by those skilled in the art that many such modifications and variations of the method and system may be implemented in which different combinations of the steps of the method for sorting and/or separating particles or cells disclosed hereinabove may be automatically or manually performed by suitable adaptations to the various components and operating steps of the system 100 disclosed hereinabove. Such modifications are deemed to be within the scope and essential characteristics of the present invention.

The modifications may include changing the chemical composition and photosensitization characteristics of the light sensitive layer 4, with concomitant changes (if required) to the camera unit 102, to the nature of the light sources 108 and 110. For example, if the light sensitive layer is insensitive to infra red light radiation, the camera 102 may be a camera which is sensitive to infra red (IR) light. The image acquisition may thus be performed by adapting the light source 108 to be an IR light source. The photosensitizing light source 110 may then be a white light source or any other suitable coherent or incoherent, monochromatic or polychromatic light source which produces light in a wavelength range which is suitable for photosensitizing the light sensitive layer 4.

The sample carriers (not shown) may or may not be transparent to the light provided by the imaging light source 108, and/or the photosensitizing light source 110, depending, inter alia, on the particular implementation of the optical system 104, and on the direction from which the imaging light is directed towards the sample (see also the detailed discussion hereinabove with respect to the different lighting configurations illustrated in FIGS. 1B and 1F).

Figure 3:
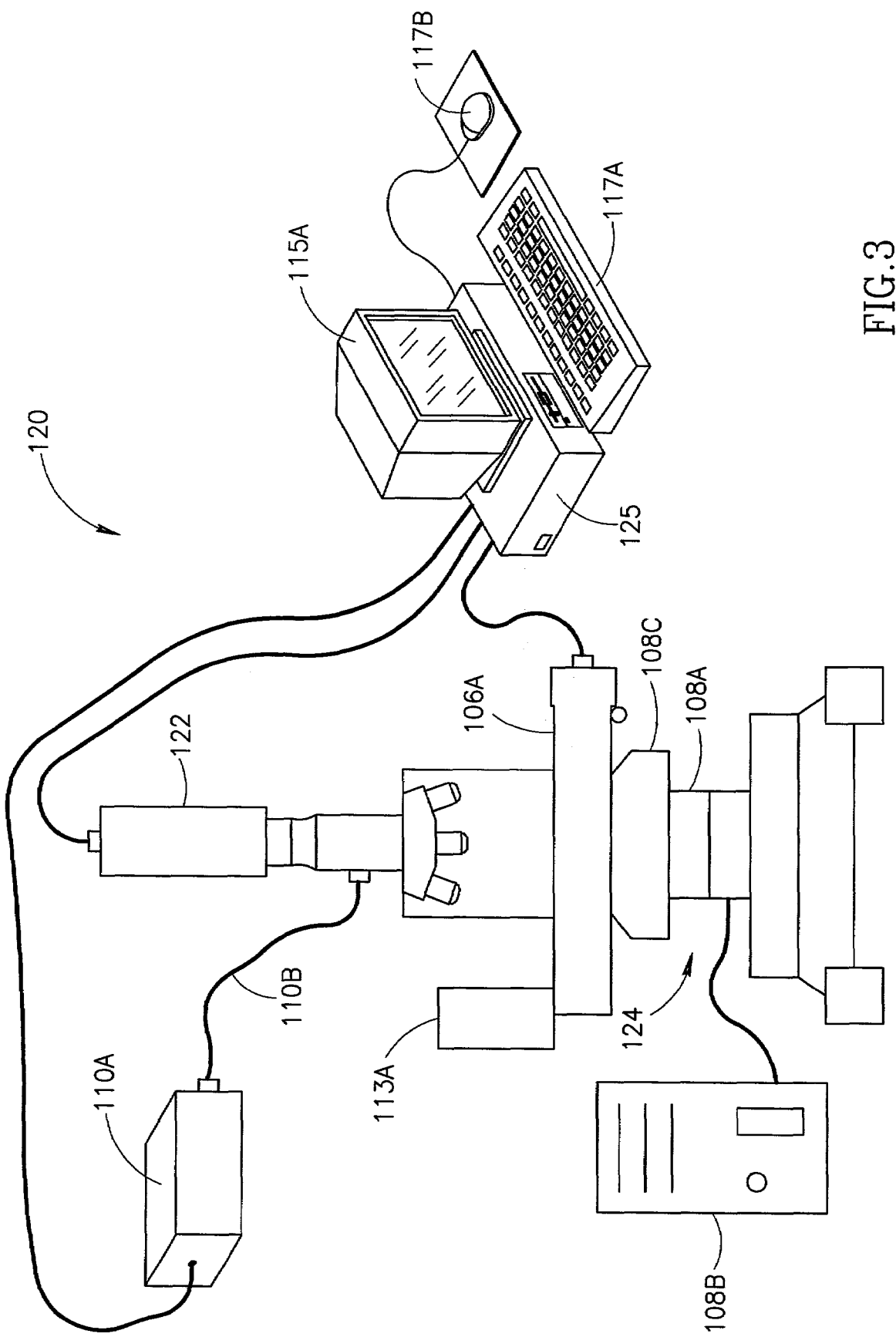
FIG. 3 is a schematic diagram illustrating an automated cell sorting and/or separating system, having a laser photosensitizing light source in accordance with a preferred embodiment of the present invention.

Reference is now made to FIG. 3 which is a schematic diagram illustrating an automated cell sorting and/or separating system, having a laser photosensitizing light source in accordance with a preferred embodiment of the present invention. The system 120 includes a microscope 124. A suitable CCD camera 122 is optically coupled to the microscope 124. The CCD camera 122 is suitably coupled to a frame grabber board (not shown) installed in a personal computer 125. The personal computer 125 may include a suitable computer display unit 115A for displaying images and data, a keyboard 117A for inputting data and commands and a mouse 117B. The personal computer 125 may include a suitable software package for performing image acquisition and for performing analysis of the acquired images to identify a selected type of cells or other particles based on one or more characteristics of the cells or particles determined from the data of the acquired images. The identification of the cells may be performed based on, inter alia, shape characteristics, color, the presence or absence of a cell nucleus, the optical density, light polarization characteristics, or any other suitable characteristic or combination of characteristics of the cells or particles obtainable or calculable from the acquired images. The system 120 includes a motorized X-Y stage 106A and an automatic microscope slide feeder 113A for automatically feeding a plurality of microscope slides (not shown) carrying the samples of the particles to be separated to be. The microscope 124 includes an integrated imaging light source 108A which includes a suitable light bulb (not shown) optically coupled to a suitable condenser 108C. The light source 108A is powered by a suitable power supply 108B. The condensed 108C includes a filter (not shown) for absorbing light and letting through only red light. The imaging is performed using the red light passing through the samples (not shown in detail). The system 120 further includes a light source 110A. The light source 110A may be a green diode laser emitting green light such as, for example, the green light emitting laser model HLMP CE23 R0000 commercially available from Agilent Technologies, Ca, U.S.A. However, any other suitable diode or other light source known in the art and having a usable wavelength range may be used. The green diode laser may be optically coupled to the optics of the microscope 124 by a suitable light fiber 110B. However, the light source 110A may be coupled to the optics of the microscope 124 using other different optical coupling configurations.

Figure 4A:
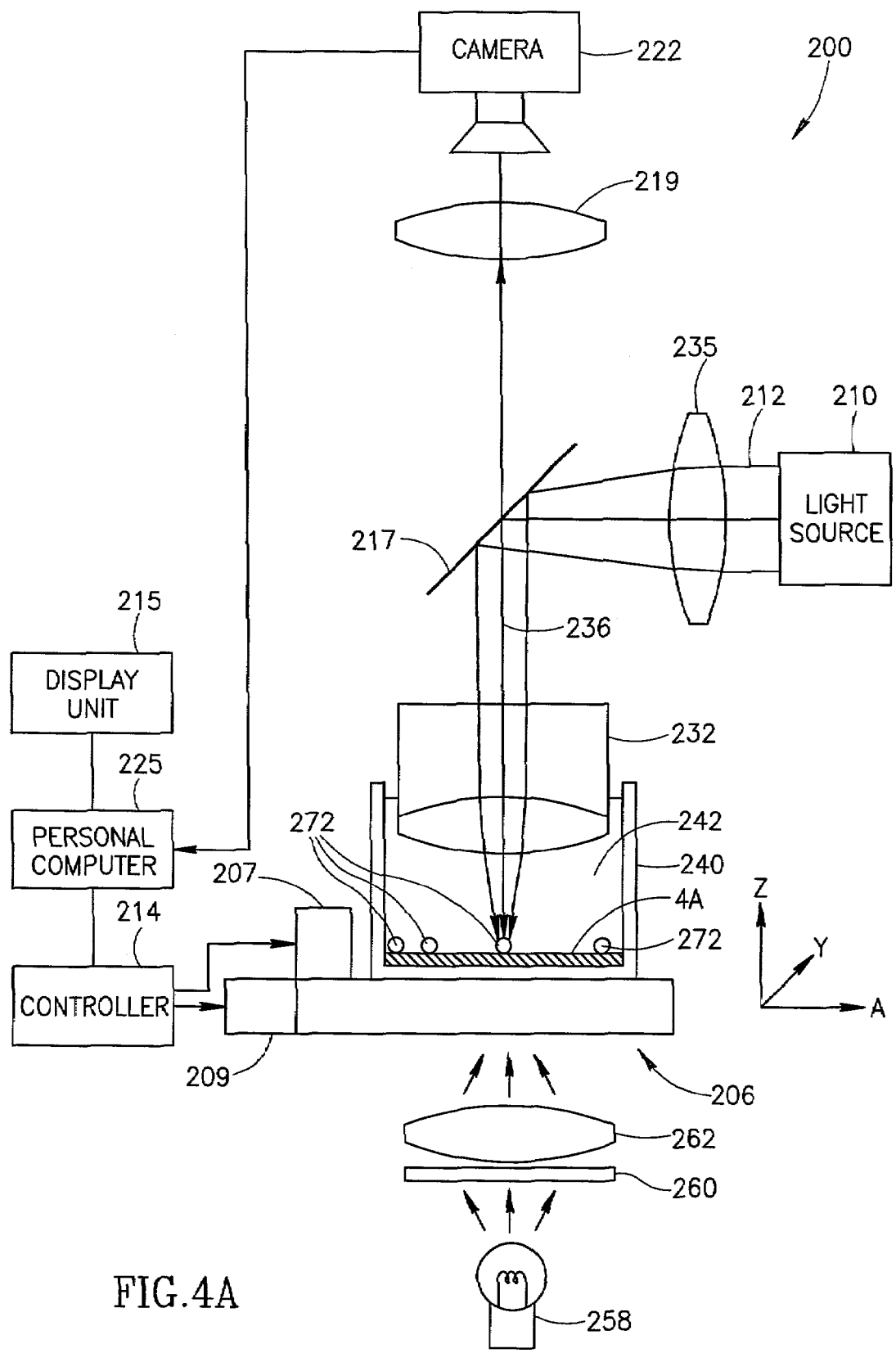
FIGS. 4A-4B are schematic diagrams illustrating the general configuration of two different optical systems which may be used in the cell sorting systems of FIGS. 2 and 3, in accordance with different preferred embodiments of the present invention.
Figure 4B:
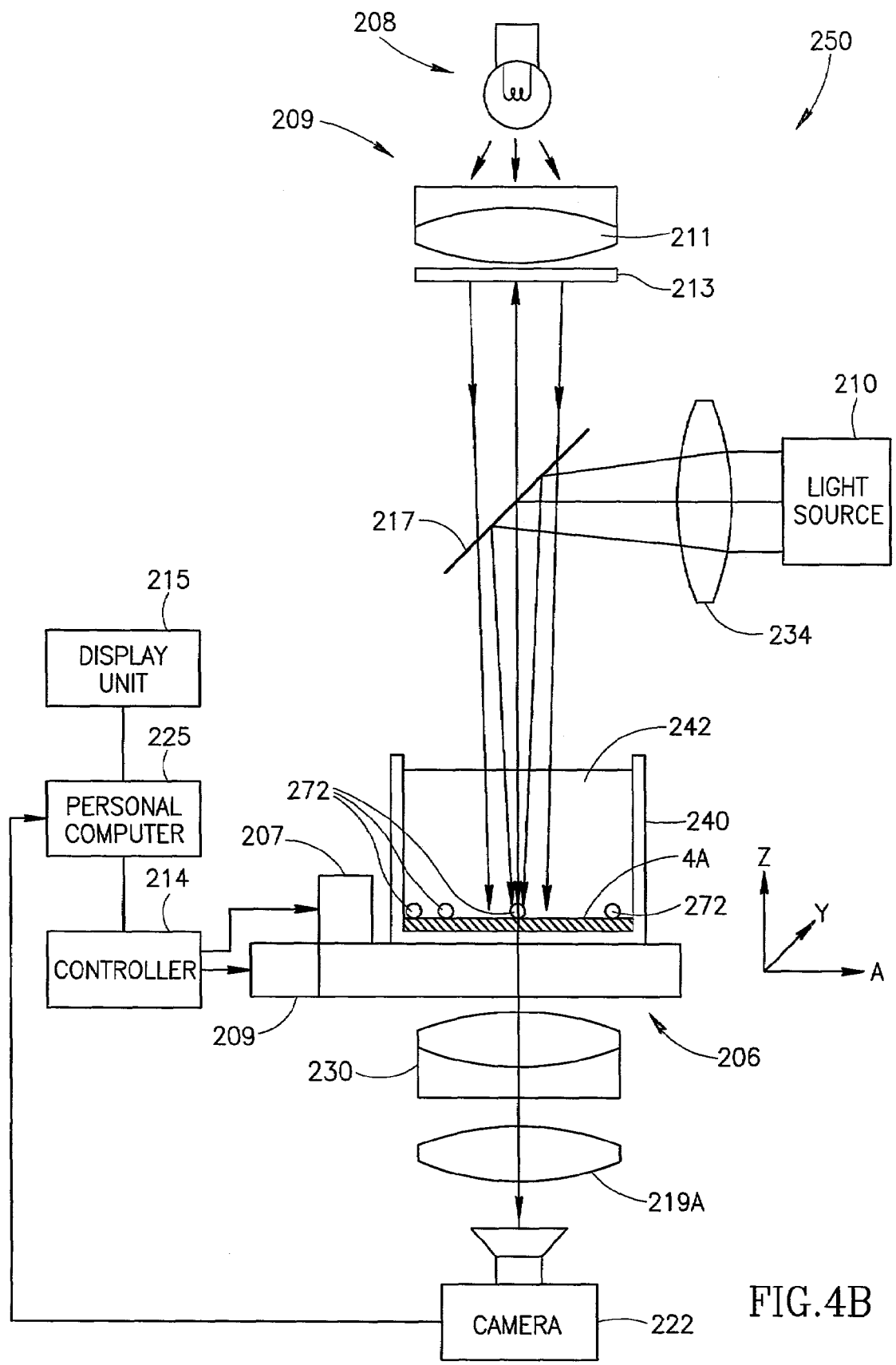

Reference is now made to FIGS. 4A and 4B which are schematic diagrams illustrating the general configuration of two different optical systems which may be used in the cell sorting systems of FIGS. 2 and 3, in accordance with different preferred embodiments of the present invention.

In the exemplary optical configuration in FIG. 4A, a system 200 for sorting or separating particles or cells has a first optical configuration. The system 200 includes a motorized stage 206 including motors 207 and 209. The motorized stage 206 may move a sample carrier 240 in three orthogonal directions (schematically represented by the three arrows labeled X, Y and Z). The motorized stage 206 may be controlled by a controller 214 which is operatively connected to as personal computer 225.

The personal computer 225 is coupled to a display unit 215. A light source 258 is optically coupled to condenser optics 262 through a suitable filter 260. The sample carrier 240 may be a small container, or a Petri dish, or a standard microscope slide (not shown), or a specially shaped microscope slide (not shown) modified to hold a liquid sample, or the like. A light sensitive layer 4A is coated or otherwise disposed at the bottom of the sample carrier 240. The sample carrier 240 may include cells 272 deposited on the light sensitive layer 4A, or other particles which are to be separated or sorted. The light sensitive layer 4A is not photosensitizable by the light which is transmitted through the filter 260. For example, if the light sensitive layer 4A is sensitive to light having a wavelength shorter than the wavelength yellow light, the filter 260 may be a red filter adapted to transmit light having wavelengths longer than the wavelength of yellow light. However, other different types of light sensitive layers may also be used and filters having other characteristics or other light sources different than the light source 258 may also be adapted for use with the specific type of light sensitive layer used.

The cells 272 are covered by a suitable physiological solution 242. Preferably, the sample carrier 240 or at least the bottom part thereof comprises a material, such as a suitable glass or a plastic which is transparent to the light which passes through the filter 260. The light sensitive layer 4A may include a matrix, such as but not limited to agarose and a photosensitizable metal salt such as but not limited to silver bromide or another silver halide or another suitable light sensitive metal salt. A suitable microscope objective 232 is positioned above the cells 272. Preferably, the microscope objective 232 is a water immersion objective which is submerged within the physiological solution 242. However, the microscope objective 232 may also be any other type of suitable microscope objective known in the art, depending, inter alia, on the type, dimensions, and other properties of the particles to be separated or sorted by the system 200.

The light passing through the microscope objective 232 passes through a beamsplitter 217 into coupling optics 219 and is imaged by a camera 222. The camera 222 may be any suitable imaging camera as disclosed hereinabove in detail for the camera unit 102 of FIG. 2. The camera 222 is suitably coupled to the personal computer 225 for transferring the acquired images to the personal computer 225. The personal computer 225 may be coupled to a display unit 215 for displaying images and data.

The system 200 further includes a second light source 210. The second light source 210 is used as a photosensitizing light source for directing photosensitizing light at a selected region of the light sensitive layer 4A, near underneath or about a selected cell of the cells 272. The beam of light 212 is collimated by a suitable collimating optical element (or elements) 235, and directed by the beamsplitter 217 through the microscope objective 232 towards a portion of the light sensitive layer 4A near or about a selected cell of the cells 272. The second light source 210 may be a source of coherent light such as but not limited to a laser light source. The laser may be any suitable type of laser device capable of producing light at a wavelength range suitable for photosensitizing the metal salt included in the light sensitive layer 4A, including but not limited to a diode laser, a gas laser (such as but not limited to a suitable Argon laser), an organic dye laser, a diode pumped laser, or any other suitable type of laser known in the art.

The second light source 210 may also be a source of monochromatic or polychromatic incoherent light of suitable intensity such as but not limited to, a suitable incandescent filament lamp (not shown), a suitable halogen lamp (not shown), a light emitting diode (LED) (not shown), a UV light source (not shown) such as, but not limited to a mercury lamp (not shown) or a deuterium lamp (not shown), a light source optically coupled to a suitable filter (not shown) or to a suitable monochromator device (not shown) for providing polychromatic light with a wide or narrow wavelength range, a suitable lamp emitting a preferred combination of light wavelengths, such as but not limited to a sodium vapor lamp (not shown), a suitable fluorescent light lamp (not shown), a flash lamp (not shown) or gas discharge lamp (not shown), such as but not limited to a xenon flash lamp, a source of infra-red radiation (not shown), or generally any other suitable type of light source known in the art which produces or emits light or electromagnetic radiation which is suitable for photosensitizing the metal salt included in the layer 4A.

It is noted that the system 200 may also be (optionally) suitably coupled to any suitable automatic or semi-automatic sample feeder (not shown in FIG. 4A) known in the art for automating the feeding of the sample carriers, such as the sample carrier 240 into the system 200, as disclosed hereinabove. Additionally, the system 200 may also (optionally) include a suitable automatic fluidics system (not shown in FIG. 4A) for automating the dispensing fluids and/or washing solutions and/or dissociating solutions and/or other reagents into the sample carriers such as the sample carrier 240 for performing some or all of the various development, washing, and particle or cell dissociating steps, disclosed in detail hereinabove. Such a fluidics system may also (optionally) be used to harvest any dissociated cells or particles, such as but not limited to some of the cells 272 by fluidically removing the solution including the separated cells or particles from the sample carrier 240 after a digesting step similar to the digesting step disclosed hereinabove for harvesting cells. The details of such a sample feeder and fluidic systems are well known in the art, are not part of the present invention, and are therefore not disclosed in detail hereinafter.

In operation, after loading (manually or automatically) a sample carrier 240 including a sample onto the motorized stage 206, the light source 258 may be turned on and the surface of the light sensitive layer 4A may be scanned by appropriately controllably moving the motorized stage 206 under the control of the personal computer 225 and the controller 214 coupled thereto. Images of the surface of the light sensitive layer 4A and of the cells 272 disposed on the surface of the light sensitive layer 4A are acquired by the camera 222 and stored in the memory (not shown) or other storage device (not shown) of the personal computer 225. The stored images are processed and analyzed by suitable image processing software operative on or embedded in the personal computer 225. A selected population of the cells 272 is identified as target cells by the image processing software based on one or more selected feature or property of the target cells which is identifiable in the images which were acquired. The coordinates of each identified target cell (not shown) are suitably stored in the memory (not shown) or other storage device (not shown) of the personal computer 225. It is noted that the exposure of the light sensitive layer 4A to the light filtered by the filter 260 does not cause substantial photosensitization of the light sensitive layer 4A due to the limited wavelength range of the light which passes the filter 260, as disclosed in detail for the filter 260 hereinabove.

After a specified number of target cells is identified, the system may start the photosensitizing step. The specified number of identified target cells may be a preset number which is preprogrammed or preset, or may be manually determined by the user, before starting the analysis. Alternatively, the photosensitizing step may be initiated after the analysis and target cell identification is completed on the entire imaged surface of the light sensitive layer 4A, or on a preset or predefined portion of the imaged surface of the light sensitive layer 4A, depending, inter alia, on the requirements of the specific application, such as but not limited to the required number of harvested cells, or the like.

In the photosensitizing step, the motorized stage 206 is moved using the stored coordinated of the identified target cells, such that a first identified target cell (not shown) is positioned at or under the optical axis 236 of the system 200. The second (photosensitizing) light source 210 may then be used to controllably apply the beam of light 212 to the region of the light sensitive layer 4A near or about the first target cell (not shown) for photosensitizing the region of the light sensitive layer 4A near or about the first target cell. The computer 225 may then control the motorized stage 206 to place another identified target cell (not shown) at or under the optical axis 236 of the system 200, and to apply the beam 212 the light sensitive layer 4A near or about the second target cell (not shown) for photosensitizing the region of the light sensitive layer 4A near or about the second target cell. These steps may be repeated until the regions of the light sensitive layer 4A near or about all or some of identified target cells are suitably photosensitized.

It is noted that the photosensitizing step may be performed by pulsing the light beam 212 for a specified pulse duration (this may be preferred when the light source 210 is a pulsable diode laser), or by suitable opening and closing a suitable shutter (not shown) included in the second light source 210 (this may be preferred when it is not desired or feasible to switch the light source 210 on and off, such as, for example, when the light source 210 is a tungsten filament lamp or a halogen lamp or a deuterium light source, or the like). The duration of the exposure of the light sensitive layer 4A to the photosensitizing light beam 212, is adapted such that effective photosensitization of the silver halide (or other light sensitive metal salt) of the light sensitive layer 4A is effected.

In accordance with one preferred embodiment of the present invention, the development of the photosensitized regions of the light sensitive layer 4A may then be performed by gently adding a solution of a suitable developer into the sample carrier 240 to develop grains of silver in the photosensitized regions of the light sensitive layer 4A as disclosed in detail hereinabove. Alternatively, In accordance with another preferred embodiment of the present invention, the physiological solution 242 may already include a suitable developer, and the development may occur during and after the illumination of the various regions of the light sensitive layer 4A by the photosensitizing light beam 212.

After the development of the photosensitized regions, the identified cells (not shown in FIG. 4A) will adhere to the grains of silver metal (or to grains of another metal, if a different metal is used) which are formed in the photosensitized and developed regions of the light sensitive layer 4A. The identified cells may therefore become immobilized on the light sensitive layer 4A as disclosed in detail hereinabove. The sample carrier 240 may then be manually or automatically removed from the motorized stage 206 for performing other steps of the cell sorting or separating procedures, such as, but not limited to the step of washing of the sample carrier 240 to remove the non-immobilized cells and/or the step of digesting (cell dissociating), and/or the step of cell harvesting, and/or the step of culturing of the separated identified cells, depending, inter alia, on the specific application.

Alternatively, if the system 200 includes a suitable fluidics system (not shown) one or more of the step of washing of the sample carrier 240 to remove the non-immobilized cells, and/or the step of digesting (cell dissociating), and/or the step of cell harvesting, and/or the step of culturing of the separated identified cells, may be automatically performed by such a fluidics system.

Turning to FIG. 4B, a system 250 for sorting or separating particles or cells has a second optical configuration, different than the optical configuration of the system 200 of FIG. 4A. The system 250 is based on an optical configuration of an adapted inverted microscope, as is known in the art. The system 250 includes a motorized stage 206 including motors 207 and 209. The motorized stage 206 may move a sample carrier 240 in three orthogonal directions (schematically represented by the three arrows labeled X, Y and Z). The motorized stage 206 may be controlled by a controller 214 which is operatively connected to as personal computer 225. The personal computer 225 is coupled to a display unit 215. A light source 208 is optically coupled to condenser optics 211 through a suitable filter 213. The sample carrier 240 may include the light sensitive layer 4A and may be implemented as disclosed in detail hereinabove.

After the light produced by the light source 208 passes through the filter 213, the filtered light passes through a beamsplitter 217, passes through the physiological solution 240 contained in the sample carrier 240, and is directed at the light sensitive layer 4A from above. A suitable microscope objective 230 is disposed under the motorized stage 206. A camera 222 may be optically coupled to the microscope objective 230 through coupling optics 219A. The camera 222 may be any suitable imaging camera as disclosed hereinabove in detail for the camera unit 102 of FIG. 2. The camera 222 is suitably coupled to the personal computer 225 for transferring the acquired images to the personal computer 225. The personal computer 225 may be coupled to a display unit 215 for displaying images and data.

The light sensitive layer 4A is not photosensitizable by the light which is transmitted through the filter 213. However, other different types of light sensitive layers may also be used and filters having other characteristics or other light sources different than the light source 208 may also be used, depending, inter alia, on the specific type of light sensitive layer used.

The system 200 further includes a second light source 210 as disclosed hereinabove. The second light source 210 is used as a photosensitizing light source for directing photosensitizing light at a selected region of the light sensitive layer 4A, near, underneath or about a selected cell of the cells 272. The beam of light 212 is collimated by a suitable collimating optical element (or elements) 234, and directed by the beamsplitter 217 through the physiological solution 242 towards a portion of the light sensitive layer 4A near or about a selected cell of the cells 272. The second light source 210 may be any types of light sources as disclosed in detail hereinabove.

It is noted that the system 200 may also be (optionally) suitably coupled to any suitable automatic or semi-automatic sample feeder (not shown in FIG. 4B), as disclosed hereinabove for the system 200 of FIG. 4A. Additionally, the system 200 may also (optionally) include a suitable automatic fluidics system (not shown in FIG. 4B)), as disclosed hereinabove for the system 200 of FIG. 4A.

Each of the optical configurations of the systems 200 and 250 illustrated in FIGS. 4A and 4B, respectively may have specific advantages. For example, the system 200 may be advantageous for separating cells or particles or subcellular organelles which may require high magnification, which may be obtained by using a high quality immersion microscope objective, to implement the microscope objective 232 of FIG. 4A. The system 250 may be advantageous for separating cells or particles which may not require high magnification, allowing the use of simpler and therefor less expensive microscope objectives to implement the microscope objective 230 of FIG. 4B.

The configuration of the system 250 of FIG. 4B has the advantage of allowing easier and simpler integration of some system components, such as but not limited to an automatic sample carrier feeding mechanism (not shown) or an automatic fluidics system (not shown) due to the relatively large distance between the condenser optics 209 and the motorized stage 206, which distance may be made be further increased by using long distance condenser optics (not shown in detail which are well known in the art of inverted microscope design.

It is noted that while the separation and sorting methods disclosed hereinabove may be well suited for applications in which the number of recovered sorted cells is not critical, such as, for example, diagnostic cell separation or the like, separation and sorting methods which are based on manual (visual) cell identification or even on higher throughput automated microscopy based systems using pattern recognition based or other cell identification methods, may not yield sufficient amounts of cells required for certain applications. It is therefore desired to have a method which may be used to separate, or sort, or purify relatively large numbers of cells.

The identification of specific types of particles or cells either visually by a trained operator or automatically by using automated image analysis systems as disclosed hereinabove may be time consuming expensive, and may have low throughput. Moreover, automated image analysis systems may be expensive, may require trained operators, and may be difficult to maintain. There is therefore a long felt need for simple, efficient, and inexpensive methods for sorting, and/or separating, and/or purifying, and/or, isolating particles or cells.

Bulk Methods for Particle Separation, Particle Sorting and Particle Purification The methods disclosed hereinafter and illustrated in FIGS. 5A-5F are based on the selective and specific binding of a particle or cell targeted "photophoric probe" to a specific cell or particle included in the mixture of cells or particles. The term "photophoric probe" is defined for the purpose of the present application as a molecule or molecules, or a multi molecular aggregate or particle which may specifically and selectively bind to one or more types of cells or particles and which may directly or indirectly be induced to emit or produce light or to induce or cause the production of light by other substance or substances or molecule(s) present in the vicinity of the photophoric probe under defined conditions.

It is noted that the photophoric probe may be a single prefabricated probe or may be sequentially constructed on the cells or particles by sequential steps of binding of multiple molecules or substances to the cells or particles (also known in the art as "sandwich" type selective labeling methods) as is disclosed in detail hereinafter.

Many different types of photophoric probes may be used as is disclosed in detail hereinafter, for example, the photophoric probes may include two-photon up-converting dyes or phosphors, or probes comprising other (non-fluorescent) light emitting molecules or moieties, such as, but not limited to the bioluminescent proteins obelin and aequorin, or chemiluminescent molecules, or enzymes that may catalyze chemical reactions which may produce substrates capable of participating in a chemiluminescent chemical reaction or capable of activating or catalysis of a chemiluminescent chemical reaction resulting with the production of light. Alkaline-phosphatase and horseradish-peroxidase are two non-limiting examples of such enzymes that are known in the art.

Reference is now made to FIGS. 5A-5F which are schematic diagrams useful in understanding a method for separating, or sorting or purifying or isolating particles or cells, in accordance with another preferred embodiment of the present invention.

Figure 5A:
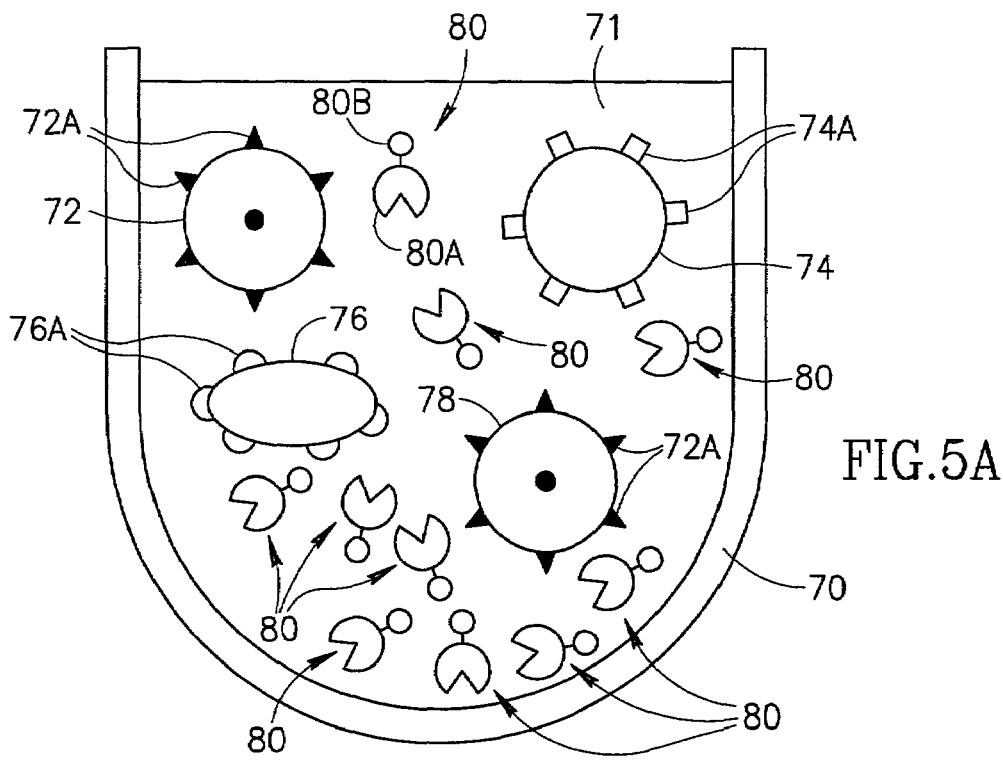

FIG. 5A illustrates a container 70. The container 70 may be any desired type of vessel or container, such as but not limited to a test tube, a flask, a bottle or any other type of suitable container or vessel known in the art. The container 70 includes a solution or fluid 71. Typically, but not obligatorily, the fluid 71 may be a physiological buffer or physiological solution or medium adapted for sustaining the viability of the cells 72, 74, 76 and 78. However, other types of suitable fluids may be used for sorting or separation of non-living or fixed cells, or for the separation of other non-cellular particles. A plurality of cells 72, 74, 76 and 78 are suspended in or dispersed or otherwise contained in the fluid 71. The cells 72 and 78 are of the same cell type. The cells 74 and 76 are different types of cells which differ from the cell type of the cells 72 and 78. The surface of the cells 72 and 78 include surface determinants 72A exposed on the surface of the cells 72 and 78. The surface determinants 72A may typically be surface proteins or surface glycoproteins or proteoglycans, or any other type of surface molecules or surface ligands which are specifically expressed on the surface of cells of the type represented by the cells 72 and 78. The surface of the cell 74 includes surface determinants 74A exposed on the surface of the cell 74 that are different from the surface determinants 72A of the cells 72 and 78. The surface of the cell 76 includes surface determinants 76A exposed on the surface of the cell 76. The surface determinants 76A are different from the surface determinants 72A of the cells 72 and 78, and are different from the surface determinants 74A of the cell 74. In the first step of the method, photophoric probe molecules 80 are added to the fluid 71. Each photophoric probe molecule 80 includes a cell targeting molecule or portion or moiety 80A which is capable of recognizing cells of the type to which cells 72 and 78 belong. Preferably, the cell targeting moiety 80A has the capability of selectively and specifically binding to cells of the type represented by the targeted cells 72 and 78.

In accordance with one preferred embodiment of the present invention which is illustrated in FIGS. 5A-5F, the cell targeting moiety 80A is an antibody molecule 80A specifically directed against the surface determinants 72A of the cells 72 and 78. However, the cell targeting moiety 80A may also be any other type of molecule or moiety which is capable of selectively and specifically recognizing the cells 72 and 78 and of binding to the cells 72 and 78, such as, but not limited to, target cell specific toxin molecules, soluble ligands that can bind to a receptor on the cell's surface, soluble receptors capable of recognizing and binding to cell-surface ligands, lectins having the capacity to specifically bind to specific polysaccharides which constitute a part of specific cell membrane glycoproteins, or the like.

A photophoric molecule or moiety 80B (FIG. 5A) is bound or linked to the antibody molecule 80A, either by covalent bonds, or by non-covalent bonds. The photophoric moiety 80B may be any suitable molecule or moiety which may be induced to emit light or to cause or induce other molecules (not shown) to emit or produce light. The photophoric moiety 80B may also be a molecule or moiety which may participate directly or indirectly in a chemical reaction which produces light. The photophoric moiety 80B may also be a molecule which may participate in a physical process which leads to the production of light quanta such as phosphorescence, fluorescence, bioluminescence luminescence, chemiluminescence, two-photon up-conversion anti-stokes up-conversion, or the like.

Figure 5B:
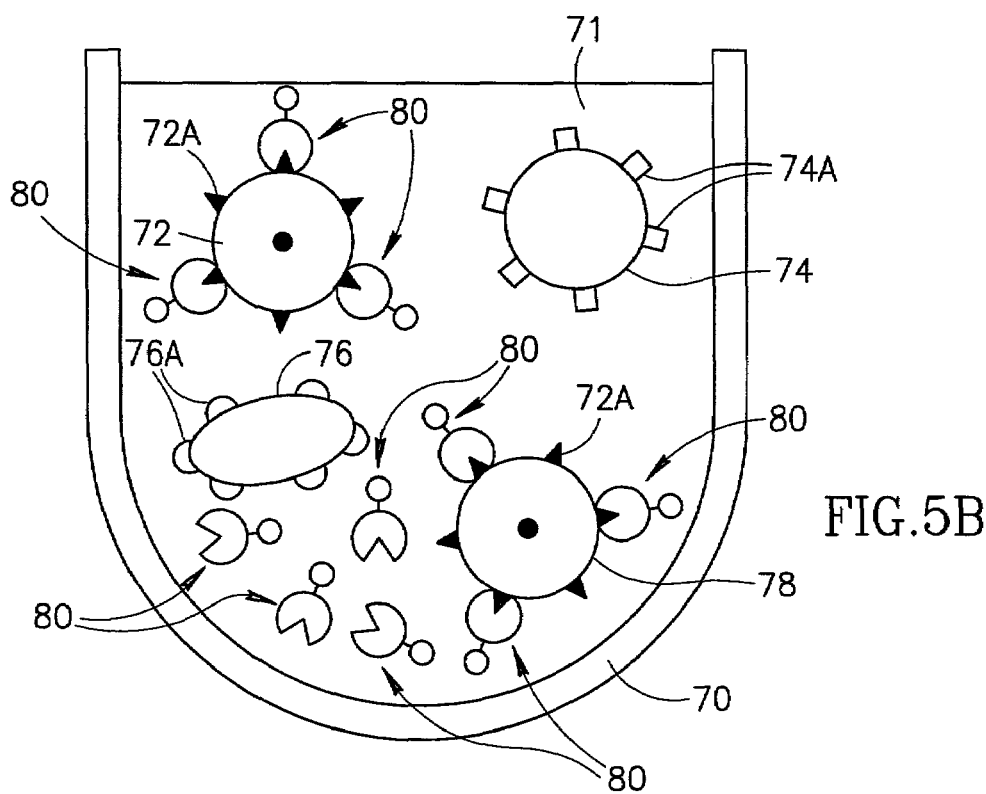

In accordance with one non-limiting example of the present invention, the photophore molecule 80B may be a molecule of the enzyme horseradish-peroxidase (HRP) which is chemically conjugated to the antibody molecule 80A. During the incubation of the mixed cells 72, 74, 76 and 78 with the photophoric probe molecules 80, the photophoric probe molecules 80 selectively and specifically bind to the determinants 72A on the surface of the cells 72 and 78 (FIG. 5B). In contrast, there is no or little non-specific binding of the photophoric probe molecules 80 to the cells 74 and 76 as schematically illustrated in FIG. 5B. In the next step of the method (step is not shown), the mixture of cells 72, 74, 76 and 78 is washed with a solution free of the molecules 80 in order to remove excess of the unbound form of these molecules. The washing may be completed by centrifugation that will sediment the cells 72, 74, 76 and 78 followed by removal of the supernatant fluid and resuspension of these cells in a fresh solution 86 that is free of the probe molecules 80.

The washing procedure may be repeated a desired number of times. In the next step, the cells 72, 74, 76 and 78 resuspended in solution 86 are transferred to another vessel 82 (FIG. 5C). The vessel 82 may be any suitable vessel or container, such as but not limited to a Petri dish, a flask, a bottle or any other type of container or vessel. The bottom of the vessel 82 is coated with, or suitably covered with a light sensitive layer 84. The light sensitive layer 84 may be similar in composition to the light sensitive layer 4 disclosed hereinabove and illustrated in FIGS. 1A-1F. The cells 72, 74, 76 and 78 are allowed to sediment to the bottom of the vessel 82 until they are in contact with the surface 84A of the layer 84, as illustrated in FIG. 5C. In the next step, a suitable mixture of reagents is added to the physiological solution 86. The reagents (not shown) may induce the production of light. In the specific non-limiting example of FIG. 5C, the mixture of reagents may include luminol (3-amino-phtalhydrazide), p-coumaric acid and hydrogen peroxide ($H_2O_2$). These reagents interact in a reaction catalyzed by the peroxidase moieties 80A, that results in the emission of light quanta or photons 88, (The photons 88 are schematically represented in FIG. 5C by the undulating arrows labeled 88).

The details of the chemical and enzymatic reactions are known in the art, and are described, inter alia, in of the book "Bioluminescence Methods and Protocols" in the series "Methods in Molecular biology™" Vol. 102, pp. 3-20, Ed. Robert a. LaRossa, published by Humana Press Inc. NJ, USA, incorporated herein by reference. It is noted that since the photophoric probe molecules 80 are bound to the cells 72 and 78, the peroxidase moieties 80B are also localized in the close vicinity of the cells 72 and 78. Therefore, the photons 88 emitted in the chemiluminescence illuminate regions of the light sensitive layer 84 which are substantially localized near the cells 72 and 78. As a result of this localized chemiluminescence, the regions of the light sensitive layer 84 underlying the cells 72 and 78 or in the vicinity thereof, are photosensitized.

In accordance with another preferred embodiment of the present invention, the efficiency of the chemiluminescent light emission may be enhanced by adding to the mixture of reagents one or more chemiluminescence enhancing substances, such as, but not limited to, orthovanadate anions, as is disclosed in detail in U.S. Pat. No. 5,492,816 to Pfefferkorn, incorporated herein by reference in its entirety. Another method for increasing luminol chemiluminescence is disclosed by Motsenbocker et al. in European Patent EP 476 35 556, incorporated herein by reference in its entirety, which may also be adapted for use in the present invention. However, any other suitable substances or methods for enhancing chemiluminescence which are known in the art may also be used with the present invention.

The advantage of using chemiluminescence enhancing methods in the method of the present invention, is that this may lead to an increase in the intensity of light produced by the chemiluminescent reaction(s) and may therefore allow shortening of the photosensitization step which may allow higher throughput due to faster sample processing.

It is noted that the type of metal salt included in the light sensitive layer 84 are selected such that the photons 88 are capable of suitably photosensitizing the metal salt. In accordance with a preferred embodiment of the present invention, the mixture of reagents added to start the chemiluminescence reaction also includes a suitable developer capable of development the photosensitized regions of the light sensitive layer 84 as disclosed hereinabove. It is noted that in this preferred embodiment, the developer is selected such that it does not undesirably interfere with the chemiluminescence reaction catalyzed by the peroxidase moieties 80B. In accordance with another preferred embodiment of the present invention, a suitable photosensitization time period may be allowed for photosensitization of the light sensitive layer 84 (in the absence of a developer), and the developer may then be added to the physiological solution 86 after the photosensitization time period. It is noted that if the latter possibility is implemented, it may be possible to use a developer which may interfere with or even completely stop the chemiluminescence reaction, since the photosensitization may be completed in the photosensitization time period. Thus, the fluid 86 of FIG. 5C may or may not include a developer in addition to the chemiluminescence reagents disclosed hereinabove. The Fluid 86A of FIG. 5D may be similar to the fluid 86 of FIG. 5C (in the case were the developer is included therewithin in addition to the chemiluminescence reagents disclosed hereinabove). If the developer is added at the end of the photosensitization time period as disclosed hereinabove, the fluid 86 of FIG. 5C does not include the developer, and the fluid 86A of FIG. 5D does include a developer. The developer develops metal grains 86 (FIG. 5D) in the photosensitized regions of the light sensitive layer 84 under the cells 72 and 78 or in the vicinity thereof, similarly to the development of the metal grains 16 of FIG. 1C.

The target cells 72 and 78 adhere to, or bind to, or suitably interact with the metal grains 86 (FIG. 5D) as described in detail hereinabove with reference to the cell 8 and metal grains 16 of FIG. 1C. The cells 72 and 78 are thus immobilized on the layer 84 due to the binding interactions between the cells 72 and 78 and the metal grains 86, as disclosed hereinabove. The next step of the method removes the cells 74 and 76 which are not immobilized on or bound to the layer 84 since no or very few metal grains 86 are formed under or in the vicinity thereof. The non-immobilized cells 74 and 76 may be removed by a suitably wash of the layer 84 with a washing fluid, such as but not limited to, a physiological solution or a suitable buffer or the like. However, other removal procedures such as substrate heating or substrate dissolution may also be used, as disclosed hereinabove.

FIG. 5E schematically illustrates the vessel 82 after the removal of the non-immobilized cells by washing. After the washing, the cells 72 and 78 remain immobilized on the layer 84 and are covered by the washing fluid 86B. At this stage the cells 72 and 78 have been isolated or separated from other cells which were initially included within the vessel 70 at the beginning of the separation or sorting procedure (such as the cells 74 and 76 of FIG. 5A). The method may also include a further step of dissociating the cells 72 and 78 from the layer 84 to enable their harvesting. This may be accomplished by any of the methods disclosed hereinabove, such as, but not limited to, proteolytic enzyme treatment by suitable dissociating enzymes, or by changing the ionic composition or strength of the fluid covering the cells 72 and 78 so that the metal grains that bind the cells to the substrate dissolves and thus detaches the cells from the substrate.

FIG. 5F schematically illustrates the cells 72 and 78 after they have been dissociated from the layer 84 by proteolytic treatment. The fluid 86C represents a physiological solution or suitable buffer solution, to which a proteolytic enzyme has been added. The proteolytic enzyme may be pepsin or trypsin or papain, or any other suitable proteolytic enzyme known in the art. The cells 72 and 78 are detached from the layer 84 and from the metal grains 86 included therein. The cells 72 and 78 may then be collected or harvested by removing them with the fluid 86C or by centrifugation, or by any other suitable harvesting method, and may be further used for culturing, proliferating, or for diagnostic tests or for any other desired purpose.

Alternatively, the cells may be further cultured in the vessel 82 by replacing the fluid 86C with a suitable growth medium, with or without a dissociation step, with or without an intervening fixing step for removing the excess of undeveloped metal salt dispersed within the layer 84, as disclosed in detail hereinabove.

It is noted that in the methods illustrated in FIGS. 1A-1F, the cell identification is done visually by an expert operator or automatically by an image processing system capable of recognizing and identifying the target cells (See FIGS. 2 and 3), and the photosensitization is performed by manually or automatically directing a light beam (such as, for example, by the light beams 12 and 14 of FIGS. 1B and 1F, respectively) to illuminate the vicinity of the identified target cell or cells (such as for example the cell 8 of FIGS. 1A and 1F). In contrast, in the method illustrated in FIGS. 5A-5F, the identification of the target cells is performed by the unattended selective and specific binding of the photophoric probe molecules 80 to the target cells (such as, for example, the target cells 72 and 78 of FIG. 5C), and the photosensitization is performed in an unattended manner by the light emitted by or in the vicinity of the photophoric probe molecules 80 which are bound to the target cells.

Thus, the method illustrated in FIGS. 5A-5F has the advantage that it may be performed in parallel on many separates samples, thus eliminating throughput bottlenecks, such as the sequential visual individual examination of the samples by an expert, or by the automated image acquisition and analysis system as disclosed in FIGS. 2, 3, 4A and 4B, and allowing a large number of samples to be processed simultaneously.

Another advantage of the method illustrated in FIGS. 5A-5F is that it does not require complicated and expensive devices, and may be performed economically and rapidly using simple and convenient equipment, such as incubators, centrifuges, flasks or Petri dishes. The cost of the photoprobes may be the major cost determining factor in performing the method of sorting or separating illustrated in FIGS. 5A-5F, allowing the use of the method in applications which are cost-sensitive and in laboratories or hospitals which lack sufficient funding or trained personnel for acquiring or operating and maintaining expensive microscopy and image analysis systems.

It is noted that the methods disclosed hereinabove and illustrated in the drawing figures may be modified and adapted, depending, inter alia, on the type of the particles to be separated or sorted, and on the availability of suitable probes with suitable selectivity and specificity of binding to the targeted particle or particles.

It is noted that, while the specific non-limiting examples of FIGS. 1A-1F and FIGS. 5A-5F, illustrate the sorting or separation or isolation of cells, such as the cells 8 and 10, and the cells 72, 78, 74 and 76, respectively, the methods and the devices of the present invention may be adapted for sorting, separating, isolating, and purifying other different types of particles. However, at least one type of the particles should be capable of interacting with the metal grains formed in or on the layer 4 by the development of the photosensitized metal salt. Thus, the methods disclosed hereinabove may be adapted for sorting, separating, isolating, and purifying, inter alia, living or non-living cells, various different sub-cellular organelles or sub-cellular particles, various unicellular or multi-cellular microorganisms, viruses, bacteria, macromolecules such as, but not limited to, DNA, RNA, various types of artificially made or naturally formed oligonucleotides, molecular probes, isolated genes, chromosomes, parts or fragments of chromosomes, single subunit or multi-subunit protein molecules, modified protein molecules, proteoglycans, and the like.

EXPERIMENTAL RESULTS

Cell Adhesion Experiments

A first set of experiments was performed to test the ability of living cultured cells to attach to silver grains developed in an agarose matrix.

Cell Preparation

Cells from a DA1 mouse lymphoma cell line were used in EXPERIMENT 1. This cell line is disclosed by Pierce et al. in an article titled "NEOPLASTIC TRANSFORMATION OF MAST CELLS BY ABELSON-MULV: ABROGATION OF IL-3 DEPENDENCE BY A NONAUTOCRINE MECHANISM", published in Cell, Vol. 41 pp. 685-693 (1985). The cells were grown in liquid RPMI growth medium, commercially available as catalogue number R-0883 from Sigma-Aldrich, U.S.A. medium including 7% heat inactivated fetal calf serum commercially available as catalogue number 04-121-1A from Biological Industries, Beit Haemek, Israel. The growth medium contained 1/400 (by volume) of WEHI-3B mouse myelomonocitic leukemia cell conditioned medium, as a source of murine IL-3. The WEHI-3B cells are commercially available as Catalogue number ACC 26 from Deutche Sammlung von Microorganismen und Celikulturen GMBH. The cells were grown to a cell density of $1 \times 10^6$ cells per milliliter. Prior to performing the experiment, the cells were harvested and washed three times in phosphate buffered saline (PBS) to remove the growth medium. The composition of the PBS was, 150 mM NaCl, 50 mM NaH$_2$PO$_4$, and the pH was adjusted to pH 7.2 with HCl. The cells were resuspended in PBS to a cell density of 5×10$^6$ cells per milliliter and the cell suspension was stored at 4° C.

Preparation of Agarose Matrix Coated Microscope Slides

An agarose matrix was prepared by dissolving agarose in a hot solution of 0.1M NaBr (sodium bromide) to form a 1% (w/v) of agarose in 0.1M NaBr. The heating was performed ion a microwave oven. Glass microscope slides were coated on one side with the hot agarose solution and allowed to cool at 4° C. for 5 minutes for solidifying the agarose matrix. The agarose matrix coated slides were then divided into two groups. The first group of slides was immersed in a solution of 0.1M AgNO$_3$ (silver nitrate) for 3 minutes to form photosensitizable silver bromide within and on the surface of the agarose matrix. The slides where then washed three times with doubly distilled water, treated with 0.1M NaBr solution for 1 minute and washed three times in doubly distilled water. This slide group is referred to as "slide group A".

The second group of slides was not treated and served as a control group which does not contain AgBr. The slides where washed three times with doubly distilled water, treated with 0.1M NaBr solution for 1 minute and washed three times in doubly distilled water. This slide group is referred to as "slide group B".

All the slides of slide group A and slide group B were stored at room temperature in a normally lighted room. Thus, the light exposed slides of the slide group A were exposed to ambient light causing a certain degree of photosensitization of the AgBr in the agarose matrix coating the slides of the slide A half strength stock solution of Kodak GBX developer in PBS was prepared from Kodak GBX liquid developer (commercially available as Catalog Number 1901859 from Kodak, U.S.A), in phosphate buffered saline (PBS). This half strength developer solution was prepared by diluting 50 milliliters of Kodak GBX developer with PBS to a final volume of one liter. This solution is referred to as "½ strength developer in PBS" hereinafter.

EXPERIMENT 1

This experiment tested the adherence of DA1 cells to an agarose matrix in the absence of AgBr, to an agarose matrix including non-developed AgBr, and to an agarose matrix including AgBr which is photosensitized and developed. All the experimental procedures for EXPERIMENT 1 were carried out under normal lighting conditions (in the presence of light).

All the slides in EXPERIMENT 1 were visually observed under an Olympus model CK40 microscope, and photographed using an Olympus model 150IK camera, both commercially available from Olympus, U.S.A.

Reference is now made to FIGS. 6A-6I which are photographs illustrating exemplary results of EXPERIMENT 1.

Figure 6A:
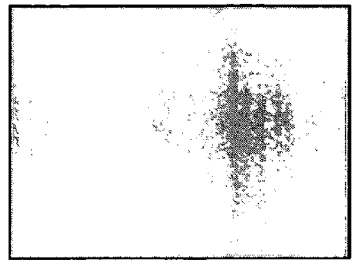
FIGS. 6A-6I are photographs illustrating exemplary results of EXPERIMENT 1 of the specification.

FIG. 6A is a photograph of a microscopic field of view of an agarose coated slide of slide group B (a slide which was not treated with AgNO$_3$).

Figure 6B:
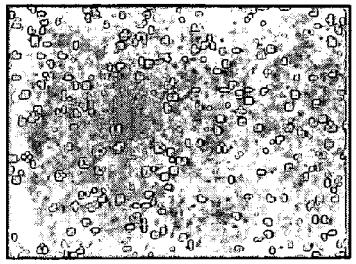
Figure 6C:
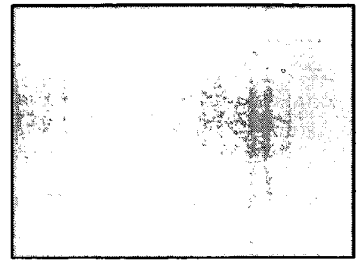

200 microliters of the cells suspended in PBS (including a total of 1×10$^6$ cells) were mixed with 200 microliters of the "½ strength developer in PBS" disclosed hereinabove to yield 400 microliters of cells suspended in developer. The 400 milliliters were then placed on the slide from slide group B. The slide was incubated for 4 minutes to allow cell sedimentation. FIG. 6B is a photograph of a microscopic field of view of the slide after this cell sedimentation occurred. The slide was then removed from the microscope stage, washed three times in PBS (total wash volume of 80 milliliter PBS) returned to the microscope stage for viewing approximately the same field of view, and photographed. FIG. 6C is a photograph of a microscopic field of view of the slide after the washing in PBS. The results indicate that DA1 cells do not exhibit significant attachment to or adhering to an agarose matrix in the present of a developer solution in PBS.

Figure 6D:
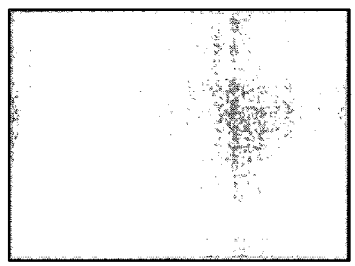

The experiment was also performed on a slide from slide group A in the absence of a developer. A slide from the slide group A was photographed. FIG. 6D. is a photograph of a microscopic field of view of an AgBr containing agarose matrix coated slide of slide group A.

Figure 6E:
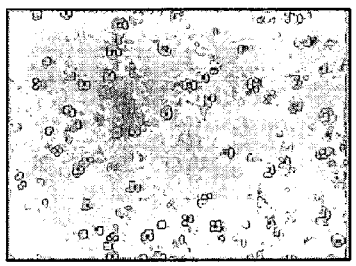
Figure 6F:
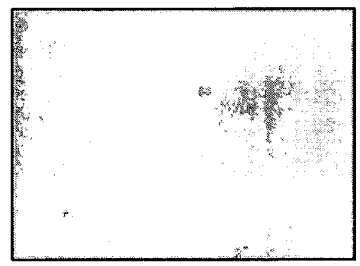

200 microliters of the cells suspended in PBS were placed on the slide from slide group A (no developer was added). The slide was incubated for 4 minutes to allow cell sedimentation. FIG. 6E is a photograph of a microscopic field of view of the slide after the cell sedimentation occurred (in the absence of developer). The same slide was then removed from the microscope stage, washed three times in PBS (total wash volume of 80 milliliter PBS), returned to the microscope stage for viewing approximately the same field of view and photographed. FIG. 6F is a photograph of a microscopic field of view of the slide after the washing in PBS. The results indicate that DA1 cells exhibit little or no attachment to or adhering to an agarose matrix including photosensitized AgBr which is not developed by a developer.

Figure 6G:
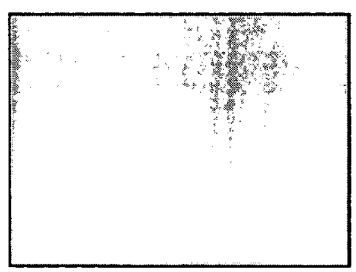

Finally, the experiment was also performed on another slide from slide group A under conditions leading to development of the photosensitized AgBr. Specifically, a slide from the slide group A was photographed. FIG. 6G, is a photograph of a microscopic field of view of the AgBr containing agarose matrix coated slide of slide group A.

Figure 6H:
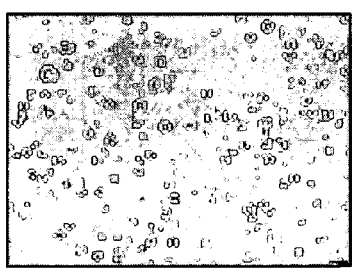
Figure 6I:
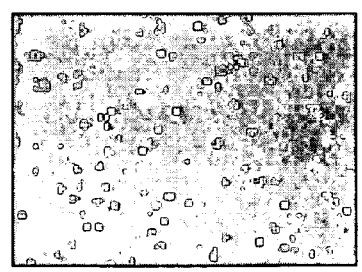

200 microliters of the cells suspended in PBS (including a total of 1×10$^6$ cells) were mixed with 200 microliters of the "½ strength developer in PBS" disclosed hereinabove to yield 400 microliters of cells suspended in developer. The 400 milliliters were then placed on the matrix coated slide. The slide was incubated for 4 minutes to allow cell sedimentation. FIG. 6H is a photograph of a microscopic field of view of the slide after the cell sedimentation occurred (in the presence of the developer). The same slide was then removed from the microscope stage, washed three times in PBS (total wash volume of 80 milliliter PBS), returned to the microscope stage for viewing approximately the same field of view, and photographed. FIG. 6I is a photograph of the field of view of the slide after the washing in PBS. The results indicate that many DA1 cells are attached (even after washing) to the agarose matrix which includes silver grains developed by the developer from photosensitized AgBr particles in the matrix.

The results of EXPERIMENT 1 also indicate that DA1 cells do not strongly adhere to undeveloped photosensitized AgBr in the matrix, or to the agarose matrix by itself.

Localized Cell Adhesion Experiments Using Labeled Cells

A second set of experiments was performed to test the ability of cells labeled with a cell specific photophoric probe to attach or adhere to silver grains locally developed in an agarose matrix. The experiments were based on using a photophoric probe consisting of a conjugate of β subunit of cholera toxin with peroxidase, for labeling JURKAT human T cell leukemia cells. The conjugate was capable of specifically binding to GM1 ganglioside receptors on the membranes of the JURKAT human T cell leukemia cells which were used in the experiment. The labeled cells (and/or non-labeled cells) may be layered on a suitable matrix (such as, for example, an agarose matrix) including the photosensitizable silver salt AgBr.

The incubation of the labeled cells with suitable substrates of the enzyme peroxidase in the presence of a chemiluminescent agent luminol, results in chemiluminescent light emission which is localized at or about the cells to which the photophoric probe (i.e the conjugate of β subunit of cholera toxin with peroxidase) is bound. The light emitted near the labeled cells photosensitizes the silver bromide in the matrix. Subsequent development of the photosensitized silver bromide, results in the formation of silver metal grains, or silver micro-crystals, or silver particles, on and within the matrix. Due to the localized nature of the light emission, the silver metal grains are preferentially formed in the regions of the agarose matrix underlying or near the labeled cells. Thus, the labeled cells will adhere to the surface of the silver grains and will be effectively attached to the matrix. Cells, to which the photophoric probe is not bound will not induce to the localized chemiluminescent emission of light in their vicinity, will not induce the localized formation of silver grains in the matrix underlying them, and will therefore not adhere to the matrix and may be removed by washing.

Cell Preparation

Cells from a JURKAT human T cell leukemia cell line were used in EXPERIMENT 2. This cell line is disclosed by Schneider et al. in an article titled "CHARACTERIZATION OF EBV-GENOME NEGATIVE "NULL" AND "T" CELL LINES DERIVED FROM CHILDREN WITH ACCUTE LIMPHOBLASTIC LEUKEMIA AND LEUKEMIC TRANSFORMED NON-HODGKIN LYMPHOMA" published in Int. J. Cancer, Vol. 19 pp. 621-626 (1977). The cells were grown in Roswell Park Memorial Institute (RPMI) 1640 growth medium (commercially available as Catalogue Number R8758 from Sigma, U.S.A), including 7% heat inactivated fetal calf serum commercially available as catalogue number 04-121-1A from Biological Industries, Beit Haemek, Israel, and 1/100 (by volume) of L-glutamine (Catalogue No. G-7513, Sigma-Aldrich, U.S.A.). The cell were grown to a cell density of $0.5 \times 10^6$ cells per milliliter. Prior to performing the experiment, the cells were harvested and washed three times in phosphate buffered saline (PBS) to remove the growth medium. The composition of the PBS was as disclosed in detail hereinabove. The cells were resuspended in PBS to a cell density of approximately $5 \times 10^6$ cells per milliliter and the cell suspension was stored at 4° C.

Preparation of Agarose Matrix Coated Petri Dishes

1% agarose (w/v) in 0.1M NaBr was prepared as disclosed hereinabove. The hot agarose matrix was poured into 40 millimeters diameter plastic Petri dishes and the agarose was allowed to solidify by incubating the Petri dishes at 4° C. for 5 minutes. The thickness of the agarose matrix on the bottom of the Petri dishes was approximately 0.5 millimeters. A solution of 0.1M $AgNO_3$ in doubly distilled water was poured into all the Petri dishes and left in the dishes for 3 minutes to form photosensitizable silver bromide in the agarose matrix. The dishes where then washed three times with doubly distilled water, treated with 0.1M NaBr solution for 1 minute and washed three times with PBS.

All the Petri dishes were stored in a darkroom until used to avoid photosensitization of the AgBr in the agarose matrix.

A ½ strength stock solution of Kodak GBX developer in PBS was prepared as disclosed in detail hereinabove.

EXPERIMENT 2

This experiment tested the adherence of JURKAT human T leukemia cells to an agarose matrix including AgBr which is locally photosensitized by light produced by a localized chemiluminescence reaction of a probe specifically labeling the human T cell leukemia cells and developed. All the experimental procedures for EXPERIMENT 2 were carried out in a darkroom (except for the last step of microscopic observation and photography of the Petry dishes).

All the slides in EXPERIMENT 2 were visually observed under an Olympus model CK40 microscope, and photographed using an Olympus model 150IK camera.

Cell Pre-treatment

Three flasks A, B and C were prepared. 10 milliliters of PBS washed JURKAT human T cell leukemia cells suspended in PBS at a cell count of $5 \times 10^6$ cells per milliliter of PBS were placed in each of the flasks A, B and C.

Flask A: 3.0 microliters of a stock solution having a concentration of 1 microgram per microliter of a conjugate of β subunit of cholera toxin with peroxidase were added to the cell suspension in flask A to bring the final concentration of the conjugate to 0.3 microgram per milliliter of cell suspension. The conjugate of β subunit of cholera toxin with peroxidase is commercially available as catalogue number 227041 from Calbiochem, U.S.A. The cells were incubated with the conjugate for 1 hour at 4° C.

Flask B: The contents of flask B were incubated for 1 hour at 4° C. without any addition, and served as a non-conjugate labeled control.

Flask C: This flask was used for preparing cells that were stained with Giemsa stain and also labeled with the conjugate of β subunit of cholera toxin with peroxidase, in order to assist the visualizing of separation of non-conjugate labeled cells from conjugate-labeled cells.

The cells Sedimented from the medium were mixed in flask C with 3 milliliter of Giemsa stain solution, commercially available as catalogue number (Cat. No.) VG 16 from Sigma Chemical Company MI, U.S.A. and 7 milliliters of PBS. After mixing, the contents of flask C were incubated for 1 minute, centrifuged in an Ependorff centrifuge at 1600 rpm for 10 minutes to sediment the cells, and the pellet was resuspended and washed three times in 25 milliliters of PBS. The thrice washed pellet was resuspended in PBS in flask C to a final cell count of $5 \times 10^6$ cells per milliliter of PBS.

3.0 microliters of a solution of 1 microgram per milliliter conjugate of β subunit of cholera toxin with peroxidase were added to the cell suspension in flask C to bring the final concentration of the conjugate to 0.3 microgram per milliliter of cell suspension. The cells in flask C were incubated with the conjugate for 1 hour at 4° C. It is noted that the Giemsa staining procedure disclosed killed the cells. Thus, the cells in flask C are dead cells which are Giemsa stained for visual identification and also labeled with the conjugate of β subunit of cholera toxin with peroxidase.

The cells in each of the flasks A, B, and C were then washed three times in PBS by centrifugation and resuspending of the resulting pellets, the washing served to remove the unbound conjugate. The cells of all three flasks A, B, and C were then resuspended in PBS to a final cell count of $5 \times 10^6$ cells per milliliter of PBS.

Three Petry dishes D, E and F from the Petri dishes containing agarose matrix containing AgBr which were stored in the darkroom were used for testing the attachment of the labeled and non-labeled cells from the flasks A, B, and C. The Petry dishes D, E and F were washed three times with PBS.

Treatment of Petri dish D: 2 milliliters of the cell suspension from flask B (the X control flask) and 2 milliliters of a stock solution of peroxidase reagent mixture were mixed and added to the Petri dish D to cover the agarose matrix layer, and the Petri dish D was left undisturbed for 5 minutes in the darkroom to allow the cells to sediment.

The stock solution of peroxidase reagent mixture included luminol (3 aminophtalhydrazide) at a final concentration of 220 micrograms per milliliter, p-coumaric acid at a final concentration of 74 micrograms per milliliter and hydrogen peroxide ($H_2O_2$) at a final concentration of $2.64 \times 10^{-4}$ M. The luminol, the p-coumaric acid, and the hydrogen peroxide are commercially available as catalogue numbers 09253, C9008, and H1009, respectively, from Sigma Chemical Corporation, MI, U.S.A.

After the 5 minute cell sedimentation ended, 4 milliliters of ½ strength stock solution of Kodak GBX developer in PBS, prepared as disclosed hereinabove in detail were very gently added to the Petri dish D by gentle pippetting the developer solution along the wall of the Petri dish D in order to avoid moving of the sedimented cells. The Petri dish D was then incubated with the developer for 1 minute in the darkroom. The agarose matrix at the bottom of the Petri dish D was then washed three times in PBS (in the darkroom) and then microscopically observed and photographed as disclosed hereinabove.

Figure 7A:
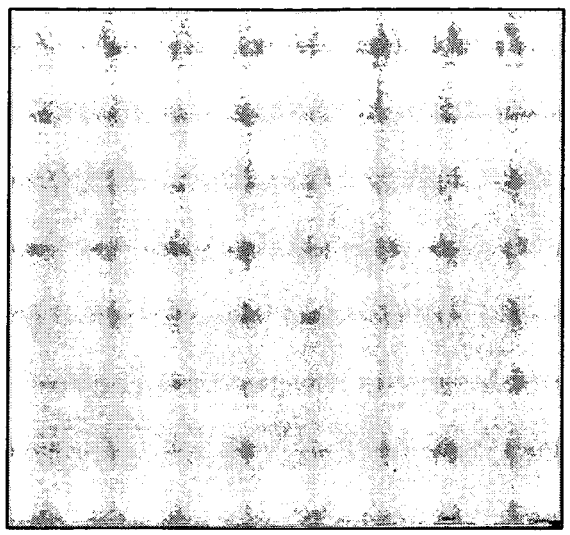
FIGS. 7A-7C are photographs illustrating exemplary results of EXPERIMENT 2 of the specification.
Figure 7B:
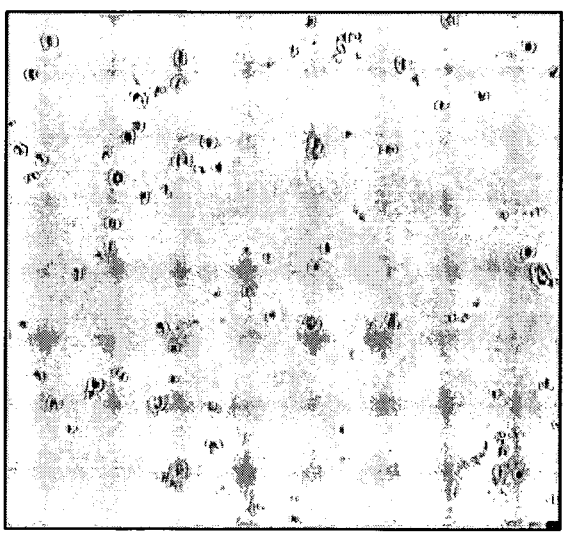
Figure 7C:
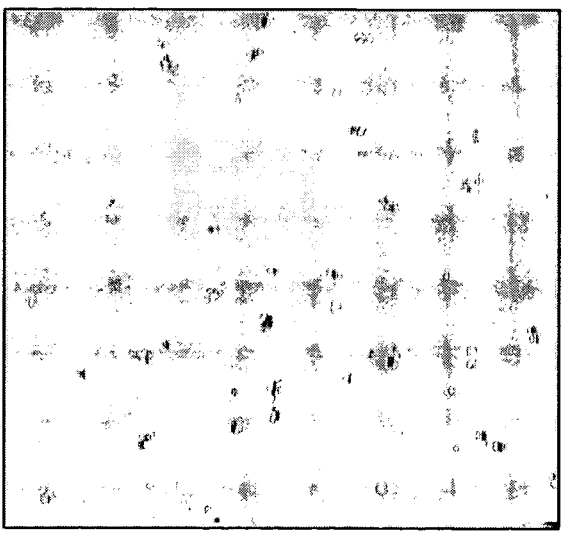

Reference is now made to FIGS. 7A-7C which are photographs of the results of EXPERIMENT 2.

FIG. 7A is a photograph of a microscopic field of view of the agarose coated Petri dish D of EXPERIMENT 2. No cells were observed to be attached to or to adhere to the surface of the agarose matrix of the entire Petri dish D as demonstrated by the exemplary field of view of FIG. 7A.

Treatment of Petri dish E: 2 milliliters of the cell suspension from flask A (the flask containing cells labeled with the conjugate of β subunit of cholera toxin with peroxidase) and 2 milliliters of a stock solution of peroxidase reagent mixture were mixed and added to the Petri dish E to cover the agarose matrix layer, and the Petri dish E was left undisturbed for 5 minutes in the darkroom to allow the cells to sediment.

The composition of the stock solution of peroxidase reagent mixture was as disclosed in detail for Petri dish D hereinabove.

After the 5 minute cell sedimentation ended, 4 milliliters of ½ strength stock solution of Kodak GBX developer in PBS, prepared as disclosed hereinabove in detail, were very gently added to the Petri dish E by gentle pippetting as disclosed hereinabove. The Petri dish E was then incubated with the developer for 1 minute in the darkroom. The agarose matrix at the bottom of the Petri dish E was washed three times in PBS (in the darkroom) and then microscopically observed and photographed as disclosed hereinabove.

FIG. 7B is a photograph of a microscopic field of view of the agarose coated Petri dish E of EXPERIMENT 2. A large number of cells were observed to be attached to or to adhere to the surface of the agarose matrix of the Petri dish E within the field of view of FIG. 7A, similar results were observed for the entire surface of the Petri dish E (not shown).

Treatment of Petri dish F: 1 milliliter of the cell suspension from flask C (the flask containing cells labeled with the conjugate of β subunit of cholera toxin with peroxidase and stained with Giemsa stain), and 1 milliliter of the cell suspension from flask B (the flask containing non-labeled control cells) were mixed with 2 milliliters of a stock solution of peroxidase reagent mixture and added to the Petri dish F to cover the agarose matrix layer. The Petri dish F was left undisturbed for 5 minutes in the darkroom to allow the cells to sediment. The composition of the stock solution of peroxidase reagent mixture was as disclosed in detail for Petri dish D hereinabove.

After the 5 minute cell sedimentation ended, 4 milliliters of ½ strength stock solution of Kodak GBX developer in PBS, prepared as disclosed hereinabove in detail, were very gently added to the Petri dish F by gentle pippetting as disclosed hereinabove. The Petri dish F was then incubated with the developer for 1 minute in the darkroom. The agarose matrix at the bottom of the Petri dish F was washed three times in PBS (in the darkroom) and then microscopically observed and photographed as disclosed hereinabove.

FIG. 7C is a photograph of a microscopic field of view of the agarose coated Petri dish F of EXPERIMENT 2. A number of dead Giemsa stained (purple colored) cells were observed to be attached to or to adhere to the surface of the agarose matrix of the Petri dish F within the field of view of FIG. 7C, it is noted that no non-stained living cells were observed to be attached to the surface of the agarose matrix of within the exemplary field of view of FIG. 7C. Similar results were observed for the entire surface of the Petri dish F (not shown). Thus, most (if not all) of the living non-conjugate labeled cells were removed from the matrix by the washing, leaving behind, the dead, Giemsa stained, conjugate labeled cells which were attached to or adhering to the matrix.

It is noted that, the staining of the cells disclosed in EXPERIMENT 2 above is not a necessary part of the cell separation procedure, but was simply used as a means to visually verify that the conjugate labeled (and stained) cells were left adhering to the matrix and that the non-conjugate labeled (and non-stained) cells did not adhere to the matrix and were washed away in the washing step. Thus, generally, while it may be possible or even desirable in certain cases to stain one or more of the cell types (or particle types) which are to be separated, staining of cells or particles may be but need not necessarily be part of the procedure of separating or sorting the cells or particles.

Furthermore, while the Giemsa staining procedure used hereinabove, killed the cells which were stained, the dead cells were still effectively separated from the living non-conjugated, non-stained cells. This indicates that the separation or sorting method of the present invention, is not limited to living cells, and may be also successfully practiced on non-living cells, or on mixtures of living and non-living cells.

It is further noted that while the experiments disclosed hereinabove demonstrate the use of the cell adhering principle of the present invention for attaching cells to a matrix and for sorting cells, used two specific cell lines as disclosed hereinabove, the cell or particle sorting and/or separating methods and devices of the present invention are not limited to the specific types of cells which were used but are rather generally applicable to many different cell types and particle types which may be suitably selectively and specifically labeled with suitable photophoric probes and which have the property of being capable of adhering to metal grains developed from a photosensitized metal salt dispersed in or included in a suitable matrix.

EXPERIMENT 3

Cell Preparations

Human and mouse fibroblast cells were cultured as disclosed in detail hereinafter. The cells were separately maintained in Dulbeco's modified eagle's medium (DMEM), commercially available as catalogue number D-6546 from Sigma-Aldrich, U.S.A., supplemented with 10% heat inactivated fetal calf serum, commercially available as catalogue number 04-121-1A from Biological Industries, Beit Haemek, Israel, and 10 milligrams per milliliter of gentamycine. The cells were cultured in separate 250 ml flasks, each including 75 milliliters of the medium to a cell count of $1.0 \times 10^7$ cells per flask. The cells were harvested from the flasks by a 25-50 mM ethylenediaminetetraacetic acid (EDTA) solution in PBS.

The cells were fixed prior to performing the experiment.

Cell Fixation Method

The cells were washed once in PBS, centrifuged for 3 minutes at 2000 rpm in an Eppendorff centrifuge and the supernatant was discarded. The volume of the remaining pellet was determined. A solution of 4% paraformaldehyde in PBS buffer having a volume equal to 7 times the volume of the pellet was mixed with the pellet, and the resulting mixture was incubated for 20 minutes. After the incubation, the fixed cells were centrifuged for 3 minutes at 2000 rpm and the supernatant was discarded. The fixed cells were washed twice with a PBS buffer including 100 mM glycine, for 5 minutes, and then washed once with PBS. All the fixation procedure was performed at room temperature. After fixation the cells were stored at 4° C. for a maximum storage period of four days.

Antibody Binding Tests

Mouse and human fibroblasts were grown in the supplemented DMEM growth medium disclosed hereinabove, in 24 well plates up to an approximate concentration $5 \times 10^5$ cells per well. The wells were washed with PBS contains 0.1 mg/ml of $MgCl_2$ and 0.132 mg/ml of $CaCl_2$. In half of the wells of the plates, the cells were fixed by incubation for 20 minutes at room temperate with a fixer solution including 4% paraformaldehyde in PBS buffer (One milliliter of the fixer solution was added per well. After fixation, the fixed cells were washed twice by a volume of 1 ml of PBS including 100 mM glycine at room temperature. The fixed cells were then washed once by a volume of 1 ml of PBS per well for 5 min at room temperature.

The cells in the remaining half of the wells were not fixed and included normal live cells as a control.

The fixed cells and the live cells were then labeled using two different labeling methods and different labeling probes, to test the ability of different probes to bind to fixed and living mouse and human fibroblasts cells, as follows.

Procedure for Labeling with β Subunit of Cholera Toxin-peroxidase Conjugate

The cells (including the live cells and the fixed cells) were Incubated with β subunit of cholera toxin-peroxidase conjugate at a final concentration of 0.5 microgram/ml, by adding to each well 1.0 ml of a solution of 0.5 microgram/ml of β subunit of cholera toxin-peroxidase conjugate (commercially available as Cat. No 227041 from Calbiochem, U.S.A.) in PBS including 0.1 mg/ml of $MgCl_2$ and 0.132 mg/ml of $CaCl_2$. Incubation time was 1 hour at room temperature. The cells in the wells were then washed three times (to remove unbound conjugate), by resuspending the cells three times in 1.0 ml per well of PBS including 0.1 mg/ml of $MgCl_2$ and 0.132 mg/ml of $CaCl_2$, and incubating the resuspended cells for 5 minutes at room temperature.

Procedure for Labeling with Primary and Secondary Antibodies

Live cells and fixed cells in wells were Incubated at room temperature for 1 hour with a primary mouse antibody directed against insulin-like growth factor receptor (mouse anti-IGFR) diluted 1/100. The mouse anti-IGFR antibody (IGF-1 R(Ab-1) Mab) is commercially available as catalogue number GR11 from Oncogene Research Products, U.S.A. After the incubation, the cells in the wells were washed three times (to remove unbound primary antibody), by resuspending the cells three times in 1.0 ml per well of PBS including 0.1 mg/ml of $MgCl_2$ and 0.132 mg/ml of $CaCl_2$, and incubating the resuspended cells for 5 minutes at room temperature.

The cells were then Incubated with a secondary antibody solution for one hour at room temperature. The secondary antibody was anti-mouse IgG-horseradish peroxidase conjugate, (commercially available as Cat. No 402335 from Calbiochem, U.S.A.) (diluted 1/5000) in PBS including 0.1 mg/ml of $MgCl_2$ and 0.132 mg/ml of $CaCl_2$. After the incubation, the cells in the wells were washed three times (to remove unbound secondary antibody), by resuspending the cells three times in 1.0 ml per well of PBS including 0.1 mg/ml of $MgCl_2$ and 0.132 mg/ml of $CaCl_2$, and incubating the resuspended cells for 5 minutes at room temperature. This antibody based labeling method is well known in the art as a two antibody "sandwich method".

The labeled cells (fixed cells and live cells) were tested for peroxidase conjugated probe binding as disclosed hereinbelow.

Cell Staining Procedure (Peroxidase Based)

The cells were stained with 4-chloro-α-naphtol (50 mM/ml) and 0.007% $H_2O_2$ in 20 mM Tris-HCL (pH 8) buffer, as is known in the art. Brown color development on the surfaces of the live and fixed cells was visualized by microscope. The 4-chloro-α-naphtol is commercially available as Cat. No 70493 from Fluka, U.S.A.

For the live cells and the fixed cells labeled with β subunit of cholera toxin-peroxidase conjugate, the full color intensity developed at approximately 6-7 minutes. For the live cells and fixed cells labeled with the two antibody sandwich method the full color intensity developed at approximately 20-25 minutes.

All the cells tested including the fixed and the living cells were observed to be stained with a brown colored peroxidase reaction product. It is therefore concluded that the fixation method disclosed hereinabove did not substantially prevent binding of the antibodies used surface antigens after fixation and did not substantially prevent the biding of the β subunit of cholera toxin-peroxidase conjugate to the fixed cell membranes.

Thus, the fixing method used hereinabove increased cell stability under storage and preserved the cells, while still enabling the labeling of the cells with the different probes which were used, presumably indicating that the membrane target sites on the surface of the cells, such as surface proteins against which the primary antibody used is directed, and other non-protein membranal components such as the GM1 ganglioside which is the binding target for the β subunit of cholera toxin, did retain the ability to bind the primary antibody or the β subunit of cholera toxin, respectively.

Cell Sorting and Separation Procedures

All the procedures for testing the sorting and separation of the mouse and human fibroblast cells disclosed hereinafter used mouse and human fibroblast cells which were fixed as is described in detail hereinabove.

Preparation of Cholera Toxin Labeled Cells

The cells were incubated for 1-2 hours, at room temperature, with a solution of β subunit of cholera toxin-peroxidase conjugate in PBS. The final concentration of the β subunit of cholera toxin-peroxidase conjugate was 1.0 microgram conjugate per 5 milliliters of incubation solution. After the incubation the cells were washed in PBS three times (5 minutes duration of each wash period) to remove unbound conjugate. This procedure was used for labeling both mouse and human fixed fibroblast cells.

Preparation of Obelin Labeled Cells-using Primary and Secondary Antibody Method

After fixation the cells were washed (for 5 minutes) in PBS including 50 mM of EDTA and Incubated in a primary antibody solution including mouse anti-IGFR diluted 1/100 in PBS including 50 mM EDTA. The incubation period was two hours at room temperature, or alternatively over night at 4° C. After the incubation the cells were washed three times in PBS including 50 mM EDTA to remove unbound primary antibody. The washed cells were then incubated for two hours at room temperature with a secondary antibody stock solution comprising rat anti-mouse IgG-obelin conjugate diluted 30-50 times in PBS including 50 mM EDTA. The stock solution of rat anti-mouse IgG-obelin conjugate, at a concentration of 0.8 microgram per microliter, was prepared from rat anti-mouse IgG and the photoprotein Obelin according to the method disclosed in detail in an article entitled "A NEW REAGENT WHICH MAY BE USED TO INTRODUCE SULFHYDRYL GROUPS INTO PROTEINS, AND ITS USE IN THE PREPARATION OF CONJUGATES FOR IMMUNOASSAY" by Julian S. Duncan et al., published in Analytical Biochemistry, 132, 68-73, 1983, and incorporated herein by reference in its entirety.

At the end of the incubation with the secondary antibody, the cells were washed three times with PBS including 50 mM EDTA to remove unbound secondary antibody. This procedure was used for labeling both mouse and human fixed fibroblast cells.

Preparation of Obelin Labeled Cells-using Primary Antibody and Protein A-Obelin Fusion Protein.

After fixation, the cells were washed (for 5 minutes) in PBS including 50 mM of EDTA and Incubated in a primary antibody solution including mouse anti-IGFR IgG diluted 1/100 in PBS including 50 mM EDTA. The incubation period was two hours at room temperature, or alternatively over night at 4° C. After the incubation the cells were washed three times in PBS including 50 mM EDTA to remove unbound primary antibody. The washed cells were then incubated for two hours at room temperature with a solution of protein A-Obelin fusion protein, prepared by diluting a stock solution of the fusion protein containing 0.2 microgram per microliter of protein A-obelin fusion protein, diluted 50 times with PBS including 50 mM of EDTA). The protein A-Obelin fusion protein was obtained from the Krasnoyarsk Institute of Biophysics, Krasnoyarsk, Russia.

At the end of the incubation with the fusion protein, the cells were washed three times with PBS including 50 mM EDTA to remove unbound fusion protein. This procedure was used for labeling both mouse and human fixed fibroblast cells.

Peroxidase Labeled Cells

The cells were incubated for two hours at room temperature (or overnight at 4° C.) in the primary antibody (mouse anti-IGFR) diluted 1/100 in PBS and washed three times for 5 minutes with PBS. The labeled cells were then Incubated for two hours at room temperature with the secondary antibody comprising anti-mouse IgG horseradish peroxidase conjugate (commercially available as Cat. No 402335 from Calbiochem, U.S.A.) diluted 1/5000 in PBS, and washed three times for 5 minutes with PBS.

Methods Used for Cell Separation Experiments

Two different methods were used for performing the cell sorting (cell separation) of EXPERIMENT 3. In the first method, a 30% acrylamide matrix layer was cast at the bottom of standard 40 millimeter diameter plastic Petri dishes as is disclosed in detail hereinafter, and treated for producing the light sensitive layer as is disclosed in detail hereinafter. In this method, after the cells sedimented on the light sensitive matrix layer, further addition of reagent solutions were performed by very gentle pippetting of these added solutions along the side wall of the Petri dishes as disclosed in detail hereinabove for EXPERIMENT 2. The first method, also referred to as the "single sided matrix method" hereinafter, uses standard Petri dishes, similar to the Petri dish 82 schematically illustrated in FIGS. 5C-5F. The silver bromide containing light sensitive layer may be attached to the bottom of the Petri dish or other container or vessel, such as the Petri dish 82 (FIG. 5C). All the solutions required for the preparation of the light sensitive layer and the solutions for implementing the cell (or particle) separation (including for example solutions containing peroxidase substrates for chemiluminescence, or calcium ions for obelin experiments, and the like) are added to the Petri dish and contact the upper surface of the light sensitive layer, such as for example the upper surface of the light sensitive layer 84 (FIG. 5C). The single sided matrix method has the advantage of simplicity and ease of preparation of the matrix containing Petri dishes (or other vessels), while requiring greater caution and manual dexterity in adding the various solutions to the Petri dishes without inducing movement of the sedimented cells contacting the surface of the light sensitive matrix.

The second method, is also referred to as the "double sided matrix diffusion method" hereinafter. In the second method, a layer of matrix may be formed by casting on a perforated plastic mesh to produce a supported matrix layer which is accessible to diffusion of solutes or reagents from solutions contacting both sides of the matrix. This method obviates the need for adding different reagent or developer containing solutions into the layer of liquid in contact with the upper surface of the light sensitive layer.

Figure 10:
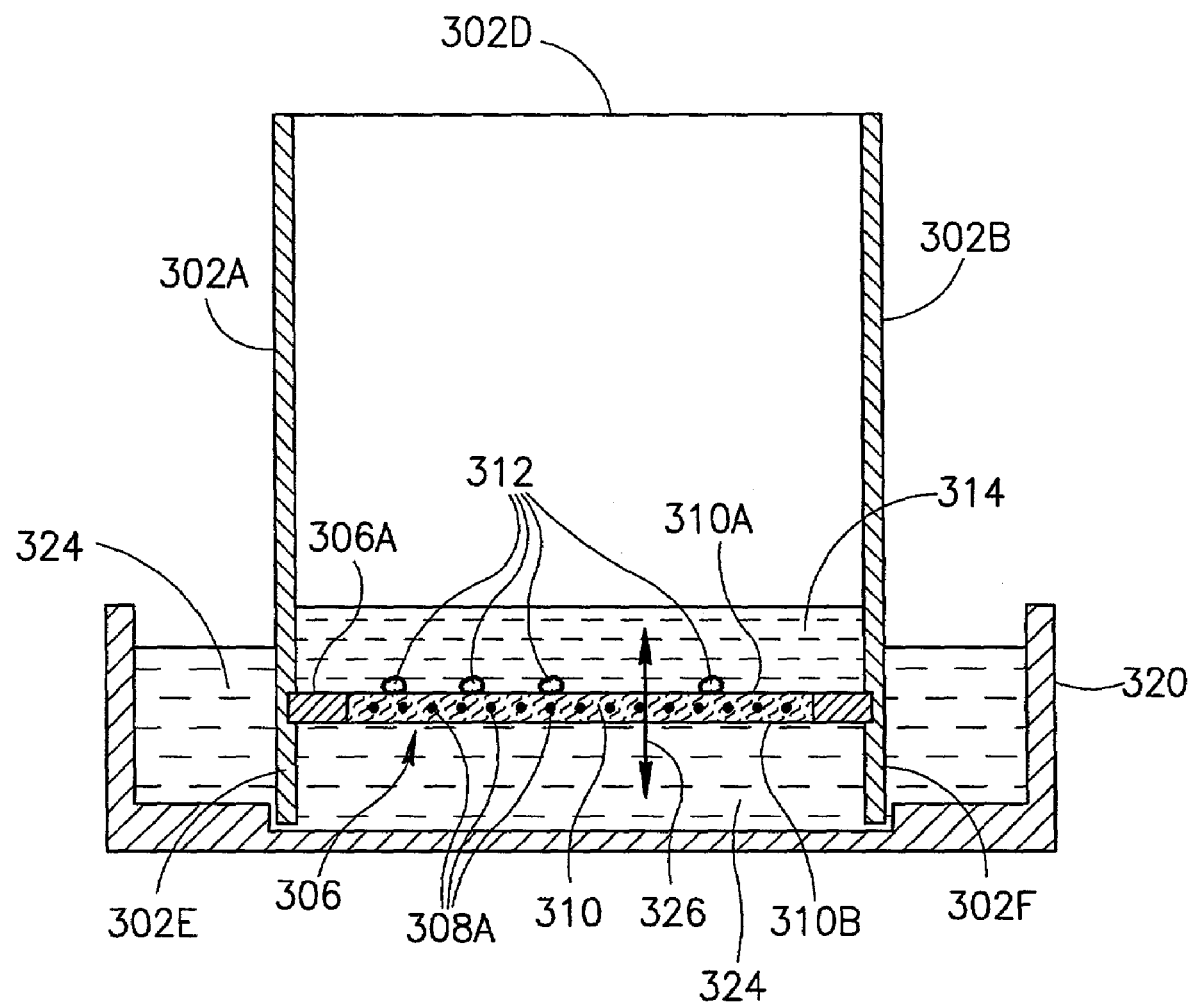
FIG. 10 is a schematic cross sectional view of the particle holder illustrated in FIGS. 8-9, disposed in a container including a desired solution.

Reference is now made to FIGS. 8-10 which are schematic drawings useful in understanding the construction of a device for sorting or separating cells or other particles, in accordance with a preferred embodiment of the present invention.

FIG. 8 is a schematic partially isometric view of a particle holder usable for separating cells or other particles, in accordance with one preferred embodiment of the present invention.

FIG. 9 is a schematic cross sectional view of the particle holder illustrated in FIG. 8 taken along the lines IX-IX.

FIG. 10 is a schematic cross sectional view of the particle holder illustrated in FIGS. 8-9, disposed in a container including a desired solution.

The holder 300 is a rectangular holder which includes two side walls 302A and 302B and two additional walls 302C and 302D. The side walls 302A and 302B have slots 304A and 304B, respectively, formed therein. The holder 300 further includes a bottom part 306. In the holders used for EXPERIMENT 3 the four walls 302A-302D are made of perspex®, but any other type of suitable materials, such as but not limited to plastic or glass, and the like may be used. The bottom part 306 includes a bracket 306A, a mesh 308 suitably attached to the bracket 306A and a matrix 310. The mesh 308 is embedded in the matrix 310 (best seen in FIG. 9). Typically, the matrix 310 may be a matrix or a membrane which may be permeable to water molecules and to certain solutes or reagents included in a solution (not shown in FIGS. 8 and 9) which may be in contact with the matrix 310.

In EXPERIMENT 3, the bracket 306A was a plastic photographic slide frame. The mesh 308 was a fine nylon mesh having holes with approximate dimensions of 0.5×0.5 millimeters. The fibers 308A of the mesh 308 had an approximate fiber diameter of 0.01 millimeters. A rectangular piece of the mesh 308, slightly larger in dimensions than the opening of the bracket 306A, was fastened within the bracket 306A. The bracket 306A was then placed on a flat glass plate (not shown), and 15% polyacrylamide gel was cast within the opening of the bracket 306A and allowed to polymerized and solidify as is known in the art. To prevent leakage of the polyacrylamide gel prior to polymerization, the contact points (not shown) between the glass plate (not shown) and the bracket 306A were sealed with a 1% agarose prior to casting of the polyacrylamide gel.

After the polymerization was completed, the mesh 308 is embedded within the polyacrylamide gel of which the matrix 310 is formed. The completed bottom part 306 is then removed from the glass plate, cleaned, and inserted into the slots 304A and 304B of the holder 300. Warm Agarose (1%) was then used to seal the contact points between the bracket 306 and the walls 302A, 302B, 302C and 302D to enable the holder 300 to hold a liquid (not shown in FIGS. 8-9) inserted therein without leaks.

It is noted that the mesh 308 was used to provide mechanical support for the matrix 310 since the 15% polyacrylamide gel comprising the matrix 310 is relatively soft. However, the matrix 310 may be also made from other materials such as other types of gels, or other suitable non-gel-like matrices such as solid membranes having a suitable permeability to the reagents that need to penetrate the membrane. If such solid semi-permeable or partly permeable membranes are used, it may be possible to eliminate the mesh 308, if the membrane is capable of mechanically supporting its weight and the weight of the liquids or solutions introduced into the holder 300.

Briefly turning to FIG. 10, the gel comprising matrix 310 of the holder 300 may be prepared and treated as disclosed in detail hereinafter to form a light sensitive layer (not shown in detail in FIG. 10 for the sake of clarity of illustration). The light sensitive layer may include, inter alia, silver bromide formed on the upper surface 310A of the matrix 310. The holder 300 may be partially filled with a suspension of cells 312 to be sorted or separated.

The cells 312 are suspended in a solution 314. The cells 312 of FIG. 10 are illustrated as being in contact with the upper surface 310A of the matrix 310 as happens after cell sedimentation. Some of the cells 312 may have a cell-specific photophoric probe bound to them directly or indirectly as disclosed in detail hereinabove (such as, for example, the peroxidase conjugate, or the obelin-protein A conjugates disclosed hereinabove). After cell sedimentation, The holder 300 including the cells 312 (including probe labeled cells and non-labeled cells) may be placed within an incubation container 320. The container 320 may be a rectangular shallow vessel having a recessed bottom part 320A. The recessed bottom part 320A is adapted to have dimensions suitable for receiving and holding the lower ends 302E and 302F of the side walls 302A and 302B, respectively, to prevent movement of the holder 300 within the container 320. The container 320 may be filled or partially filled with a solution 324. The solution 324 may contact the lower surface 310B of the matrix 310. When the holder 300 is placed in the solution 324 contained within the container 320, there is no trapping of air bubbles under the surface 310B since air may leave through the openings 307 (best seen in FIG. 8) on the front and the back sides of the holder 300.

The solution 324 is in contact with the lower surface 310B of the matrix 310. The solution 324 may include one or more of the reagents or substances needed to induce the production of light from the photophoric probe either by direct emission of light from the probe or by participating in a reaction which will induce the localized emission or production of light in the vicinity of the probe labeling some of the cells 312. For example, if some of the cells 312 are specifically labeled by a obelin conjugated probe or a fusion protein comprising obelin (such as but not limited to the obelin-protein A fusion protein disclosed hereinabove), the solution 324 may include calcium ions capable of inducing the emission of light from obelin as is known in the art. Calcium ions may diffuse through the 15% polyacrylamide since the matrix 310 is permeable to calcium ions. Given enough time, calcium ions will diffuse through the matrix 310 and enter the solution 314. The obelin in the probes may then emit light in the presence of calcium ions which will lead to the photosensitizing of the photosensitizable silver bromide in or on the surface 310A as is disclosed in detail hereinabove. At a later stage, the holder 300 may be gently removed from the container 320 dipped in water for washing and disposed in another container (not shown) similar in shape to the container 320 and including a solution of developer.

The developer may then diffuse through the matrix 310 into the solution 314 held within the holder 300 and develop the photosensitized regions of the silver bromide containing layer disposed upon the upper surface 310A of the matrix 310, to locally form metallic silver grains. The labeled cells may become attached to the developed silver grains and thus the target (labeled) cells 312 will adhere to the surface 310A. The holder 300 may then be washed to remove the non-adhering cells of the cells 312 as disclosed in detail hereinabove. If desired, the holder 300 may then be filled with a solution including a proteolytic enzyme as disclosed in detail hereinabove to detach the adhering cells from the surface 310A for harvesting or collecting the sorted cells.

The advantage of the method of cell sorting using the above disclosed double sided matrix diffusion method and the holder 300, is that due to the fact that after sedimentation of the cells 312 in the holder 300, the necessary reagents or developer are introduced by diffusion through the matrix 310 as disclosed hereinabove and need not be directly added to the solution 314 within the holder 300, thus considerably reducing the risk of causing turbulence or undesirable fluid movements which may cause dislodging or moving the cells 312 from their positions after or during the photosensitization step or during the development step. This improves the method of cell separation by simplifying the performing of the method by users with little or no training, and may also improve the yield of separated cells and reduce the percentage of contaminating non-target cells which are harvested in the purified cell preparation.

It is noted that while the double sided matrix diffusion method disclosed hereinabove may simplify manual operations and may result in better cell yield and lower cross-contamination, in may require longer incubation times in order to enable diffusion of sufficient quantities of reactants or developer through the matrix 310. These increased incubation times may be reduced or otherwise controlled by proper modification of the thickness, and/or permeability and/or other physical or chemical properties of the matrix 310.

It is noted that while solutes (not shown) may move by diffusion from the solution 324 into the solution 314 through the matrix 310, the same solute or other different solutes may move through the matrix 310 in the direction from the solution 314 into the solution 324. The possible directions for solute or reactant movements are schematically indicated by the double headed arrow labeled 326. The movements of various solutes is generally governed in accordance with well known physical laws known in the art, depending, inter alia, on the concentration gradients of the particular diffusing solute existing across the matrix 310, and on the properties of the matrix 310, such as its permeability to specific solutes, and the like.

Preparation of Matrices for Cell Sorting and Separation Experiment

All the matrices used for EXPERIMENT 3 were polyacrylamide based matrices.

Method of Polyacrylamide Matrix Preparation for Single Sided Matrix Method

30% acrylamide stock solution was prepared by dissolving 30 grams of acrylamide in DDW, adding 1.5 grams of bis-acrylamide (the bis-acrylamide/acrylamide ratio is 1/20). This stock solution was stored in the dark at 4° C. and used for all the experiments using the single sided matrix method.

The following steps were performed under normal room lighting conditions. 5.0 milliliters of 30% acrylamide stock solution were mixed with 50 microliters of a silver nitrate stock solution including 1% $AgNO_3$ (w/v), 50 microliters of gelatin stock solution including 1% gelatin (w/v), 40 microliters of a 20% solution of ammonium per sulfate (APS) and 5 microliters of N,N,N',N' Tetramethylethylenediamine (TEMED). The resulting mixture was transferred to 40 millimeters diameter plastic Petri dishes, allowed to polymerize and washed twice with DDW. The polymerized acrylamide gel layer was then incubated for 1 hour with a gelatin solution including 0.01% gelatin (w/v) in DDW and for an additional 1 hour with a silver nitrate solution containing 0.01% $AgNO_3$ (w/v) in DDW. The Petri dishes were then washed once in DDW, incubated for 30 minutes with a solution of 5% (W/v) KBr in DDW, and washed twice with DDW.

The following steps were then performed in a darkroom: The Petri dishes were incubated for 30 minutes with a silver nitrate solution containing 0.01% $AgNO_3$ (w/v) in DDW. The Petri dishes were then incubated for 30 minutes with a gelatin solution including 0.01% gelatin (w/v) in DDW, washed twice in DDW, incubated for 30 minutes with a solution of 5% (W/v) KBr in DDW, washed twice with DDW, and washed once in PBS.

Preparation of Holders for Double Sided Matrix Diffusion Method

The matrix 310 of the holders 300 used for implementing the cell separation in accordance with the double sided matrix diffusion method was based on a 15% cross-linked polyacrylamide gel matrix in order to facilitate diffusion of solutes through the matrix 310 to shorten the duration of required incubation periods.

15% acrylamide solution for preparing the matrix 310 of the cell holders 300 (FIG. 8) was prepared by performing the following steps under normal room lighting conditions. 2.5 milliliters of the 30% acrylamide stock solution disclosed hereinabove were mixed with 2.5 milliliters DDW, 50 microliters of a silver nitrate stock solution including 1% $AgNO_3$ (w/v), 50 microliters of gelatin stock solution including 1% gelatin (w/v), 70 microliters of a 20% solution of ammonium per sulfate (APS) and 5 microliters of N,N,N',N' Tetramethylethylenediamine (TEMED). The resulting mixture was cast into a plurality of the bottom parts 306 (FIG. 8) lying on a glass plate, as disclosed in detail hereinabove, the gel was allowed to polymerize to form the matrix 310 (best seen in FIG. 9) and washed twice with DDW. Each of the bottom parts 306 was then removed from the glass plate, cleaned and inserted into the slots 304A and 304B of a separate holder 300. Each holder 300 of the plurality of holders was sealed using warm agarose solution as disclosed hereinabove. The polymerized 15% acrylamide gel layer comprising the matrix 310 was then incubated for 1 hour with a gelatin solution including 0.01% gelatin (w/v) in DDW, by adding the gelatin solution to the holder 300 such that in covered the upper surface 310A of the matrix 310. The matrix 310 was then incubated for one hour with a silver nitrate solution containing 0.01% $AgNO_3$ (w/v) in DDW. The holders 300 were then washed once in DDW, incubated for 30 minutes with a solution of 5% (W/v) KBr in DDW to form silver bromide on the matrix 310, and washed twice with DDW.

The following steps were then performed in a darkroom: the holders 300 were incubated for 30 minutes with a silver nitrate solution containing 0.01% $AgNO_3$ (w/v) in DDW. The holders 300 were then incubated for 30 minutes with a gelatin solution including 0.01% gelatin (w/v) in DDW, washed twice in DDW, incubated for 30 minutes with a solution of 5% (w/v) KBr in DDW, washed twice with DDW, and washed once in PBS. The exact details of the rest of the steps of the cell separation of EXPERIMENT 3 are disclosed in detail hereinafter.

Methods for Identifying and Detecting Sorted or Separated Cells

In EXPERIMENT 3, two types of different fibroblast cells (mouse and human fibroblast cells) were chosen to demonstrate the sorting and separating of cells using one separation method according to the present invention. The chosen mouse and human fibroblast cells, originating in cancer cell lines (C3H mouse cell line, and T24 human cell line), had an approximately similar size and morphology.

Cultured Human and Mouse Fibroblast Cells

Mouse C3H cells were obtained in culture as disclosed in detail in the article entitled "QUANTITATIVE AND QUALITATIVE STUDIES OF CHEMICAL TRANSFORMATION OF CLONED C3H MOUSE EMBRIO CELLS SENSITIVE TO POSTCONFLUENCE INHIBITION OF CELL DIVISION" by Reznikoff C. A. et al. published in Cancer Res. Vol. 33 pp. 3239-3249, 1973, incorporated herein by reference, and in the article entitled "REPAIR OF POTENTIALLY LETHAL RADIATION DAMAGE IN MAMMALIAN CELLS IS ASSOCIATED WITH ENHANCEMENT OF MALIGNANT TRANSFORMATION" by Terzaghi M. and Little J. B., published in Nature Vol. 253, pp. 548-549, 1975, incorporated herein by reference.

Human T24 cells were obtained in culture as disclosed in detail in pp. 103-125 of Volume IV of the book entitled "IN VITRO MODELS FOR CANCER RESEARCH" Eds. Webber, M. M., and Sekely, L. I., published by CRC Press, Boca Raton, Fla. U.S.A. 1986, incorporated herein by reference, and in an article entitled "CELLULAR IMMUNITY TO HUMAN URINARY BLADDER CARCINOMA. I. CORRELATION TO CLINICAL STAGE AND RADIOTHERAPY" by Otoole C. et al. published in Int. J. Cancer, Vol. 10, pp. 77-91, 1972, incorporated herein by reference.

The detection and identification of the cells prior to and after sorting, (or separating) was based on species specific chromosome labeling chosen for the reason that they have good sensitivity and low levels of false positive and false negative signals. The chromosome detection method was based on the use of DNA probes specific for whole chromosomes of mouse and man. The DNA probes were prepared from leucocyte total chromosome material using degenerative oligonucleotide primers—polymerase chain reaction (DOP-PCR) methods, as is well known in the art. The DNA probes specific to human chromosomal DNA were labeled with digoxigenin. The DNA probes specific to mouse chromosomal DNA were labeled with biotin.

The labeled DNA probes were tested by preparing microscope slides with human and mouse cells using standard methods for DNA analysis. The slides were analyzed after hybridization with one of the DNA probes (either the human specific probe, or the mouse specific probe) or with both of the DNA probes, by standard fluorescent in situ hybridization (FISH) methods.

Cultivation of Leukocytes from Peripheral Human Blood

Peripheral venous human blood (5-7 ml) was collected under sterile conditions in a penicillinic bottle including 0.1 ml of heparin solution (commercially available as Catalogue No. H 3393, from Sigma, U.S.A) containing 250 heparin units/ml. The collected blood was incubated for 15-60 minutes at room temperature. 1.0 ml of the leucocyte layer was collected and transferred to a 50 ml flask, and mixed with 7 ml of Roswell Park Memorial Institute (RPMI) 1640 growth medium (commercially available as Catalogue Number R8758 from Sigma, U.S.A) containing 10 mg/ml gentamycine (commercially available as catalogue No. G 9654, from Sigma, U.S.A). Leukocyte division was stimulated by adding 0.1 ml of phytohemagglutinin A (PHA) solution (commercially available as Catalogue No. L 9132, from Sigma, U.S.A) and 1 ml of fetal calf serum to the flask. The flask with the cells was incubated for 72 hours at 37° C.

Cultivation of Mouse Splenocites

To obtain mouse spleen leucocytes (splenocytes) spleens were surgically extracted under sterile conditions from BALB-C mice. The spleens were dissected and manually shredded with a sterile needle and sterile forceps under RPMI-1640 growth medium. 5.0 ml of the resulting cell suspension was incubated with 0.1 ml of a heparin solution containing 250 heparin units/ml for 15-60 minutes at room temperature, and then 1 ml of the resulting spleen leukocyte (spleenocyte) layer was collected, transferred to a 50 ml flask, and mixed with 7 ml of RPMI-1640 growth medium containing 10 mg/ml gentamycine, spleenocyte division was stimulated by adding 0.1 ml of PHA solution and 1 ml of fetal calf serum to the flask. The flask with the cells was incubated for 72 hours at 37° C.

DOP-PCR with AmpliTaq, Stoffel Fragment DNA Polymerase

Amplification of genomic DNA with DOP-Shuttle-PCR was performed as described in detail in an article entitled "A METHOD FOR THE RAPID SEQUENCE-INDEPENDENT AMPLIFICATION OF MICRODISSECTED CHROMOSOMAL MATERIAL" by Bohlander et al. published in Genomics, Vol. 13, pp. 1322-1324, 1992, incorporated herein by reference, and in an article entitled "RAPID GENERATION OF REGION SPECIFIC PROBES BY CHROMOSOME MICRODISSECTION AND THEIR APPLICATION" by Meltzer, P. S. et al., published in Nature Genet., Vol. 1, pp. 24-28, 1992, incorporated herein by reference.

Chromosome material was obtained from live human and mouse spleen leucocytes cells. Approximately $2 \times 10^3$ leucocytes were incubated at 37° C., for 30 minutes, in 100 microliters of an incubation medium including 10 mM Tris HCl (pH 7.5) (commercially available as Cat. No. 1185-53-1 from Schaslau, Spain), 10 mM NaCl, 0.1% (w/v) SDS (commercially available as Cat. No. DX2945 from EM Scientific, NJ U.S.A.), 30% (w/v) glycerin (commercially available as Cat. No. 49767 from Fluka Chemie AG), and 0.5 milligram/ml proteinase K (commercially available as Cat. No. 1964364 from Roche Diagnostics Corporation). After incubation, 1.0 microliter of the incubated material was transferred into a sterile 0.5 ml test tube (Eppendorf, Safe Lock), containing 4.5 microliters of a reaction mixture containing 10 mM Tris HCl, 10 mM KCl, 0.2 mM of deoxyadenosine 5' triphosphate (dATP), 0.2 mM of deoxyguanosine 5' triphosphate (dGTP), 0.2 mM of deoxyuracil 5' triphosphate (dUTP), 0.2 mM of deoxycytosine 5' triphosphate (dCTP), 5 micromolar DOP-primer having the sequence (5-CCGACTCGAGNNNNNNATGTGG-3), 5 mM MgCl2, 0.1% BSA. The pH of the reaction mixture was adjusted to 8.3 with HCl. The test tubes were incubated for 5 minutes at 96° C. for inactivation of the proteinase K in an Eppendorf thermocycler (model Mastercycler® personal) with the cover temperature set to 105° C. The test tube was quickly cooled by placing it on ice for condensation of liquids on the walls of the test tube. The test tube was shortly centrifuged, and 2 units of AmpliTaq, Stoffel Fragment DNA polymerase (commercially available as Catalogue Number N808-0038 from Applied Biosystems, U.S.A) were added to the test tube.

DOP-PCR was carried out in the test tube in the Eppendorf thermocycler with a cover temperature of 105° C. in the following temperature mode: initial denaturation within 1 minute at 94° C. with the subsequent 10 cycles for creating a pool of DNA fragments. Each of the 10 cycles included 1 minute at 94° C., 1.5 minutes at 25° C., a transition to 72° C. by raising the temperature by 0.23° C. per second, and 2 minutes at 72° C. After the low temperature cycles ended, the test tube was transferred to ice, and briefly centrifuged. 50 microliters of a second reaction mixture were than added to each of the test tubes. The second reaction mixture included 1×Stoffel buffer (commercially supplied with the polymerase from Applied Biosystems), 0.2 mM of deoxyadenosine 5' triphosphate (dATP), 0.2 mM of deoxyguanosine 5' triphosphate (dGTP), 0.2 mM of deoxyuracil 5' triphosphate (dUTP), 0.2 mM of deoxycytosine 5' triphosphate (dCTP), 1.0 micromolar DOP-primer, 5 mM $MgCl_2$ and 5 units of AmpliTaq, Stoffel Fragment DNA polymerase. The mixture was incubated for 2 minutes at 94° C. The mixture was then subjected to 19 high-temperature cycles. Each of the 19 high temperature cycles included 1 minute at 94° C. 1.5 minutes at 56° C., and 2 minutes at 72° C. Upon termination of the high temperature cycles, the test tubes were incubated for 8 minutes at 72° C. for full end elongation of the DNA chains.

The Quality and quantity of the amplified DNA product were checked by standard electrophoresis on 1.5% agarose gel. 5 microliters of the final reaction mix was loaded on the gel. The agarose gels were stained with ethydium bromide (0.1 microgram/ml). The stained gels were visualized using ultra-violet light as is known in the art.

Labeling of DNA Probes

Reaction Mixture I for Preparing Mouse Specific Labeled Probes 1.0 microliter of mouse DOP-libraries, obtained as disclosed hereinabove, was added to 20 microliters of a PCR-mix having the following composition: 10 mM Tris HCl (pH adjusted to 8.3), 50 mM KCl (catalogue No. 60128, Fluka), 0.2 mM dATP, 0.2 mM dCTP, 0.2 mM dGTP, 0.1 mM dTTP, 0.1 mM biotin-16-dUTP (commercially available as Catalogue No. 1 093 070 from Roche Molecular Biochemicals, U.S.A), 2.0 micromolar DOP-primer, 2.5 micromolar $MgCl_2$, and 1.5 units of Taq DNA polymerase (commercially available as Catalogue No. 1861 from Promega, U.S.A).

Reaction Mixture II for Preparing Human Specific Labeled Probes 1.0 microliter of human DOP-libraries, obtained as disclosed hereinabove, was added to 20 microliters of a PCR reaction mix having the following composition: 10 mM Tris HCl (pH adjusted to 8.3), 50 mM KCl, 0.2 mM dATP, 0.2 mM dCTP, 0.2 mM dGTP, 0.1 mM dTTP, 0.1 mM digoxigenin-11-dUTP (commercially available as Catalogue No. 1 558 706 from Roche Molecular Biochemicals, U.S.A), 2.0 micromolar DOP-primer, 2,5 micromolar $MgCl_2$ and 1.5 units of Taq DNA polymerase.

The mouse specific fluorescent DNA probes and the human specific fluorescent DNA probes were prepared by subjecting the reaction mixture I and the reaction mixture II, respectively, prepared as disclosed hereinabove, to 17 cycles of polymerase chain reaction (PCR) performed in an Eppendorf Mastercycler® thermocycler, with the cover temperature set to 105° C., Each PCR cycle included 1 minute denaturation at 94° C., 1,5 minutes at 56° C., 2 minutes at 72° C., for elongation of the chains, and 8 minutes at 72° C., for finishing elongation.

volumes of 2 microliters of the resulting labeled products were checked by electrophoresis on 1.5% agarose gel as disclosed hereinabove.

Method of Fixation of Mitotic Cells

To obtain preparations of poorly condensed chromosomes, ethydium bromide was added to 10 ml of suspended cultured cells for reaching a final ethydium bromide concentration of 1.0 milligram per liter. The ethydium bromide was added to the cultured cells approximately 1.5-2.0 hours prior to the beginning of cell fixation. Colchicine, was added to the cultured cells by adding 0.3 ml of colchicine (commercially available as catalogue No. C 9754, from Sigma, U.S.A) stock solution having a concentration of 0.4 mg/ml to the cell suspension. The cell suspension was transferred to a centrifuge tube, and centrifuged for 5 minutes at 1000 rpm. The supernatant was discarded and the cells were resuspended in 0,56% hypotonic solution KCl and incubated for 15 minutes at 37° C. The cells were fixed by adding 5 drops of a fixing agent including a mixture of methanol and acetic acid (3:1 v/v) to the cell suspension, mixing the contents of the test tube, and incubating the test tube for 5 minutes at 4° C. The contents of a test tube were centrifuged, the supernatant was discarded and the cells were resuspended again in cold freshly prepared fixing agent (3:1 methanol/acetic acid). The test tube was then maintained at 4° C. for 20 minutes, centrifuged and the supernatant was discarded. The cell pellet was resuspended in freshly prepared fixing agent (3:1 methanol/acetic acid), incubated for 40 minutes at 4° C., and the tube was centrifuged again. The pellet was resuspended in the same freshly prepared fixing agent(3:1 methanol/acetic acid) and the fixed cell suspension was stored at 20° C.

Preparation of Material for FISH

Prior to preparation of chromosome slides for performing FISH, the fixing agent in which cells were stored, was replaced with cold, freshly prepared fixing agent (3:1 methanol/acetic acid). A pipette containing a suspension of the fixed cells was positioned 30-50 centimeters above the surface of a clean, cold moist microscope slide, and a drop of the cell suspension was dropped on the surface of the slide. The cytoplasm of the cells was cleared from the slide by lightly drying the slides at room temperature and washing the slide twice out a cold fixing agent. The slides were finally dried up in the air at room temperature, or alternatively by heating the slides on a heating plate at 56° C.

In situ Hybridization Procedures

In situ hybridization was performed, as disclosed in detail in an article entitled "CYTOGENIC ANALYSIS USING QUANTITATIVE HIGH SENSITIVITY FLUORESCENCE HYBRIDIZATION" by Pinkel et al., published in Proc. Natl. Acad. Sci. USA, Vol 83, pp. 2934-2938, 1986, incorporated herein by reference. In a test tube, 0.4 micrograms of fluorescent labeled DNA probes, prepared as disclosed hereinabove, were mixed with 20 micrograms of salmon sperm DNA, in a total volume of 100 microliters of DDW. 300 microliters of cold 96% ethanol were added to the mixture. The tube was incubated for 30 minutes at 70° C., and centrifuged at 14000 rpm for 20 minutes. The supernatant was discarded. The residue was dried and resuspended in 20 microliters of a hybridization mix including 50% formamide (Cat No. F7503, Sigma, U.S.A), 10% dextran sulfate, 1% Twin-20 (commercially available as Cat. No. 170-6531 from Bio-Rad, U.S.A.), and 2×SSC solution, adjusted to pH 7.0. Denaturation of the probes was carried out for three minutes at 96° C.

It is noted that 20×SSC stock solution was prepared by dissolving 175.3 grams of NaCl and 88.2 grams of sodium citrate in 1.0 liter of DDW. The notation 2×SSC in the composition of the above hybridization mix indicates that 20 microliter of the final hybridization mix included 2 microliters of the above disclosed 20×SSC stock solution.

Cytological preparations of metaphases chromosomes on microscope slides were incubated with RNase A (Cat. No. R4642, Sigma, USA) at a final concentration of 100 micrograms/ml in 2×SSC for two hours at 37° C. The preparations were then dehydrated in an ethanol series of increasing ethanol concentration (70%, 80%, and 96%) and dried at room temperature. Removal of the cytoplasmic residues was performed by incubation for 10 minutes at 37° C. in a solution of 0,02% pepsin in 10 mM HCl. The preparations were then washed twice for 5 minutes in a phosphate buffer including 0.13M NaCl, 0.27 mM KCl, 7.0 mM $Na_2HPO_4$, 3.0 mM $NaH_2PO_4$, adjusted to pH 7.2. The preparations were then washed once in a phosphate buffer containing 0.13M NaCl, 0.27 mM KCl, 7.0 mM $Na_2HPO_4$, 3.0 mM $NaH_2PO_4$, 50 mM $MgCl_2$, adjusted to pH 7.2. Fixing of the cytological material was carried out for 10 minutes at room temperature in a phosphate buffered fixative containing 0.13M NaCl, 0.27 mM KCl, 7.0 mM $Na_2HPO_4$, 3.0 mM $NaH_2PO_4$, 50 mM $MgCl_2$, 1% formaldehyde (Cat. No. F1268, Sigma, USA), adjusted to pH 7.2.

After fixation, the preparations were washed in the phosphate buffer and dehydrated in a standard ethanol series.

Denaturation of the preparations was carried out for 2 minutes at 70° C. in 70% formamide in 2×SSC. The preparations were immediately dehydrated in a cold ethanol series (70%, 80%, and 96% ethanol) for 3 minutes. The preparations were then air dried, 20 microliters of the DNA probes in the hybridization mix disclosed hereinabove where put on the dried preparation, covered by a microscope coverslip and the slide preparations were left in a damp chamber at 42° C. for 16 h to complete the hybridization.

Methods for Fluorescent Labeling of DNA-PROBE on Cytological Preparations

Detection of Hybridized DNA-PROBE Labeled with Biotin-16-dUTP

Upon termination of hybridization, the coverslips were carefully were washed off with 2×SSC. The slide preparations were washed three times in freshly prepared 50% formamide in 2×SSC, washed once with 2×SSC at 42° C., washed three times in 0.2×SSC at 42° C., and incubated for 5 minutes at room temperature in a solution of 0.1% Twin-20 in 4×SSC. The preparations were then placed in a blocking buffer including 3% bovine serum albumin and 0.1% Twin-20 in 4×SSC, and incubated in the blocking buffer for 30 minutes at 42° C. After the termination of incubation in the blocking buffer, 30 microliters of conjugate solution was placed under the cover slips.

detection of the biotin labeled DNA probes was performed using avidin-D cell sorting grade conjugate with fluorescein isothiocyanate (avidin-FITC) (commercially available as Cat No. A-2011 from Vector Laboratories, Burlingame Calif., USA). A solution of Avidin-FITC, having a concentration of 5 micrograms/ml Avidin-FITC in the blocking buffer disclosed hereinabove which was prepared. The solution of avidin-FITC was centrifuged for 6 minutes at 10000 rpm to precipitate non-dissolved particulate matter and the supernatant was used. After addition of the 30 microliters of the Avidin-FITC conjugate, the covered slide was placed in the damp chamber and incubated at 42° C. for 30 minutes. Upon termination of reaction, the coverslip was removed and the slide was washed three times (each wash was for 5 minutes) with a high ionic strength solution containing 0.1% Twin-20 in 4×SSC, at 42° C. To amplify the signal the slides 30 microliters of biotinylated goat anti-avidin antibody commercially available as catalogue number BA-0300 from Vector Laboratories, Burlingame, Calif., USA, at a concentration of 0.05 microgram/ml in blocking buffer were added on the slides, covered with a coverslip, and the slides were incubated for 30 minutes at 42° C.

Upon termination of the amplification reaction, the coverslips were removed, and the slides were washed three times (5 minutes duration for each wash) in 4×SSC; 0.1% Twin-20 at 42° C. After the washing was completed, 30 microliters of avidin-FITC were again added on the preparation, the slides were covered with coverslips and incubated at 42° C., for 30 min. The coverslips were again removed and the preparation slides were washed three times in 4×SSC, 0.1% Twin-20 at 42° C.

Staining of chromosomal material was performed using 4,6-diamidino-2-phenyl-indole (DAPI), commercially available as catalogue number 236 276 from Roche Molecular Biochemicals, USA. The DAPI was dissolved in VECTASHIELD anti-fade solution (commercially available as catalogue number H-1000 from vector laboratories) to a final concentration 200 micrograms/ml.

Detection of Hybridized DNA-probe Labeled with Digoxigenin-11-dUTP hybridization of DNA fragments labeled with digoxigenin-11-dUTP containing probes was performed as disclosed hereinabove for biotin-labeled probes. The conjugate used was a conjugate of the fluorescent dye Cy3 with a specific anti-digoxigenin antibody commercially available From Laboratoria Medigen, Novosibirsk, Russia.

A solution of anti-digoxigenin antibody-Cy3 conjugate at an approximate concentration of 2 micrograms/ml was diluted 1:125 in the blocking buffer. Non-dissolved particles were precipitated by centrifugation at 10000 rpm for 6 minutes and the supernatant was used. The cytological preparations were incubated under a coverslip for 30 minutes at 42° C. with 30 microliters of the supernatant of the anti-digoxigenin antibody-Cy3 conjugate solution (as disclosed hereinabove for the avidin-FITC conjugate). For reduction of the background level the preparations were washed once at room temperature for 5 minutes in 0.1% Twin-20 in 4×SSC, and then washed twice for 5 minutes in PBS at room temperature. The preparations were then dehydrated in a series of spirits of concentration (70%, 80%, 96%). The chromosome preparations were also stained with DAPI as disclosed hereinabove.

Joint Visualization of the Different Hapten Labeled DNA Probes Hybridized on the Same Preparation In case of simultaneous hybridization of the two different types of chromosomal material (human and mouse) with DNA probes marked with different haptens (digoxigenin and biotin as disclosed hereinabove), FISH was carried out under conditions similar to the conditions used for FISH using a single type of DNA probe. However, the total amount of hybridization buffer including the two different DNA probes which was used on the cytological preparation did not exceed 20-25 microliters.

Solutions of avidin-FITC conjugate (1:250 in hybridization buffer), and anti-digoxigenin antibody-Cy3 conjugate (1:125 in hybridization buffer) were prepared as disclosed hereinabove and mixed in the ratio 1:1. The preparation was incubated under a coverslip with 30 microliters of the conjugate mixture for 30 minutes at 42° C., and washed in 4×SSC; 0.1% Twin-20. The amplification was performed by incubating the preparations with the goat anti-avidin antibody and avidin-FITC as disclosed in detail hereinabove.

Microscopic Analysis of Chromosomal Preparations

The chromosomal preparations were analyzed in model AXIOSCOP 2, Zeiss fluorescence microscope, equipped with a CCD-Camera and was analyzed using the "ISIS" software program commercially available from METASYSTEMS GmbH, Germany. The human nuclear material appeared red and the mouse nuclear material appeared yellow-green. FITC fluorescence (yellow-green) was visualized, observed and analyzed using No. 09 filter set available with the AXIOSCOP 2, and Cy3 fluorescence (red) was visualized, observed and analyzed using No. 15 filter set available with the AXIOSCOP 2. For total cell counting DAPI fluorescence (blue) was visualized, observed and analyzed using No. 02 filter set available with the AXIOSCOP 2.

In composite digital pseudo-color photomicrograph the fluorescently labeled nuclear material from fixed mouse and human fibroblast cells obtained by fluorescent in situ hybridization (FISH) were visualized. The green fluorescing human cell nuclei were clearly distinguished from the red fluorescing mouse cell nucleus. The composite photographs represented superimposition of three separate sets of data acquired by the digital camera and pseudo-colored for presentation. The first set of data was acquired using the No. 09 filter set available with the AXIOSCOP 2 for FITC visualization and is pseudo-colored green, the second set of data was acquired using the No. 15 filter set available with the AXIOSCOP 2 for Cy3 visualization of the same field of view, and is pseudo-colored red. The third set of data was acquired using the No. 02 filter set available with the AXIOSCOP 2 for DAPI visualization of the same field of view, and is pseudo-colored blue. The three sets of data were artificially combined by ISIS software to form composite digital pseudo-color photomicrographs for visual counting of cells.

The pseudo color photomicrographs were not a true photographs but were composite processed digital images artificially generated by combining or superposing three pseudo-colored digital data sets separately acquired using each of the three different filter sets indicated above. Thus, for example, in the photomicrographs, human nuclear material may appear violet or purple due to the superimposition of the red pseudo-color representing the intensity of the data acquired using the No. 15 filter set (the intensity of this data set is related to the intensity of Cy3 fluorescence) on the blue pseudo-color representing the intensity of the data acquired using the No. 02 filter set (the intensity of this data set is related to the intensity of DAPI fluorescence). Similarly, mouse nuclear material may appear blue-green due to the superimposition of the yellow-green pseudo-color representing the intensity of the data acquired using the No. 09 filter set (the intensity of this data set is related to the intensity of FITC fluorescence) on the blue pseudo-color representing the intensity of the data acquired using the No. 02 filter set (the intensity of this data set is related to the intensity of DAPI fluorescence).

Cell Counting Procedures

In each of the cell separation experiments included in EXPERIMENT 3 disclosed hereinbelow, two microscopes slides were prepared for microscopic examination as disclosed hereinabove, a first slide with the cell mixture before the cell separation procedure and a second slide with the cells which were harvested after by trypsin digestion (as disclosed in detail hereinbelow). 10 different fields of view were analyzed for each of the two microscope slides, and the fluorescent labeled cells in each of the 10 fields of each slide was counted using the FITC visualization filter (No. 09 filter set available with the AXIOSCOP 2), and the Cy3 visualization filter (No. 15 filter set available with the AXIOSCOP 2), to yield cell counts of FITC labeled cells and of Cy3 labeled cells for the same fields of view.

Cell Separation Procedures

It is noted that EXPERIMENT 3 includes five experimental groups including EXPERIMENT 3-I, EXPERIMENT 3-II, EXPERIMENT 3-III, EXPERIMENT 3-IV and EXPERIMENT 3-V as disclosed in detail below.

EXPERIMENT 3-I

This experiment was performed to test and compare adhering capability of fixed mouse fibroblast cells labeled with the two different obelin based photophoric probes disclosed hereinabove, to light sensitive layers, in accordance with a preferred embodiment of the present invention. The methods used for labeling the cells with the obelin based photophoric probes were the method using the fusion protein-obelin conjugate disclosed hereinabove and the antibody-sandwich method using the mouse anti-IGFR as a primary antibody and the goat anti-mouse-obelin conjugate as a secondary antibody as disclosed in detail hereinabove.

A first cell sample containing $1\times10^5$ of the fixed mouse fibroblast cells was labeled using the antibody-sandwich method, as disclosed in detail hereinabove. The cells were suspended in 5 milliliters of PBS including 5 mM EDTA, and put in a first 40 millimeter diameter Petri dish having a light sensitive 30% cross-linked acrylamide matrix layer which was prepared as disclosed in detail hereinabove.

A second cell sample containing $1\times10^5$ of the fixed mouse fibroblast cells were labeled using the fusion protein method as disclosed in detail hereinabove. The cells were suspended in 5 milliliters of PBS including 5 mM EDTA and put in a second 40 mm diameter Petri dish having a light sensitive 30% cross-linked acrylamide matrix layer which was prepared as disclosed in detail hereinabove.

The cells in the first and second Petri dishes were allowed to sediment for 30 minutes in a darkroom. 1.0 milliliter of 0.5M $CaCl_2$ in DDW was then very gently added (by slow pippetting) to each of the Petri dishes to initiate the emission of light by the obelin. The Petri dishes were left undisturbed in the darkroom for 15 minutes. 1.0 milliliter of Kodak GBX developer diluted 1:5 (v/v) in DDW was then gently added to each of the Petri dishes to develop the sensitized silver bromide in the light sensitive agarose matrix layer, and the Petri dishes were left undisturbed for 10 minutes. The Petri dishes were then washed with approximately 100 milliliters DDW to remove non-adhering cells. The cells which were left attached to the light sensitive matrix were harvested by adding 2.0 milliliters of 0.1% Trypsin (Gibco) in PBS to each of the Petri dishes and incubating the Petri dishes for about 10 minutes at 37° C. The trypsin solution including the harvested cells was removed from the Petri dishes, and the harvested cells were washed once and manually counted using a hemacytometer (improved Neubauer, Werber, GB).

A third Petry dish was processed using the same steps as used for the first Petri dish, except that no $CaCl_2$ solution was added after cell sedimentation step, to avoid the emission of light from the obelin. This Petri dish was used as a control.

The attachment level of the cells in the first and in the second Petri dishes was calculated by dividing the number of harvested cells obtained by the tryptic treatment by the total initial amount of cells introduced to the Petri dish at the beginning of the procedure.

Attachment level for cells labeled with antibody sandwich method (First Petri dish) was 64%. Thus, 64% of the cells initially added to the first Petri dish were recovered after harvesting.

Attachment level for cells labeled with fusion protein was 90%. Thus, 90% of the cells initially added to the second Petri dish were recovered after harvesting. No cells were attached in the control Petri dish, indicating that in the absence of localized obelin light emission induced by the calcium ions, no cells adhered to the light sensitive matrix.

Thus, fixed mouse fibroblast cells labeled with obelin based photophoric probes were capable of adhering to the light sensitive layer following development of the light sensitized matrix after the matrix was exposed to light emitted from the obelin conjugated probe in the presence of calcium ions. No cell adhering was observed in the absence of calcium ions.

EXPERIMENT 3-II

Cell Separation Using Single Sided Matrix Method

EXPERIMENT 3-II tested the separation of fixed non-labeled mouse from fixed human fibroblast cells pre-labeled with a cholera toxin β subunit-peroxidase conjugate based photophoric probe in conjunction with luminol. The separation was performed using the single sided matrix method disclosed hereinabove.

40 millimeter diameter Petri dishes with 30% acrylamide light sensitive layer were prepared as disclosed in detail hereinabove.

Fixed Human fibroblasts were separately labeled with cholera toxin β subunit-peroxidase conjugate. 5.0 milliliters of fixed human fibroblast cells having a cell count of $0.4 \times 10^6$ cells per milliliter in PBS were prepared. A stock solution of cholera toxin β subunit-peroxidase conjugate was added to bring the final cholera toxin β subunit-peroxidase conjugate concentration to 1.0 microgram per milliliter of cell suspension. The suspension was incubated for 1 hour at room temperature to allow binding of the conjugate to the cells, and washed 3 times (5 minutes wash duration) in PBS.

$5 \times 10^5$ human fibroblast cells pre-labeled with the cholera toxin β subunit-peroxidase conjugate were then mixed with $7.5 \times 10^5$ non-labeled fixed mouse fibroblast cells and the cell mixture was suspended in a final volume of 1.0 milliliter containing a final concentration of 220 micrograms luminol (3 aminophtalhydrazide) per milliliter of final cell suspension, and a final concentration of 74 micrograms p-coumaric acid per milliliter of final cell suspension.

The cell mixture including the luminol and P-coumaric acid was introduced into a Petri dish with a 30% acrylamide light sensitive layer at the bottom, prepared as disclosed in detail hereinabove. The Petri dish was Incubated for 15 minutes to allow cell sedimentation.

In a darkroom, 0.1 milliliters of a stock solution hydrogen peroxide ($H_2O_2$) having a concentration of 0.37% v/v were very gently added to the Petri dish containing the sedimented cells by gentle pippetting on the wall of the Petri dish as disclosed hereinabove and the Petri dish was left undisturbed for 15 minutes.

After the 15 minute incubation, 0.2 milliliters of Kodak GBX liquid developer, were very gently added to the Petri dish by gentle pippetting of the developer solution along the wall of the Petri dish in order to avoid moving of the sedimented cells. The Petri dish was then incubated with the developer for 10 minutes in the darkroom. The acrylamide matrix at the bottom of the Petri dish was then washed three times in DDW (in the darkroom).

After the washing, 2.0 milliliters of 0.1% trypsin in PBS were introduced into the Petri dish, and the Petri dish was incubated for 10 minutes at 37° C. for detaching and harvesting the separated cells as disclosed hereinabove. The suspension of harvested cells was washed with PBS and processed for FISH as disclosed in detail hereinabove.

Exemplary results of EXPERIMENT 3-II obtained using FISH are as disclosed below.

In composite digital fluorescence pseudo-color photographs of an exemplary part of a field of view of a FISH sample prepared from the initial human and mouse fixed cell mixture prior to cell separation. Both green-blue pseudo-colored fluorescent labeled mouse fibroblast nuclei and violet or purple pseudo-colored fluorescent labeled human fibroblast nuclei were visible.

Results of Experiment 3-II

In composite digital color photograph of an exemplary parts of a field of view of a FISH sample prepared from cells harvested by tryptic digestion from the developed acrylamide light sensitive layer after the mixture of human and mouse fixed cells was separated as disclosed hereinabove. Mouse fibroblast nuclei were observed as green-blue pseudo-colored nuclei in the field of view amongst a plurality of purple or violet pseudo-colored human fibroblast nuclei.

In 10 exemplary microscopic fields of view of the FISH preparations of the harvested cells, a total number of 699 nuclei were counted using DAPI visualization as disclosed hereinabove. A total number of 698 cell nuclei were counted in the same 10 fields of view using Cy3 visualization as disclosed hereinabove, and only 1 cell nucleus was counted in the same 10 microscopic fields of view using FITC visualization as disclosed hereinabove. Thus, the ratio of counted human to mouse fibroblast nuclei was approximately 700:1, respectively.

EXPERIMENT 3-III

Cell Separation Using Double Sided Matrix Diffusion Method, a Primary Antibody and a Peroxidase Labeled Secondary Antibody EXPERIMENT 3-III tested the separation of fixed non-labeled mouse fibroblast cells from fixed human fibroblast cells pre-labeled with a primary antibody (mouse anti IGFR) and a secondary antibody (peroxidase-conjugated anti mouse IgG) using an antibody sandwich method. The localized photosensitization was performed using the luminol reagent mixture as disclosed hereinabove. The separation was performed using the double sided matrix diffusion method disclosed hereinabove.

Fixed Human fibroblasts were separately labeled with mouse anti IGFR antibody (diluted 1/100 in PBS) as disclosed in detail hereinabove, the incubation time with the primary antibody was 1 hour at room temperature followed by 3 washes in PBS (5 minutes wash time) and by a 1 hour incubation with horseradish peroxidase conjugated anti-mouse IgG (diluted 1/5,000 in PBS) and three washes in PBS (5 minutes wash time) to yield pre-labeled fixed human fibroblast cells.

$1 \times 10^5$ pre-labeled fixed human fibroblast cells were then mixed with $1.0 \times 10^6$ non-labeled fixed mouse fibroblast cells and the cell mixture was suspended in a final volume of 1.0 milliliter containing a final concentration of 220 micrograms luminol (3 aminophtalhydrazide) per milliliter of final cell suspension, and a final concentration of 74 micrograms p-coumaric acid per milliliter of final cell suspension.

The cell mixture including the luminol and P-coumaric acid was introduced in a darkroom into a holder similar to the holder 300 illustrated in FIG. 8 including a 15% acrylamide light sensitive matrix 310, prepared as disclosed in detail hereinabove. The holder 300 was left undisturbed for 15 minutes to allow cell sedimentation.

Approximately 8-10 milliliters of a 0.37% solution of $H_2O_2$ in PBS were put in an incubation container similar to the incubation container 320 of FIG. 10. The holder 300 including the sedimented cells was then carefully placed into the incubation container including the $H_2O_2$ in PBS and the holder 300 was left undisturbed for 30 minutes to allow diffusion of the $H_2O_2$ through the matrix 310.

After the 30 minute incubation, the $H_2O_2$ solution was removed from the incubation container 320 by aspiration without disturbing the holder 300, the incubation container 320 was washed by filling with approximately 8-10 milliliters DDW, and the incubation container 320 was filled with approximately 8-10 milliliters of Kodak GBX liquid developer diluted 1:5 with DDW. The holder 300 was then left undisturbed in the developer solution for 30 minutes in the darkroom. At the end of the 30 minute development period, the matrix 310 of the holder 300 was washed by repeatedly filling the holder 300 with 30 milliliters of DDW (in the darkroom) and pouring the DDW out of the holder 300. The DDW wash was repeated three times.

After the washing, the bottom part 306 was removed from the holder 300, the matrix 310 including the mesh 308 was separated from the bracket 306 A and placed in a 10 centimeter diameter Petri dish (not shown) The Petri dish was then filled with approximately 10-15 milliliters of 0.1% trypsin in PBS, and the Petri dish was incubated for 5-10 minutes at 37° C. for detaching and harvesting the separated cells as disclosed hereinabove. The resulting suspension of harvested cells was washed with PBS by centrifugation and processed for FISH as disclosed in detail hereinabove.

Composite digital pseudo-color photomicrographs of exemplary parts of various different fields of view of a FISH sample prepared from the initial human and mouse fixed cell mixture of EXPERIMENT 3-III prior to cell separation, were prepared and examined as disclosed in detail hereinabove. Both green-blue pseudo-colored fluorescent labeled mouse fibroblast nuclei and violet-purple pseudo-colored fluorescent labeled human fibroblast nuclei were discernible in the pseudo-color photomicrographs.

Results of Experiment 3-III

Composite digital fluorescence pseudo-color photograph of exemplary parts of fields of view of a FISH sample prepared from cells harvested by tryptic digestion from the developed acrylamide light sensitive layer after the mixture of human and mouse fixed cells was separated as disclosed hereinabove.

In 10 exemplary microscopic fields of view of the FISH preparations of the harvested cells, a total number of 584 nuclei were counted using DAPI visualization as disclosed hereinabove. A total number of 582 cell nuclei were counted in the same 10 fields of view using Cy3 visualization as disclosed hereinabove, and only 2 cell nuclei were counted in the same 10 fields of view using FITC visualization as disclosed hereinabove. Thus, the ratio of counted human to mouse fibroblast nuclei was approximately 290:1, respectively.

EXPERIMENT 3-IV

Cell Separation Using Double Sided Matrix Diffusion Method with Obelin Conjugate EXPERIMENT 3-IV tested the separation of fixed mouse fibroblast cells pre-labeled with a primary antibody (mouse anti IGFR) and a secondary antibody (obelin-conjugate of rat anti mouse IgG) using an antibody sandwich method, from fixed non-labeled human fibroblast cells. The localized photosensitization was performed using calcium ion induced light emission from the obelin conjugate as disclosed hereinabove. The separation was performed using the double sided matrix diffusion method disclosed hereinabove.

Fixed mouse fibroblasts were separately labeled with mouse anti IGFR (1/100 in PBS) as disclosed in detail hereinabove, the incubation time with the primary antibody was one hour at room temperature followed by 3 washes in PBS (5 minutes wash time). After the washing the primary antibody labeled cells were incubated for two hours with obelin-conjugated rat anti mouse IgG prepared by diluting one volume of stock solution of 0.8 microgram obelin-conjugate of rat anti mouse IgG in 50 volumes of PBS. After the incubation with the secondary antibody was terminated, the cells were washed three times in PBS (5 minutes wash time) to yield pre-labeled fixed mouse fibroblast cells.

$10^4$ pre-labeled fixed mouse fibroblast cells were then mixed with $10^6$ non-labeled fixed human fibroblast cells and the cell mixture was suspended in a final volume of 1.0 milliliter PBS. The ratio of the mouse to human cells in this cell mixture was 1:100.

The cell mixture was introduced in a darkroom into a holder similar to the holder 300 illustrated in FIG. 8 including a 15% acrylamide light sensitive matrix 310, prepared as disclosed in detail hereinabove. The holder 300 was left undisturbed for 15 minutes to allow cell sedimentation.

Approximately 8-10 milliliters of a solution of 0.5M $CaCl_2$ in DDW were put in an incubation container similar to the incubation container 320 of FIG. 10. The holder 300 including the sedimented cells was then carefully placed into the incubation container 320 including the 0.5M $CaCl_2$ and the holder 300 was left undisturbed for 30 minutes to allow diffusion of the calcium ions through the matrix 310.

After the 30 minute incubation, the $CaCl_2$ solution was removed from the incubation container 320 by aspiration without disturbing the holder 300, the incubation container 320 was washed by filling with approximately 8-10 milliliters DDW, removing the DDW by aspiration, filling the incubation container 320 with approximately 8-10 milliliters of a solution 50 mM EDTA in DDW and leaving the holder in the EDTA solution for 30 minutes, and then removing the EDTA solution by aspiration and adding 8-10 milliliters of DDW to the incubation container 320, and then removing the DDW by aspiration. The EDTA treatment was necessary for removing calcium ions from the matrix 310 in order to prevent undesired interaction between calcium ions and the developer (such interaction may result in the formation of a precipitate or turbidity in the matrix 310 or in the solutions contacting it. The incubation container 320 was then filled with approximately 8-10 milliliters of Kodak GBX liquid developer diluted 1:5 with DDW. The holder 300 was then left undisturbed in the developer solution for 30 minutes (in the darkroom). At the end of the 30 minute development period, the matrix 310 of the holder 300 was washed by repeatedly filling the holder 300 with 30 milliliters of DDW (in the darkroom) and pouring the DDW out of the holder 300. The DDW wash was repeated three times.

After the washing, the bottom part 306 was removed from the holder 300, the matrix 310 including the mesh 308 was separated from the bracket 306A and placed in a 10 centimeter diameter Petri Dish (not shown). The Petri dish was then filed with 10-15 milliliters of 0.1% trypsin in PBS, and was incubated for 5-10 minutes at 37° C. for detaching and harvesting the separated cells as disclosed hereinabove. The resulting suspension of harvested cells was washed with PBS by centrifugation and processed for FISH as disclosed in detail hereinabove.

Composite digital fluorescence pseudo-color photographs of exemplary parts of fields of view of a FISH sample prepared from the initial human and mouse fixed cell mixture of EXPERIMENT 3-IV prior to cell separation, were prepared and visually examined as disclosed in detail hereinabove. Green-blue pseudo-colored fluorescent labeled mouse fibroblast nuclei and violet-purple pseudo-colored fluorescent labeled human fibroblast nuclei were counted in these Composite digital fluorescence pseudo-color photographs, as disclosed in detail hereinabove.

Results of Experiment 3-IV

In composite digital fluorescence pseudo-color photograph of exemplary parts of fields of view of a FISH sample prepared from cells harvested by tryptic digestion from the developed acrylamide light sensitive layer after the mixture of human and mouse fixed cells was separated as disclosed hereinabove. In 10 microscopic fields of view of the FISH preparations of the harvested cells, a total number of 580 nuclei were counted using DAPI visualization as disclosed hereinabove. Only 1 cell nucleus was counted in the same 10 fields of view using Cy3 visualization as disclosed hereinabove, and a total number of 579 cell nuclei were counted in the same 10 fields of view using FITC visualization as disclosed hereinabove. Thus, the ratio of counted mouse to human fibroblast nuclei was approximately 580:1, respectively.

EXPERIMENT 3-V

Cell Separation Using Double Sided Matrix Diffusion Method with Fusion Protein (Protein A-obelin)

EXPERIMENT 3-V tested the separation of fixed human fibroblast cells pre-labeled with a primary antibody (mouse anti-IGFR) and the secondary probe protein A-obelin fusion protein disclosed hereinabove (directed against the $F_c$ region of the primary antibody), from fixed non-labeled mouse fibroblast cells. The localized photosensitization was performed using calcium ion induced light emission from the obelin moiety of the fusion protein as disclosed hereinabove. The separation was performed using the double sided matrix diffusion method disclosed hereinabove.

Fixed human fibroblasts were separately labeled with mouse anti-IGFR (1/100 in PBS) as disclosed in detail hereinabove, the incubation time with the primary antibody was one hour at room temperature followed by 3 washes in PBS (5 minutes wash time) and by a two hours incubation with secondary probe protein A-obelin fusion protein disclosed hereinabove prepared by diluting one volume of stock solution of 0.2 microgram protein A-obelin fusion protein in 50 volumes of PBS. After the incubation with the fusion was terminated, the cells were washed three times in PBS (5 minutes wash time) to yield pre-labeled fixed human fibroblast cells.

Approximately $10^3$ pre-labeled fixed human fibroblast cells were then mixed with $10^6$ non-labeled fixed mouse fibroblast cells and the cell mixture was suspended in a final volume of 1.0 milliliter PBS. The ratio of the human to mouse cells in this cell mixture was 1:1000.

The cell mixture was introduced in a darkroom into a holder similar to the holder 300 illustrated in FIG. 8 including a 15% acrylamide light sensitive matrix 310, prepared as disclosed in detail hereinabove. The holder 300 was left undisturbed for 15 minutes to allow cell sedimentation.

Approximately 8-10 milliliters of a solution of 0.5M $CaCl_2$ in DDW were put in an incubation container similar to the incubation container 320 of FIG. 10. The holder 300 including the sedimented cells was then carefully placed into the incubation container 320 including the 0.5M $CaCl_2$ and the holder 300 was left undisturbed for 30 minutes to allow diffusion of the calcium ions through the matrix 310.

After the 30 minute incubation, the $CaCl_2$ solution was removed from the incubation container 320 by aspiration without disturbing the holder 300, the incubation container 320 was washed by filling with approximately 8-10 milliliters DDW, removing the DDW by aspiration, filling the incubation container 320 with approximately 8-10 milliliters of a solution 50 mM EDTA in DDW and leaving the holder in the EDTA solution for 30 minutes, and then removing the EDTA solution by aspiration and adding 8-10 milliliters of DDW to the incubation container 320, and then removing the DDW by aspiration. The incubation container 320 was then filled with approximately 8-10 milliliters of Kodak GBX liquid developer diluted 1:5 with DDW. The holder 300 was then left undisturbed in the developer solution for 30 minutes (in the darkroom). At the end of the 30 minute development period, the matrix 310 of the holder 300 was washed by repeatedly filling the holder 300 with 30 milliliters of DDW (in the darkroom) and pouring the DDW out of the holder 300. The DDW wash was repeated three times.

After the washing, the bottom part 306 was removed from the holder 300, the matrix 310 including the mesh 308 was separated from the bracket 306 A and placed in a 10 centimeter diameter Petri Dish (not shown) The Petri dish was then filed with 10-15 milliliters of 0.1% trypsin in PBS, and the Petri dish was incubated for 5-10 minutes at 37° C. for detaching and harvesting the separated cells as disclosed hereinabove. The resulting suspension of harvested cells was washed with PBS by centrifugation and processed for FISH as disclosed in detail hereinabove.

Composite digital fluorescence pseudo-color photograph of exemplary parts of fields of view of a FISH sample prepared from the initial human and mouse fixed cell mixture of EXPERIMENT 3-V prior to cell separation, were prepared and visually analyzed, as disclosed in detail hereinabove. Violet-purple pseudo-colored fluorescent labeled human fibroblast nuclei and green-blue pseudo-colored fluorescent labeled mouse fibroblast nuclei were observed and counted.

Composite digital fluorescence pseudo-color photograph of exemplary parts of fields of view of a FISH sample prepared from cells harvested by tryptic digestion from the developed acrylamide light sensitive layer after the mixture of human and mouse fixed cells was separated as disclosed hereinabove, were also taken and analyzed.

Results of Experiment 3-V

In 10 microscopic fields of view of the FISH preparations of the harvested cells, a total number of 380 nuclei were counted using DAPI visualization as disclosed hereinabove. A total number of 380 cell nuclei were counted in the same 10 fields of view using Cy3 visualization as disclosed hereinabove, and no cell nuclei were counted in the same 10 fields of view using FITC visualization as disclosed hereinabove, indicating a highly efficient separation of the human fibroblast cells from the mouse fibroblast cells, even when the separation starts with a cell mixture having an initial ratio of human to mouse cells of 1:1000, respectively.

The results of EXPERIMENT 3 hereinabove demonstrate that different cells in a cell mixture may be quite efficiently sorted or separated using the method of the present invention. Furthermore, the cell separation may be effected using a variety of different types of photophoric probes, including probes that directly emit light in the presence of a specific reagent or activator (i.e the antibody-obelin conjugate/calcium ion system and the protein A-obelin fusion protein/calcium ion system), and probes that chemically react with reactants supplied in the solution surrounding the cells to induce localized chemiluminescence (i.e. peroxidase/$H_2O_2$/p-coumaric acid/luminol system).

It will be appreciated by the person skilled in the art that the method of the present invention is not limited to using the types and nature of the specific photophoric probes disclosed hereinabove and that many other different types of probes may be used, including but not limited to other chemiluminescent agents and probes, anti-stokes phosphors or dyes, two photon up-converting phosphors or dyes, or the like. In principle, any probe which may specifically bind to a desired target particle or cell and which may directly emit suitable photosensitizing light or indirectly cause the localized production of suitable photosensitizing light may be usable in the methods and devices of the present invention. Similarly, while the photophoric probe may directly bind to the target particle or cell (such as in the case of the cholera-toxin-peroxidase conjugated disclosed hereinabove), the photophoric probe may also be specifically bound to a particle or cell by using double or triple or other multiple sandwich methods in which the photophoric probe binds to another probe (such as but not limited to a primary antibody directed against the target cell) which is bound to the particle or cell. Thus, any suitable method known in the art for specific binding of a probe to a target particle or cell may be used to implement the present invention.

It will be appreciated that many types of phosphors, known in the art, may be used in implementing the methods of the present invention. For example, U.S. Pat. No. 5,891,656 to Zarling et al., incorporated herein by reference in its entirety for all purposes, discloses a plurality of types of up-converting reporters for biological and other assays using laser excitation techniques. Many of the up-converting microcrystaline phosphors disclosed by Zarling et al. (for example the phosphors described in columns 12-23 of the Zarling Patent) may be adapted for use in the present invention, by coating them with an antibody or another molecule having an affinity to a specified target cell or target particle.

For example, many of the methods disclosed By Zarling in U.S. Pat. No. 5,891,656 for treating the phosphor particle or microcrystals, and for their linking to or coating with binding reagents having an affinity to specific target groups or molecules or antigens or domains, or the like, may be adapted for use in the methods of cell or particle separating and/or sorting of the present invention. Thus, the photophoric probes used in the methods and devices of the present invention may be prepared using any suitable up-converting phosphor known in the art, including the phosphors disclosed by Zarling, using any method known in the art, including the methods disclosed by Zarling, for functionalizing the phosphor particles to form upconverting labels that may specifically bind to a selected target such as a desired cell, subcellular organelle, or other particle. Such up-converting labels, or upconverting probes may be used as the photophoric probes of the present invention, in conjunction with illumination of the sample to be separated with photons of the appropriate wavelength, during the photosensitization step.

Such coating and adherence of the coated particles to a specific target cell is disclosed in detail hereinafter (in EXPERIMENT 5 which is a specific example using microcrystalline anti-stokes phosphor particles). Other, different, suitable up-converting phosphors may, however, also be used. It is noted that the choice of a particular up-converting phosphor type must be done with consideration of the particular type and characteristics of the light sensitive layer or the photosensitizable metal compound which is being used for the separation of the cells or other particles.

Thus, the photosensitizable metal compound used (either directly or within a suitable matrix or emulsion), is preferably selected such that it is not sensitized or is only weakly sensitized by light of the wavelength or wavelength range which is used for exciting the up-converting particles, while being sufficiently photosensitizable by the photos emitted by the phosphors in response to illumination with the selected exciting photons (preferably infra-red photons), which are effectively up-converted by the phosphor particles.

Alternatively, when it is desired to use a specific photosensitizable matrix or emulsion or compound, the type of the phosphor particles may be selected such that the excitation photons used to illuminate the sample are not effective or are only weakly effective in photosensitizing the photosensitizable compound(s) used in the light sensitive layer of the present invention, while the up-converted photons which are emitted by the chosen phosphor particles are efficient in photosensitizing the photosensitizable compound(s) used in the light sensitive layer which is used.

EXPERIMENT 4

EXPERIMENT 4 was performed to test the ability of cells to adhere to silver grains directly formed on a solid substrate without the use of a gel matrix such as the agarose or acrylamide matrix disclosed hereinabove.

Preparation of Silver Bromide Coated Slides

A clean glass microscope slide was used in the experiment. The slide was placed on a flat horizontal surface in the presence of normal room lighting and a part of the slide was covered with a solution of 0.1 M $AgNO_3$ (commercially available as Cat No. 07523MQ from Aldrich Chemical Company, MO, USA) in DDW. A few drops of 0.1 M NaBr in DDW were dropped on the region previously covered by the $AgNO_3$ solution to precipitate silver bromide on the surface of the slide. The slide was left at room temperature and under normal room lighting for 3 minutes for photosensitizing the precipitated silver bromide. After photosensitization the slide was gently tipped on its side to allow excess silver bromide and fluid to drain of the slide. A volume of 0.2 milliliters of Kodak GBX developer diluted 1:2 in PBS surface and a volume of 0.2 milliliters of a suspension of DA1 mouse lymphoma cells in PBS (having a cell count of $1\times10^6$ cells per milliliter of PBS), were then mixed and placed on the silver bromide covered slide. The DA1 mouse lymphoma cells were grown and cultured as disclosed in detail hereinabove. The mixture of cells and developer was left on the surface of the slide for 4 minutes to allow development and cell sedimentation. The slide surface was then microscopically observed and photographed.

Figure 11:
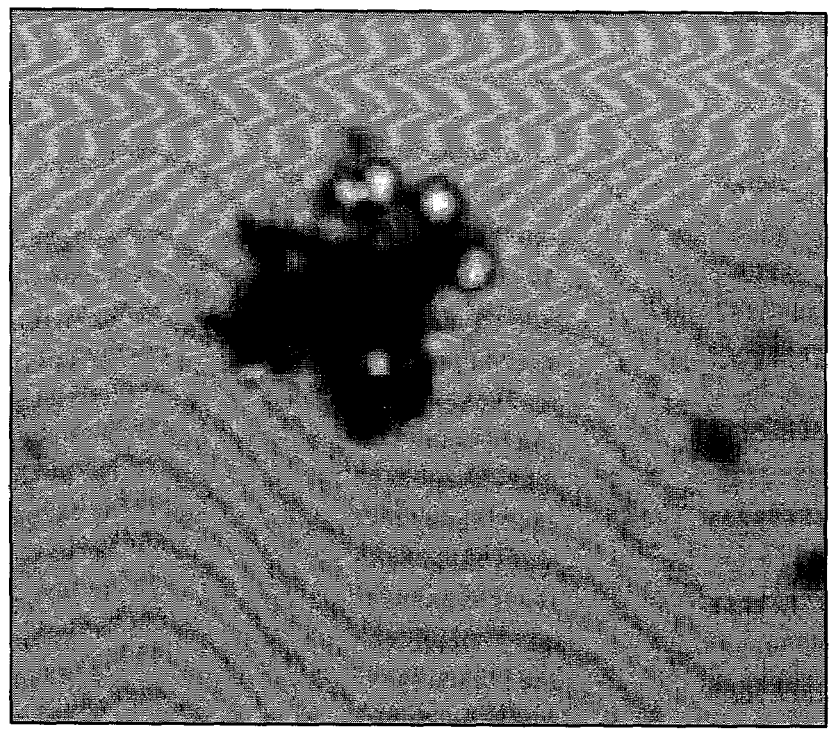
FIGS. 11 and 12 are photomicrographs illustrating exemplary results of EXPERIMENT 4 of the specification.

The results are shown in FIG. 11 to which reference is now made. FIG. 11 is a photomicrograph in which a number of DA1 cells (white, generally spherical shapes) are seen adhering to a developed silver metal grain (black irregular shape). After the photograph of FIG. 11 was taken, the area of the slide including the silver metal grain shown in FIG. 11 was washed with a water stream from the tip of a pipette while the slide was on the microscope. After the washing, the same field of view shown in FIG. 11 was microscopically observed and photographed. The results are shown in FIG. 12 to which reference is now made.

Figure 12:
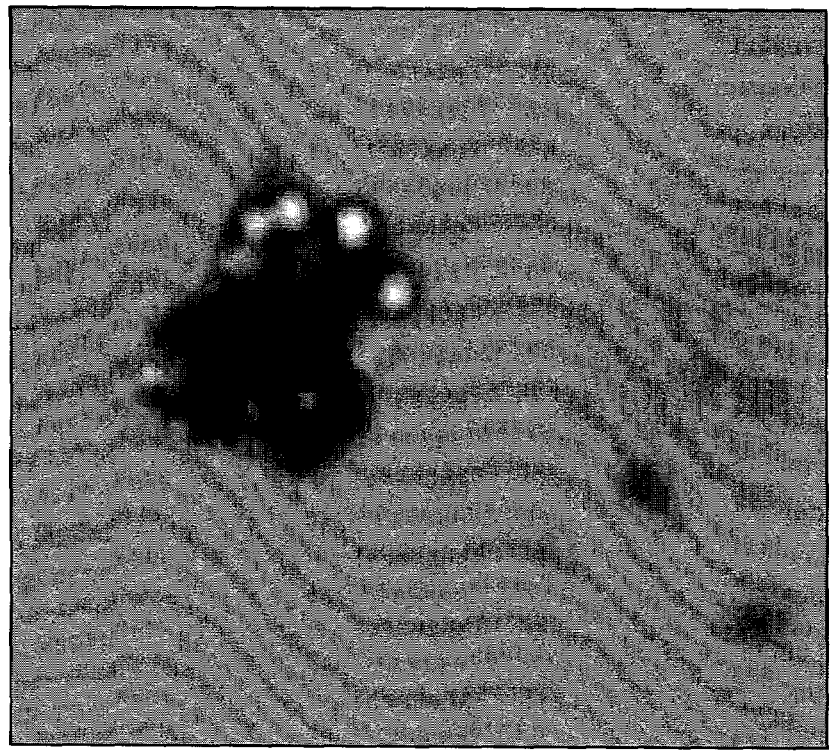

As is seen in FIG. 12, the DA1 cells which were adhering to the silver metal grain were not removed or washed off the silver metal grain and remained attached thereto even though the position of the silver grain itself was slightly shifted relative to the slide surface probably due to the mechanical movement during the washing. Thus, while the use of a matrix (or emulsion) including the photosensitizable metal salt is preferred in the present invention, the results of EXPERIMENT 4 indicate that the presence of a matrix is not required for the adherence of cells to silver metal grains. The results of EXPERIMENT 4 may therefore indicate that the present invention may also be practiced by attaching or coating a substrate (such as but not limited to a glass microscope slide, a Petri dish, or any other type of suitable substrate) with a photosensitizable metal salt (such as but not limited to a silver halide) and using the substrate coated or covered with the photosensitizable metal salt in the method of cell or particle separation or sorting of the present invention in a way similar to the use of the light sensitive matrices disclosed hereinabove.

It will be appreciated by those skilled in the art that many different types of photophoric probes known in the art may be used in implementing the methods for sorting and or separating of particles of the present invention.

For example, in accordance with another preferred embodiment of the present invention, the photophoric probe may include chromophores comprising two-photon up-converting dyes, such as but not limited to the styryl dyes and compositions disclosed in U.S. Pat. No. 5,912,257 to Prasad et al., incorporated herein by reference in its entirety, the benzothiazole-containing chromophores exhibiting strong frequency upconversion disclosed in U.S. Pat. No. 6,100,405 to Reinhardt et al., incorporated herein by reference in its entirety, or any other upconverting dye molecule or chromophore or upconverting particle or upconverting compound known in the art and useful for performing two-photon upconverting.

For example, such chromophores or dyes may be conjugated to, or otherwise chemically or physically coupled or linked to an antibody or other molecule or affinity probe capable of selectively and specifically binding to a target particle or target cell or the like, to form two-photon upconverting photophoric probes. Such two-photon upconverting photophoric probes may be used to selectively label a population of target particles or cells, or subcellular particles, or the like, included in a heterogeneous mixture of different particles. After washing out excess unbound probes, the labeled and non-labeled particles or cells may be applied to the surface of a light sensitive layer, such as but not limited to the light sensitive layer 4 disclosed hereinabove. The particles or cells, may be then exposed to light having a wavelength range which does not photosensitive the light sensitive layer, such as but not limited to infra red light.

The two-photon upconverting chromophores of the two-photon upconverting photophoric probe bound to the target particles or cells may upconvert two photons of the infrared light to a photon having a shorter wavelength (preferably, but not necessarily in the visible range of wavelength) which does photosensitive the light sensitive layer in the vicinity of or underlying the labeled particles or cells. The photosensitized light sensitive layer portions may then be developed to form metal grains (such as, but not limited to the silver grains disclosed hereinabove) to which the probe labeled particles or cells may adhere as disclosed in detail hereinabove. The adhering target particles or cells may then be separated and/or harvested from the non-labeled particles by washing and/or trypsinizing or by using any of the separating steps disclosed hereinabove.

It is noted, that inorganic two photon upconverting particles or inorganic particles capable for exhibiting anti stokes Raman scattering may also be used in the methods for separating particles or cells of the present invention.

EXPERIMENT 5

The experiment tested the ability of small anti stokes phosphor particles coated with antibodies targeted to specific target cells to bind to the target cells against which the antibody is directed.

Materials Used in Experiment 5

Anti stokes phosphor crystals having the composition $(Y_{0.86}Yb_{0.08}Er_{0.06})_2O_2S$, and having an average particle size of approximately 1 micron, were obtained from NPF Luminophor, Stavropol, Russia. PBS was prepared as disclosed hereinabove. Tris-HCl buffer was prepared by preparing a water solution of 0.1M Trizma®-Base, commercially available as catalogue number T-1503 from Sigma Chemical Co., USA, and adjusting the pH to 7.2 with 0.1M HCl. Mouse EL-4 lymphoma cells are commercially available from American Type Cell Collection, U.S.A (ATCC) as catalogue number ATCC-T1B39. Bovine serum albumin (BSA) is commercially available as Catalogue number A-7906 from Sigma Chemical Co., USA.

Mouse monoclonal antibody to mouse H-2Kb MHC (class I) was obtained from CALTAG LABORATORIES, Burlingame, Calif., USA. This antibody was capable of specifically binding to H-2Kb MHC antigenic domains present on the surface of the mouse EL-4 lymphoma cells used in EXPERIMENT 5.

Goat polyclonal antibody directed against T-cell antigen receptor (C-17) is commercially available as catalogue number sc1778 from Santa Cruse biotechnology Inc., CA, USA. This antibody was used as a control non-specific antibody, since it does not bind to the mouse EL-4 lymphoma cells used in EXPERIMENT 5.

Experimental Procedures (for Experiment 5)

Preparation of Phosphor Particle Suspension 50 milligrams of Anti stokes phosphor crystals having the composition $(Y_{0.86}Yb_{0.08}Er_{0.06})_2O_2S$, and having an average particle size of approximately 1 micron were suspended in 2.0 milliliters of dimethyl sulfoxide (DMSO) in a test tube, mixed on a Vortex Genie® 2 shaker and left undisturbed for three days. The resulting supernatant with the phosphor particles included therein was decanted and used in the experiments.

Preparation of Antibody Coated Phosphor Particles

In a first Eppendorf test tube 10 microliters of the phosphor particle suspension in DMSO was mixed with 10 microliters of Tris-HCl buffer (pH=7.2) and 10 microliters of the mouse monoclonal antibody to mouse H-2Kb MHC disclosed hereinabove.

In a second Eppendorf test tube 10 microliters of the phosphor particle suspension in DMSO was mixed with 10 microliters of Tris-HCl buffer (pH=7.2) and 10 microliters of the goat polyclonal antibody directed against T-cell antigen receptor (C-17) disclosed hereinabove.

The contents of the first and the second test tubes were then very gently mixed overnight at room temperature using a Vortex Genie® 2 shaker set at a speed setting of 1 to allow coating of the phosphor particles with the antibodies. Each of the test tubes was then centrifuged at 16100 g for 10 minutes (14,00 revolutions per minute on an Eppendorf model 5415 centrifuge). The pellets in each of the test tubes was washed three times in 30 microliters of PBS to remove excess antibodies. The pellet in each of the test tubes was then resuspended in 30 microliters of a solution of 50 microgram per milliliter BSA, incubated with the BSA solution for two hours for blocking, washed three times in 30 microliters of PBS to remove excess BSA and resuspended in PBS. 30 microliters of a suspension containing $10^6$ mouse EL-4 lymphoma cells per milliliter of PBS was then added to each of the first and second test tubes, and both test tubes were incubated for three hours at room temperature to allow the binding of antibody coated particles to the cells. Samples of the contents of the test tubes were then prepared on glass microscope slides and examined and photographed on a Zeiss Axioscope 2 fluorescence microscope using a UV light source and the number 09 filter set provided with the microscope.

It is noted that the visualization of the phosphor particle binding to the mouse cells relied on the UV fluorescence properties of the phosphor particles and not the anti stokes raman scattering properties of the phosphor particles since these phosphor particles also exhibit easily detectable UV-light induced fluorescence.

Figure 13:
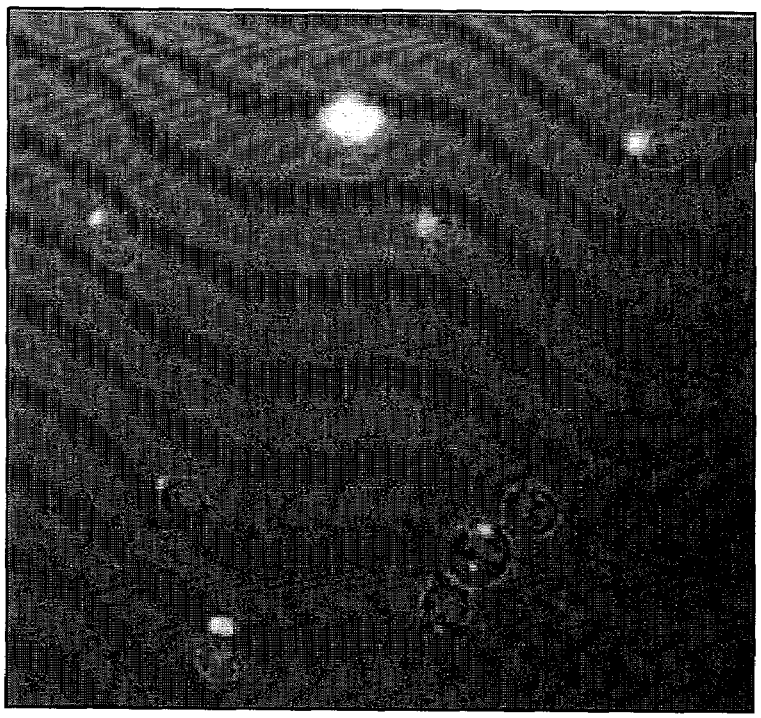
FIGS. 13 and 14 which are photomicrographs illustrating exemplary results of EXPERIMENT 5 of the specification.
Figure 14:
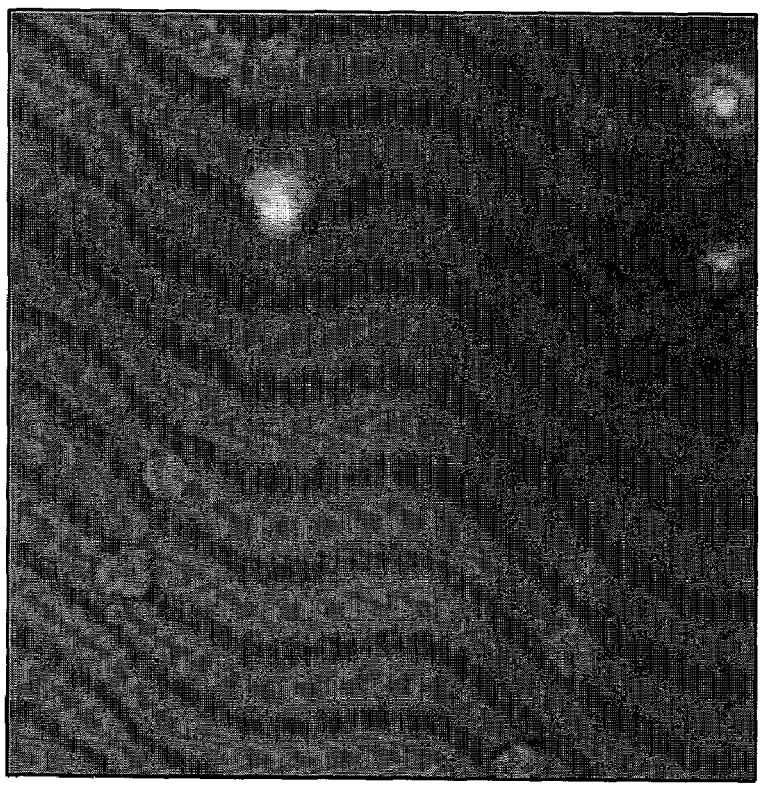

Reference is now made to FIGS. 13 and 14 which are photographs illustrating exemplary results of EXPERIMENT 5. FIG. 13 is a photomicrograph of a sample taken from the first test tube in which the cells were incubated with phosphor particles coated with the mouse monoclonal antibody to mouse H-2Kb MHC. As seen in FIG. 13 phosphor particles (seen as bright spots) are bound to seven out of the nine mouse EL-4 lymphoma cells visible in the photographed field of view of FIG. 13.

FIG. 14 is a photomicrograph of a sample taken from the second test tube in which the cells were incubated with phosphor particles coated with the (non-specific) goat polyclonal antibody directed against T-cell antigen receptor. As seen in FIG. 14 no phosphor particles are bound to any of the mouse EL-4 lymphoma cells visible in the photographed microscopic field of view. The phosphor particles (which are seen as bright spots) are clearly not bound to or associated with any of the five EL-4 lymphoma cells visible in the photographed microscopic field of view of FIG. 14.

These experiments indicate that anti stokes phosphor particles may be coated with specific antibodies directed to specific target cells, and may be used in implementing the cell sorting and/or the cell separating method of the present invention. For example, phosphor particles coated with a specific antibody directed against a target cell may be incubated with a cell mixture which includes the target cells. After the specific binding of the antibody coated phosphor particles to the target cells, the entire cell mixture may be allowed to sediment on a suitable light sensitive layer (not shown) as disclosed hereinabove. The light sensitive layer may then be illuminated with infra-red light having a wavelength range which does not photosensitize the light sensitive metal salt included in the light sensitive layer. Some of the infra-red light photons may be absorbed by the phosphor particles which may then emit photons having a wavelength that is effective in photosensitizing the light sensitive metal salt in the light sensitive layer (due to anti-stokes Raman scattering). Thus, the parts of the light sensitive layer adjacent to the phosphor particles will be photosensitized.

After the photosensitization, the light sensitive layer may be developed as disclosed hereinabove to form metal grains (for example, silver metal grains). Some of the cells to which the phosphor particles are specifically bound may then bind or adhere to the metal grains developed near or adjacent to the cells. Additionally phosphor particles to which no cells are bound may also adhere to the metal grains (due to an interaction of the coating antibody with the metallic surface developed near or under the phosphor particle). However, non-target cells to which no phosphor particles are bound will not adhere to the light sensitive layer since no metal grains are formed in the light sensitive layer adjacent or near these non-target cells. The developed layer may then be washed as disclosed in detail hereinabove to remove the non adhering non-target cells. The adhering target cells may then be harvested from the light sensitive layer using any suitable harvesting method as disclosed hereinabove.

The Materials and Experimental Protocols Used in Experiments 6-14 are Detailed Below BSA (Sigma-Aldrich Israel Ltd., Israel, Cat. No. A7906); EDTA (Sigma-Aldrich Israel Ltd. Cat. No. E5134); Trizma Base (Sigma-Aldrich Israel Ltd., Cat. No. T1503); NaCl (ICN Pharmaceuticals Inc., CA, USA, Cat. No. 102892); $CaCl_2$ (ICN Pharmaceuticals Inc., Cat. No. 193818); Paraformaldehyde (Sigma-Aldrich Israel Ltd., Cat. No. P6148); Glycine (Fluka Chemie AG, Germany, Cat. No. 50046); Vybrant CFDA-SE kit (Molecular Probes Inc., OR, USA, Cat. No. V-12883); 30% acrylamide/bisacrylamide (19:1) (BioRad Laboratories, CA, USA, Cat. No. 161-0154); Polyacrylamide MW 10,000 (Sigma-Aldrich Israel Ltd., Cat. No. 434949); APS (Sigma-Aldrich Israel Ltd., Israel, Cat. No. A7460); Gelatin (Sigma-Aldrich Israel Ltd., Cat. No. G-9382); $AgNO_3$ (Sigma-Aldrich Israel Ltd., Cat. No. 29505.2); TEMED (Sigma-Aldrich Israel Ltd., Cat. No. T9281); KBr (Sigma-Aldrich Israel Ltd., Cat. No. P5912); FCS (Biological Industries, Israel, Cat. No. 04-121-1A); RPMI-1640 (Sigma-Aldrich Israel Ltd., Cat. No. R8758); D-19 developer (Kodak, USA, Cat. No. 190.1859); GBX developer (Kodak, USA, Cat. No. 190-1859) Trypsin-EDTA (Sigma-Aldrich Israel Ltd., Israel, Cat. No. T4049); PMP 15 ml tubes (NalgeNunc International Corp., IL, USA, Cat. No. 3100-0015); Cellulose nitrate membrane (Schleicher & Schuell GmbH, Germany, Cat. No. 10401169); DDW (Merck KGaA, Germany, Cat. No. 1.15333.2500); Sodium-alginate (Sigma-Aldrich Israel Ltd., Cat. No. A-2158); DMSO (Sigma-Aldrich Israel Ltd., Cat. No. Cat. No. D-2650); Luminol (Fluka Chemie AG, Cat. No. 09253); p-coumaric acid (Sigma-Aldrich Israel Ltd., Cat. No. C-9008); $H_2O_2$ 30% (Sigma-Aldrich Israel Ltd., Cat. No. 21676-3); Glucose (Sigma-Aldrich Israel Ltd., Israel, Cat. No. G5400); Manganese-Acetate (Sigma-Aldrich Israel Ltd., Israel, Cat. No. 33082-5); n-Hexane (Riedel-de Haen AG, Germany, Cat. No. 15667); 1-butanol (Sigma-Aldrich Israel Ltd., Israel, Cat. No. 15467-9); Ethanol (Frutarum, Israel, Cat. No. 5551640); Sodium-dodecyl-sulfate (Ambion Inc., TX, USA, Cat. No. 9822); Ammonium Thiocyanate (Sigma-Aldrich Israel Ltd., Israel, Cat. No. 22198-8); Potassium Ferricyanide (Sigma-Aldrich Israel Ltd., Israel, Cat. No. 24,402); PBS was prepared by diluting by 10 folds a (10×) PBS solution commercially available from Biological Industries Ltd. Israel, Cat. No. 02-023-51; Polystyrene 5 ml round-bottomed tubes (USA Scientific Inc., FL, USA, Cat. No. 1450-2000); Trypan Blue (Sigma-Aldrich Israel Ltd., Cat. No.T-8158); Histopaque 1077 gradient (Sigma-Aldrich Israel Ltd., Cat. No. 1077-1); Cholera-toxin-conjugated-to-peroxidase (Calbiochem-Novabiochem, CA, USA, Cat. No. 227041); mouse-anti-human-CD3ε IgG conjugated to horse-radish peroxidase (Santa-Cruz Biotechnoloy Inc., CA, USA, Cat. No. sc-1179HRP); Mouse-anti-human CD3 (Becton Dickinson Immunocytometry Systems, CA, USA, Cat. No. 347340); Alexa Fluor 488 (Molecular Probes Inc., Cat. No. A-11029); Mouse-anti-human CD8 (Becton Dickinson Immunocytometry Systems, Cat. No. 346310); Donkey-anti-mouse-IgG conjugated-to-Cy3 (Jackson ImmunoResearch, PA, USA, Cat. No. 715-165-150); Rabbit-anti-mouse IgG conjugated to obelin was prepared as described in an article entitled: "A NEW REAGENT WHICH MAY BE USED TO INTRODUCE SULFHYDRYL GROUPS INTO PROTEINS AND ITS USE IN THE PREPARATION OF CONJUGATES FOR IMMUNOASSAY" by J. S. Duncan et. al., published in *Analytical Biochemistry* 132, pp. 68-73 (1983);

The Cell lines used are all commercially available from American Type Cell culture (ATCC), VA, USA as follows: EL4 cells (ATCC No. TIB-39) are mouse T lymphocytes established from lymphoma; BW5147.3 cells (ATCC No. TIB-47), (referred to as BW cells in the present application), are mouse T lymphocytes established from thymoma; HH cells (ATCC NO. CRL-2105) are human T lymphocytes established from cutaneous leukemia/lymphoma.

Cells Staining with CFDA-SE

Intracellular staining of viable cells with the fluorescent CFDA-SE Cell Tracer Kit was performed according to the product information sheet MP 12883 supplied with the Vybrant CFDA-SE cell tracer kit.

Cell Fixation Method

4% paraformaldehyde is prepared by adding, while stirring, 4 grams of paraformaldehyde to 90 milliliters of warm (65-70° C.) DDW containing 50 microliters of 1N NaOH. The solution is heated further until the paraformaldehyde is completely dissolved. After cooling to room temperature, 10 milliliters of PBS (10×concentrated) is added and the pH is adjusted to 7.3 with HCl. The solution is sterile filtered through a 0.2 micron filter and stored at 4° C. protected from light up to one month, or kept in aliquots at (−20° C.).

For fixation, every $10^6$ viable cells (either previously-stained or non-stained) are washed in 3 milliliters PBS and centrifuged for 10 minutes at 400 g. After discarding the supernatant, the cells are suspended in a volume of 4% paraformaldehyde in PBS which is 7 times larger than the cell pellet's volume for 20 minutes of incubation at room temperature. After the incubation, the cells are centrifuged for 10 minutes at 400 g, the supernatant is discarded and the pellet is resuspended in 3 ml of 100 mM glycine in PBS for 5 minutes and centrifuged for 5 minutes at 400 g. This glycine washing and centrifugations steps are repeated once more. The fixed cells may then be immediately used or may be kept at 4° C. until the next day.

Preparation of Photoactive Glucose/AgBr/luminol Matrix

The following photosensitive powder ingredients were prepared as follows.

Ingredient 1: A highly dispersed suspension of Silver Bromide was prepared by mixing equal volumes of 0.01M Silver Nitrate and 0.01M Potassium Bromide in a dark room in a vessel having blackened opaque walls. The mixture was left to react for 4 hours and after that left to dry in a Petri dish and collected into a vessel and stored in darkness.

Ingredient 2: Dry luminol was ground in a corundum ball mill to yield luminol particles having a particle size in the range of 1-10 microns.

Ingredient 3: Glucose powder was ground using a corundum ball mill to yield glucose particles having a particle size in the range of 10-100 microns.

Ingredient 4: Manganese acetate was ground in a corundum ball mill to yield manganese acetate particles having a particle size in the range of 1-10 microns.

Ingredient 5: Dried silver nitrate powder was ground in a mortar down to yield particles having an approximate mean size of 50 microns.

After preparation, all the ingredients 1-5 disclosed hereinabove were dried in the dark for five days in a dessicator containing anhydrous sulfuric acid. The ingredients 1-5 were then thoroughly mixed together in the following composition of weight ratios: 10 parts of silver bromide, 2 parts of silver nitrate, 0.5 parts of Manganese Acetate, 10 parts Glucose and 0.01 part Luminol. The mixture of ingredients 1-5 was homogenously distributed on the surface of a Petri dish (15 centimeters in diameter) at an area density of 50 mg/cm$^2$ to form a cell-separating matrix. To pre-sensitize the matrix, several droplets of Hydrogen peroxide ($H_2O_2$) were manually evenly distributed on the surface of the matrix (approximately 0.1 microliters of $H_2O_2$ per square centimeter of dry matrix). The ready-to-use Petri dishes containing the photosensitive matrix were wrapped within black paper and stored in a dessicator in the darkness under dry conditions.

Preparation of Polyacrylamide/AgBr Matrix on Membrane for Sorting of Peroxidase-labeled Cells The matrix is prepared as follows: 4 milliliters of 20% polyacrylamide, 6 milliliters of 30% acrylamide/bisacrylamide (19:1) (BioRad), 2 milliliters of a 10% $AgNO_3$ solution, 2 milliliters of 8% aqueous KBr solution, 50 microliters of 10% TEMED and 100 microliters of 10% ammonium persulfate (APS), were mixed in the dark to form a sol. A cellulose nitrate membrane (Commercially available from Schleicher & Schuell, as Cat. No. 10401169) is immersed in the freshly prepared sol to absorb the sol, and is inserted between two glass plates or between two plastic sheets to allow polymerization of the sol for approximately 20-30 minutes. After polymerization, the membrane is removed, washed thoroughly with water and inserted into a membrane holder that seals the membrane's rims between two plastic cylinders.

Figure 15:
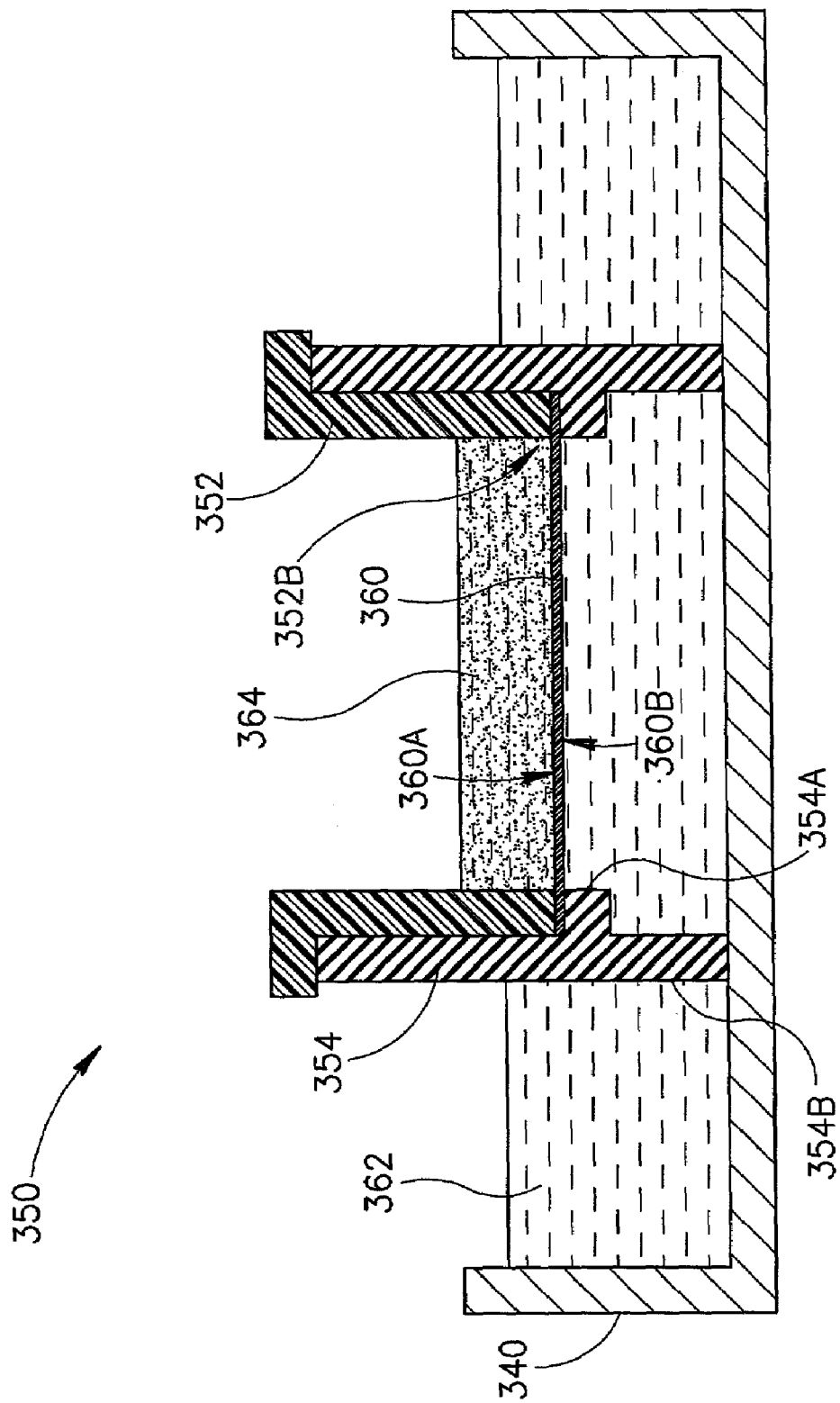
FIG. 15 is a schematic cross sectional view of a holder usable for holding photosensitive matrix impregnated membranes, in accordance with another exemplary embodiment of the present invention.

Reference is now briefly made to FIG. 15 which is a schematic cross sectional view of a holder usable for holding photosensitive matrix impregnated membranes, in accordance with an exemplary embodiment of the present invention.

The membrane holder 350 includes a first cylindrical member 352 and a second cylindrical member 354. A circular photosensitive matrix impregnated membrane 360 may be placed within the second cylindrical member 354 such that the lower surface 360B of the rim of the membrane 360 contacts an annular portion 354A of the second cylindrical member 354. The first cylindrical member 352 may be inserted within the second cylindrical member 354 such that the end 352B of the first cylindrical member 352 is in contact with the upper surface 360A of the rim of the membrane 360.

Due to the tight seal between the membrane 360, the annular portion 354A, and the end 352B of the first cylindrical member 352, the holder 350 may be placed in a vessel 340 and a first solution 362 may be added to the vessel 340 such that the solution 362 is in contact with the lower surface 360B of the membrane 360. The first solution 362 may freely access the lower surface 360B through suitable openings (not shown in the cross-sectional view of FIG. 15) in the lower portion 354B of the second cylindrical member 354.

A second solution 364 may be placed within the first cylindrical member 352 such that the second solution 364 is in contact with the upper surface 360A of the membrane 360. This second solution 364 may be a suspension of cells (cells not shown) which are to be sorted. After sedimentation, cells or other particles (not shown) may come in contact with the upper surface 360A of the membrane 360.

The solution 364 is separated from the solution 362 due to the tight seal between the membrane 360, the annular portion 354A, and the end 352B of the first cylindrical member 352. The solutions 362 and 364 do not physically mix with each other. Solutes included in the solution 362 may, however, diffuse through the matrix impregnated within the membrane 360 to reach the upper surface 360A of the membrane 360. Such solutes may include, inter alia, any of the developer substances disclosed in detail hereinabove and hereinafter, or any other desired substances.

The first cylindrical member 352 and the second cylindrical member 354 may be made from a plastic material such as but not limited to Teflon® or Nylon®, or the like, but may also be made of any other suitable material or substance, such as, but not limited to, organic polymers, or any other suitable materials (provided that the particles or cells to be separated do not adhere or become otherwise attached to the walls of the cylinder members).

The membrane holder 350 is placed inside a 90 millimeters diameter Petri dish and the peroxidase-labeled cells suspended in 5 milliliters PBS containing 2.5 mM luminol and 0.4 mM p-coumaric acid (prepared as disclosed in detail hereinafter) are placed on the upper side of the matrix membrane. The cell suspension is placed on the matrix in the dark. The cells are allowed to sediment towards the membrane for 15 minutes. After cell sedimentation, 35 milliliters of 1.25% $H_2O_2$ in DDW are added to the Petri dish and allowed to diffuse and react for 5 minutes.

The $H_2O_2$ solution is then carefully removed from the Petri dish by vacuum suction to avoid turbulence in the solution overlying the membrane. After the removal of the $H_2O_2$ solution, a developer solution comprising 35-45 milliliters of Phenidone/ascorbic acid sodium salt/Tris-base composition (prepared as disclosed in detail in EXPERIMENT 12 hereinafter) is added to the Petri dish for a 15 minutes development period. During the development period solutes may diffuse upward through the membrane while forming silver grains causing the selective adherence of cells to the matrix as disclosed in detail hereinabove. After the development period, the developer solution is discarded, and the surface of the matrix is thoroughly washed with a 2% solution of sodium dodecylsulphate in a mixture of water, 1-butanol, and ethanol (1:5:2 by volume, respectively). The membrane is then thoroughly washed with DDW. The cells attached to the matrix are collected by n-hexane. The cells collected in hexane are then applied to a microscope slide and the hexane is allowed to evaporate. The cells may then be counted under a microscope.

Preparation of Ca-alqinate Matrix on Membrane and Methods of Cells Processing Using Ca-alqinate Matrix The matrix preparation starts by adding 2 grams of Na-alginate and 10 milligrams of gelatin to 100 milliliters of DDW. Dissolution is carried out at 37° C. overnight. After filtration through a 0.2 micron filter, the warm solution is added to a cellulose nitrate membrane (Schleicher & Schuell, Cat. No.10401169) and allowed to impregnate the membrane for 15-20 minutes. During the impregnation period, the membrane is covered tightly with a glass slide. The glass-covered membrane is then placed in a Petri dish containing 0.5M $CaCl_2$ solution and left to polymerize for 30 minutes. After the polymerization, the glass slide is removed and the membrane is washed gently with DDW in a Petri dish and inserted into a membrane holder that seals the membrane's rim (the holder is disclosed in detail in FIG. 15 below).

Upon immersion of the membrane holder into a fluid in a Petri dish, solutes may now diffuse through the membrane. The following steps of the procedure are performed in the dark. The device is immersed serially in different aqueous solutions as follows: first, 0.1% $AgNO_3$ for 30 minutes, then washed with DDW, followed by 0.5M $CaCl_2$ solution for 30 minutes, then washed with DDW, followed by 0.1% $AgNO_3$ for 30 minutes, then washed with DDW again, 0.5M $CaCl_2$ solution for 30 minutes, and finally two DDW washes (for 30 minutes each wash).

For cells attachment or selection, a suspension including fixed cells is layered by pippetting on the surface of the above described alginate matrix. If the cells are unlabeled and need to be attached nonspecifically to the matrix, the cells are added suspended in Tris buffer or in DDW and the rest of the procedure is continued in ambient light conditions. If, however, only cells that are labeled with peroxidase have to be attached to the matrix, the cells are added suspended in 1 milliliter of 2.5 mM luminol, 0.4 mM p-coumaric acid and 100 mM Tris (at pH=8.5), and the rest of the procedure is continued in the dark.

The cells in both cases (labeled and non-labeled) are allowed to sediment towards the membrane (placed in a membrane holder) for 20 minutes. In the case of peroxidase-labeled cells, the emission of light is initiated by the addition of 0.003% $H_2O_2$ in 100 mM Tris at pH=8.5 to the Petri dish in which the holder is positioned (without introducing excessive turbulence within the liquid layered on the upper surface of alginate impregnated membrane), allowing the solution to contact the lower surface of the matrix such that solutes in the solution diffuse through the alginate impregnated membrane, and to reach the luminol/p-coumaric acid containing solution contacting the upper surface of the alginate impregnated membrane, and the peroxidase-labeled cells which are immersed in this solution.

The Petri dish including the membrane holder, the $H_2O_2$ containing solution, the alginate impregnated membrane, and the luminol/p-coumaric acid containing solution contacting the upper surface of the alginate impregnated membrane are further incubated (in the dark) for a specified incubation time period (the specific duration of the incubation periods used in the experiments is disclosed hereinbelow for the specific experiments performed). The matrix in both cases in now ready for the development step.

The flask in which the holder is immersed is washed twice with DDW, while avoiding turbulence of the cells above the membrane. Next, a developer solution is added to this flask for 20 minutes during which solutes in the developer solution may diffuse into the membrane while forming silver grains that are strongly attached to the matrix and the cells as disclosed in detail hereinabove.

The developer solution is obtained by mixing liquid D-19 developer (commercially available from Kodak) with an equal volume of 0.5M $CaCl_2$ solution, centrifuging, collecting the supernatant and adjusting the pH of the collected supernatant to 7.2 (with HCl).

Alternatively, a phenidone/ascorbic acid/TRIS base composition (prepared as disclosed in detail in EXPERIMENT 12 hereinafter) may be used as a developer.

The developer solution is then discarded, and the surface of the matrix is dissolved, using 1 milliliters of 0.5M sodium-citrate solution. The washing sodium citrate solution with the collected cells is transferred into a test tube. The collected cells may then be counted by a fluorescence microscope either directly as collected or after centrifugation (10 minutes, at 1500 rpm) and resuspension in a smaller volume.

EXPERIMENT 6

Separation of Cells Using the Photoactive Glucose/AgBr/luminol Matrix

Four different tests (tests 1-4) were performed in EXPERIMENT 6. The glucose/AgBr/luminol matrix used in all four tests was prepared as disclosed in detail hereinabove. For each test a primary cell mixture was prepared which included a mixture of EL4 and BW cells. Each of the four tests 1-4 was performed using a different primary mixture. Each of the four primary cell mixtures had a different random ratio of EL4 to BW cells. In each of the tests 1-4, two samples of cells were prepared from the primary cell mixture used. The first sample of each test contained approximately $1 \times 10^6$ cells taken from the primary cell mixture that were pre-stained with the CFDA-SE kit and fixed with 4% paraformaldehyde as disclosed in detail hereinabove. The stained fixed cells were further labeled with peroxidase by incubating them with 1 microliter cholera-toxin-peroxidase (Calbiochem) in 1 milliliter of PBS for 30 minutes at 4° C. These cells are referred to as labeled cells (target cells). The second sample of each test contained $\sim 1 \times 10^7$ cells (taken from the same primary cell mixture from which the first sample was prepared) that were fixed with 4% paraformaldehyde. These cells are referred to as unlabeled cells (non-target cells).

The tested sample of each of the tests 1-4 was prepared by mixing 100 (one hundred) of the labeled cells (of the first sample) with $10^7$ of the unlabeled cells (of the second sample) in 10 milliliters of a solution of 1.25 mM luminol, 0.2 mM p-coumaric acid, 0.1M Tris-HCl buffer (pH=8.5), and by adding 0.1 milliliter of 30% $H_2O_2$ solution to the resulting mixed cell suspension and mixing the cell suspension.

One minute after the addition of the $H_2O_2$ solution, the entire mixed cell suspension sample was spread in the darkroom on top of the photosensitive glucose/AgBr/luminol matrix and left to react with the matrix for 20 minutes. At the end of the 20 minutes reaction period, 10 milliliters of a luminescence quencher (composed of 4% formaldehyde in a 10% (v:v) ethanol/water solution) was added to the Petri dish for 5 minutes under agitation.

A development quencher (including 10 milliliters of 0.03M solution of HCl in 10% (v:v) 1-butanol/water mixture) was then added to the Petri dish for 5 minutes under agitation to terminate the development. Finally, the matrix was thoroughly washed in a bath filled with a solution comprising 2% SDS in a mixture of water, butanol and ethanol (1:5:2 by volume, respectively) to remove unbound cells from the matrix. The attached cells were subsequently released from the matrix and collected, by washing the matrix with 10 milliliters of n-hexane. The hexane containing the collected cells was applied to the surface of a microscope slide and the hexane was allowed to evaporate. The cells on the microscope slide were stained with DAPI and counted under a Microscope.

The numbers of cells recovered from the matrix in the four different tests 1-4 of EXPERIMENT 6 are given in TABLE 1 below:

TABLE 1

| TEST No. | Number of labeled cells Collected (target cells) | Number of non-labeled cells collected (contaminating cells) |
| --- | --- | --- |
| 1 | 37 | 100 |
| 2 | 97 | 40 |
| 3 | 53 | 60 |
| 4 | 89 | 54 |

The results of EXPERIMENT 6 given in TABLE 1 above demonstrate that the methods of cell purification of the invention as implemented using a photosensitive matrix prepared as disclosed hereinabove, efficiently disposes of the vast majority of non-target cells (non-labeled cells) of the cell mixture while collecting approximately 40-90% of the target cells (the labeled cells) in cell mixtures having a ratio of $10^2/10^7$ of target cells to non-target cells, respectively.

EXPERIMENT 7

$10^6$ EL4 cells were stained with the CFDA-SE kit and fixed with 4% paraformaldehyde as disclosed in detail hereinabove. 1 microliter of cholera-toxin-peroxidase (Calbiochem) was added to these cells suspended in 1 milliliter of PBS. Two hundred (200) of these stained, fixed and peroxidase-labelled cells were mixed with $2 \times 10^6$ fixed unstained, unlabeled EL4 cells in a 15 ml polypropylene tube. The cells were then suspended in 5 milliliters of PBS containing 2.5 mM luminol, and 0.4 mM coumaric acid and transferred onto a previously prepared undeveloped polyacrylamide/AgBr matrix in the dark and processed for attachment and detachment as disclosed in detail in the section entitled "Preparation of Polyacrylamide/AgBr matrix on membrane for sorting of peroxidase-labeled cells" hereinabove. The cells were detached with n-hexane, and placed on microscope slides as disclosed herewinabove. After the evaporation of the hexane, the cells were viewed under the microscope, using the fluorescent and non-fluorescent modes of the microscope.

The numbers of cells collected from the Polyacrylamide/AgBr matrix and stained by DAPI and by CFDA-SE as visually counted in three different microscope fields of view, and the calculated cell purity (computed as the percent of CFDA stained cells out of the DAPI stained cells) are given in TABLE 2 below.

TABLE 2

| Visual field number | Number of DAPI-stained cells counted in the visual field | Number of CFDA-stained cells counted in the visual field | % purity of sorted cells |
| --- | --- | --- | --- |
| 1 | 24 | 20 | 83% |
| 2 | 22 | 21 | 95% |
| 3 | 35 | 30 | 86% |

The results of EXPERIMENT 7 demonstrate that the cell separation or sorting method of the present invention may be applied for separating a target cell population from a non-target cell population, and that relatively high purity of the separated target cells may be achieved at a ratio of approximately 1:20,000 of target cells to non-target cells.

EXPERIMENT 8

Selection of Cells, Using Peroxidase and Ca-alqinate/AgBr Matrix

In the experiment, fluorescently-stained HH cells were used as the target cells, and BW cells were used as the non-target cells. The target HH cells were distinguished from the non-target BW cells by the fluorescence of the CFDA-SE staining the HH cells. The yield and purity of the isolated cells could then be evaluated by visual observation under a fluorescence microscope.

HH cells were stained with the CFDA-SE staining kit and fixed with 4% paraformaldehyde, as disclosed in detail hereinabove. Approximately 2200 of the fluorescently-stained and fixed HH cells were mixed with $10^6$ paraformaldehyde fixed BW cells in a 15 ml PMP tube and centrifuged for 5 minutes at 400 g. The pellet of the fixed cells was resuspended in 100 µl of 1% BSA, 20 mM Tris, 150 mM NaCl, pH=7.4 containing mouse-anti-human-CD3ε IgG conjugated to horseradish-peroxidase (Santa Cruz, Cat. No. sc-1179 HRP) diluted 1:40,000. After a 1 hour incubation (with rotation) at room temperature, each tube was centrifuged for 5 minutes at 400 g, 4° C. and the cells were washed with 3 milliliters of 1% BSA, 20 mM Tris, 150 mM NaCl, pH=7.4 and centrifuged again as before. This wash was repeated twice more.

The cells were then resuspended in 1 milliliter of 2.5 mM luminol, 0.4 mM p-coumaric acid and 100 mM Tris (at pH=8.5), transferred to a previously prepared undeveloped alginate/AgBr matrix in the dark and processed for attachment and detachment as described in detail hereinabove in the section entitled "Preparation of Ca-alginate matrix on membrane and methods of cells processing using Ca-alginate matrix". The collected detached cells were suspended in PBS and visually counted under the microscope, using the fluorescent and non-fluorescent modes of the microscope.

1980 cells were recovered from the matrix. All of the recovered cells were stained in green, indicating that they were all HH cells. Thus, a 90% yield and 100% purity of the selected population was achieved in the selection of 2200 target cells from a population of approximately $10^6$ non-target cells.

EXPERIMENT 9

Performing a CD3+/CD4+ T-cells Count

In HIV infection, the CD4+ T-cells count and the CD8+ T-cells count are the most commonly utilized laboratory indicators for clinical prognosis, therapeutic monitoring and entry criteria for clinical trials. Currently, the quantitative measurements of these cells involves three distinct measurements. Two of these measurements, the white blood cells (WBC) count, and the lymphocytes percent, are typically performed by automated hematology instrumentation, while the third measurement which determines the CD4+ T-cells percent and the CD8+ T-cells percent are performed by flow cytometric immuno-phenotyping.

As an alternative to the above described method, WBC may be isolated from a sample of whole blood, counted, and attached to a surface that can be viewed under the microscope. The CD4+ T-cells subpopulation may, then, be distinguished from other bound white blood cells according to the simultaneous presentation of both CD3 and CD4 markers on their surfaces and the CD8+ T-cells may be recognized according to the simultaneous presentation of both CD3 and CD8 markers on their surfaces, if a previous labeling with fluorescently-labeled relevant antibodies was carried out.

This experiment demonstrates a quantitative determination of the percentage of CD3/CD8 cells out of the lymphocytes and monocytes fraction of the WBC.

Lymphocytes and monocytes may be isolated from rest of the cells in whole blood by a density gradient as is known in the art. The collected lymphocytes and monocytes may then be fixed and incubated with antibodies specific to CD8 conjugated to one fluorescent dye and with antibodies specific to CD3 conjugated to another fluorescent dye. Afterwards, the entire sample of cells may be attached to one of the photosensitizable matrices of the present invention by photosensitization under ambient light conditions. The cells may be stained (on the matrix) with a third fluorescent substance that dyes the nuclei of all cells in the sample. The matrix may then be viewed by a fluorescent microscope, which enables the selective detection of each of the three dyes used.

The percentage of cells expressing both CD3 and CD8 from the lymphocytes and monocytes population may then be evaluated from counting cells dyed by different fluorescent colors. The cell counting may be performed in several microscopic fields of view, in order to obtain a more reliable result. The absolute number of CD3/CD8 cells may further be calculated by multiplying the averaged percentage of these cells by the absolute initial number of the lymphocytes and monocytes.

A citrate-treated blood sample taken from a healthy donor were diluted 1:2 with PBS, layered on top of Histopaque 1077 gradient (Sigma, Cat. No. 1077-1) and centrifuged at 700 g for 30 minutes at 21° C. The white blood cells (WBC) recovered from the formed ring were washed twice with PBS and fixed with 4% paraformaldehyde as disclosed in detail hereinabove. $10^6$ of the fixed WBC cells were resuspended in 50 microliters of 1% BSA in PBS containing 0.3 micrograms mouse-anti-human CD3 (Becton Dickinson, Cat. No. 347340) and incubated for 30 minutes at 4° C. After a single wash with 1 milliliter 1% BSA in PBS, the cells were suspended in 100 microliters of 1% BSA in PBS containing anti-mouse-IgG conjugated to Alexa Fluor 488 (Molecular Probes, USA, Cat. No. A-11029) diluted 1:300, and incubated for 30 minutes at 4° C. After washing with 1 milliliter of PBS, the cells were suspended in 50 microliters of 1% BSA in PBS containing 0.5 micrograms of mouse-anti-human CD8 antibody (Becton Dickinson, Cat. No. 346310), and incubated for 30 minutes at 4° C. After a single wash with 1 milliliter of 1% BSA in PBS, the cells were suspended in 100 microliters of 1% BSA in PBS containing anti-mouse-IgG conjugated-to-Cy3 (Jackson) diluted 1:700, and incubated for 30 minutes at 4° C.

After washing with 1 ml PBS, the cells were suspended in 1 milliliter of PBS and spread on top of a previously prepared undeveloped polyacrylamide/AgBr matrix on a membrane in the dark. The polyacrylamide/AgBr matrix on a membrane was prepared as disclosed in detail hereinabove in the section entitled "Preparation of Polyacrylamide/AgBr matrix on membrane for sorting of peroxidase-labeled cells".

The Polyacrylamide/AgBr matrix on the membrane was exposed to ambient light in the room and further processed to attach the whole population of cells that was transferred to it, using the GBX developer (Kodak) diluted 1:6 with DDW for development, as disclosed in detail hereinabove. After development and washing, the membrane was released from the holder, stained with DAPI (which dyes the nuclei of all cells attached to the matrix) and viewed under the fluorescent microscope, using three different filters. The differently-dyed cells were counted in two microscope fields of view.

The filters used for viewing the cells were filter set 09 (used for FITC, and Alexa Fluor 488 viewing), filter set 15 (used for Cy3 viewing), and filter set 02 (used for DAPI viewing). All the above indicated filter sets are commercially available from Zeiss, Germany.

Results for First Field of View

The number of blue stained cells (all cells after gradient) in the first field of view was 36.

The number of cells stained in both green and in red(CD3/CD8 cells) in the first field of view was 4 cells.

The percentage of CD3/CD8 cells from all cells after gradient in the first field of view was 11%.

Results for the Second Field of View

The number of blue cells (all cells after gradient) in field 2 was 44.

The number of cells stained both in green and in red(CD3/CD8 cells) in field 2 was 7 cells.

The percentage of CD3/CD8 cells from all cells after gradient in field 2 was 16%.

The averaged percentage of CD3/CD8 cells from all cells after gradient was 14%.

The tight non-specific binding of all cells of a sample to the matrix surface enables the counting of all cells or of only certain cells if those were specifically labeled in advance, with one or more fluorescent dyes. The counting can be performed in selected field(s) or in the entire matrix. This method can be applied to $CD4^+$ T-cells and $CD8^+$ T-cells counting as well as to other research and clinical applications.

Detection of Abnormal Amounts of Red Blood Cells (RBC's) in Urine.

Normally, a healthy person may have up to 2-3 RBC's per microliter of urine. Larger numbers may indicate a medical problem. It may be possible to apply the photosensitization based cell attachment to light sensitive matrices of the present invention for counting the number of RBCs in urine.

EXPERIMENT 10

In this experiment an abnormal condition of 10 RBC's per microliter of urine (which is equivalent to $5 \times 10^5$ cells per 50 milliliters of urine) was artificially simulated.

RBC's were isolated from 3 milliliters of blood of a healthy donor by centrifugation for 10 minutes at 400 g. 1 milliliter of the erythrocyte mass was diluted with 4 milliliters of PBS and underwent fixation with 4% paraformaldehyde, as disclosed hereinabove. Approximately $4.9 \times 10^5$ of the fixed red blood cells were suspended in 50 milliliters of urine taken from a healthy donor. The urine including the fixed RBCs was centrifuged for 15 minutes at 400 g. The pellet (containing approximately $4.1 \times 10^5$ cells) was next fluorescently labeled by incubating the pellet for one hour with 0.05 micrograms of mouse-anti-human-Glycophorin-A conjugated to FITC (commercially available from Dako A/S, Germany, as Cat. No. F-0870) in 50 microliters of 1% BSA in PBS.

The antibody labeled red blood cells were washed three times with 1 milliliter of 1%BSA in PBS and the antibodies were fixed to the cells by incubation for 30 minutes in 0.8% paraformaldehyde fixative. After washing with 1 milliliter PBS, the cells were suspended in 1 milliliter of PBS and spread on top of a previously prepared undeveloped polyacrylamide/AgBr matrix prepared in the dark on a nitrocellulose membrane and held in a membrane holder, as disclosed in detail hereinabove. The membrane was exposed to ambient light conditions in the room and further processed to attach the whole population of cells that was transferred onto it, using GBX developer diluted 1:10 for development, as disclosed in detail hereinabove. After development and washing, the polyacrylamide/AgBr matrix impregnated membrane was released from the holder and viewed under a fluorescence microscope, and the fluorescent cells were counted.

The number of fluorescent cells that were attached to the supporting matrix was $4 \times 10^5$ cells. Thus, about 82% of the RBC's originally mixed with the urine were finally counted on the polyacrylamide/AgBr matrix impregnated membrane.

It is therefore concluded that the method described herein for cell attachment is sensitive enough to be applied for the detection of abnormal amounts of red blood cells in urine. For practicing such a diagnostic test, the urine sample will have to undergo centrifugation and fixation of all cells in the resulting pellet.

Cell Viability and Proliferation

The cell viability and proliferative properties of cells separated by the methods of the present invention may depend, inter alia, on the particular separation methods, and on the chemical composition of the matrix, the developer and of other solutions which may be used during the separation or sorting procedures.

Therefore, different developer compositions were evaluated with respect to their effects on cell viability and proliferative properties in experiments 11-16 hereinbelow.

EXPERIMENT 11

Cell Viability and Proliferation After a Brief Cell Exposure to a $FeCl_2$/Tris/Glycine Developer The experiment was performed to test the survival and further proliferation of the BW cell line following exposure to a $FeCl_2$/Tris/Glycine developer.

Two equal volumes of BW cells suspended in tissue culture medium were centrifuged for 5 minutes at 400 g. One of the resultant pellets was suspended in 1 milliliter of the growing medium of these cells (this pellet served as the control sample).

The growing medium for the BW cells included 10% fetal calf serum (FCS), 1% (100×) antibiotic-antimycotic (commercially available from Sigma-Aldrich Israel Ltd., as Cat. No. A9909), and 2 mM L-glutamine (commercially available as a 200 mM solution from Sigma-Aldrich Israel Ltd., as Cat. No. G7513) in Roswell Park Memorial Institute (RPMI) 1640 growth medium (commercially available from Sigma-Aldrich Israel Ltd., as Cat. No. R-8758).

The second pellet was suspended in 1 milliliter of a specially formulated developer (prepared by mixing 5 milliliters of Tris-Glycine (×10) from BioRad, USA, 50 milligrams $FeCl_2.4H_2O$ and 5 milliliters $H_2O$, adjusting pH to 7.5 and sterile filtering through a 0.2 micrometer membrane). Immediately after suspension in the developer, both samples were centrifuged for 5 minutes at 400 g at 4° C. and washed twice with 1 milliliter of the culture growing medium. Each wash was followed by a centrifugation of 5 minutes at 400 g at 4° C. The washed pellets were suspended each in 2 milliliters of culture growing medium and transferred to a tissue culture flask from which representative aliquots were aspirated for counting by a hemacytometer. Viability of cells was determined by the addition of trypan blue dye to the counted samples, as is known in the art. The flasks were inserted into the incubator for subculturing and were allowed to grow for 3 days. Each day, aliquots were taken for viable cells counting from both of the flasks.

The results of EXPERIMENT 11 are given in TABLE 3 below.

TABLE 3

| Days After Treatment | Number of Viable cells in developer treated sample (DEV) | Number of Viable cells in control sample (MED) | DEV/MED Ratio (%) |
|---|---|---|---|
| 0 | 3,460,000 | 4,220,000 | 82% |
| 2 | 9,250,000 | 10,950,000 | 84% |
| 4 | 13,800,000 | 13,000,000 | 106% |

The data in the fourth column of TABLE 3 represents the Number of Viable cells in developer treated sample divided by the Number of Viable cells in the control sample and multiplied by 100.

The results shown in Table 3 indicate high survival and proliferation rates of the cells in the sample exposed to the $FeCl_2$/Tris/Glycine developer as compared to the cells in the control sample.

EXPERIMENT 12

Cell' Viability and Proliferation After a Period of Exposure to a Phenidon/ascorbic Acid/Tris Developer Two aliquots of $2\times10^6$ EL4 cells in tissue culture were centrifuged for 5 minutes at 400 g. One of the resulting two pellets was suspended for 10 minutes at room temperature in 1 milliliter of the culture growing medium of these cells (this pellet served as the control sample).

The growing medium for the EL4 cells included 10% fetal calf serum (FCS), 1% (100×) antibiotic-antimycotic (commercially available from Sigma-Aldrich Israel Ltd., as Cat. No. A9909), and 2 mM L-glutamine (commercially available as a 200 mM solution from Sigma-Aldrich Israel Ltd., as Cat. No. G7513) in Roswell Park Memorial Institute (RPMI) 1640 growth medium (commercially available from Sigma-Aldrich Israel Ltd., as Cat. No. R-8758).

The second pellet was suspended for the same time in 1 milliliter of a developer (prepared by mixing 30 milligrams Trizma Base, 5 milligrams Phenidon, 50 milligrams ascorbic acid and 10 milliliters of $H_2O$, adjusting pH to 7.5, and sterile filtering through a 0.2 micron membrane). Both samples were then centrifuged for 5 minutes at 400 g at 4° C. and washed twice with 1 milliliter aliquots of the culture growing medium. Each wash was followed by a centrifugation of 5 minutes at 400 g at 4° C. The washed pellets were suspended each in 2 milliliters of culture growing medium and transferred to a tissue culture flask from which representative aliquots were aspirated for counting by a hemacytometer. The flasks were inserted into the incubator for subculturing and were allowed to grow for 3 days. Each day, aliquots were taken for cells counting from both of the flasks. A similar procedure was performed with cells of the BW cell line. The results for the BW cells, and EL4 cells are shown in TABLE 4 and TABLE 5, respectively, below.

TABLE 4

| Days After Treatment | Number of Viable BW cells in control sample | Number of Viable BW cells in developer treated sample |
|---|---|---|
| 0 | 1,500,000 | 1,400,000 |
| 1 | 4,000,000 | 5,000,000 |
| 2 | 8,400,000 | 9,200,000 |
| 3 | 12,000,000 | 13,000,000 |

TABLE 5

| Days After Treatment | Number of Viable EL4 cells in control sample | Number of Viable EL4 cells in developer treated sample |
|---|---|---|
| 0 | 2,800,000 | 2,600,000 |
| 1 | 8,100,000 | 7,800,000 |
| 2 | 11,000,000 | 12,000,000 |
| 3 | 41,000,000 | 42,000,000 |

The results shown in TABLE 4 and TABLE 5 above indicate high survival and proliferation rates of BW cells and EL4 cells, respectively, in the sample exposed for 10 minutes to the phenidon/ascorbic acid/Tris developer solution as compared to the cells in the control sample.

EXPERIMENT 13

Cell Viability and Proliferation in a $K_3(Fe(CN)_6)$/$NH_4SCN$ Silver Dissolving Solution Two aliquots of $2\times10^6$ EL4 cells in tissue culture were centrifuged for 5 minutes at 400 g, at 4° C. One of the two resulting pellets was suspended in 1 milliliter of the culture growing medium of these cells, while the other pellet was suspended in 1 milliter of a silver dissolving solution (This solution may be usable for removing silver grains attached to the cells). The silver dissolving solution comprises 0.1% $K_3(Fe(CN)_6)$, and 0.2% $NH_4SCN$ in DDW at pH 6.7 that was sterile filtered through a 0.2 micron membrane. Both samples were immediately centrifuged for 5 minutes at 400 g at 4° C. and washed twice with 1 milliliter aliquots of the growing medium. Each wash was followed by a centrifugation for 5 minutes at 400 g. The washed pellets were suspended each in 2 milliliters of growing medium and transferred to a tissue culture flask from which representative aliquots were aspirated for counting by a hemacytometer. The flasks were inserted into the incubator for subculturing and were allowed to grow during 3 days. Each day, aliquots were taken for cells counting from both of the flasks.

A similar procedure was performed with cells of the BW cell line.

The results for the BW cells, and EL4 cells are shown in TABLE 6 and TABLE 7, respectively, below.

TABLE 6

| Days After Treatment | Number of Viable BW cells in control sample | Number of Viable BW cells in sample treated with silver dissolving solution |
|---|---|---|
| 0 | 1,640,000 | 2,040,000 |
| 1 | 3,400,000 | 2,900,000 |

TABLE 6-continued

| Days After Treatment | Number of Viable BW cells in control sample | Number of Viable BW cells in sample treated with silver dissolving solution |
|---|---|---|
| 2 | 7,300,000 | 7,600,000 |
| 3 | 18,600,000 | 20,000,000 |

TABLE 7

| Days After Treatment | Number of Viable EL4 cells in control sample | Number of Viable EL4 cells in sample treated with silver dissolving solution |
|---|---|---|
| 0 | 2,280,000 | 2,520,000 |
| 1 | 7,600,000 | 6,800,000 |
| 2 | 16,000,000 | 17,000,000 |
| 3 | 44,000,000 | 37,000,000 |

The results shown in TABLE 6 and TABLE 7 above indicate high survival and proliferation rates of BW cells and EL4 cells, respectively, in the sample exposed for 5 minutes to the $K_3(Fe(CN)_6)/NH_4SCN$ solution as compared to the cells in the control sample.

Thus, the $K_3(Fe(CN)_6)/NH_4SCN$ solution described herein may be used for dissolving developed silver grains attached to viable or fixed cells (or to other particles which are being separated) without deleteriously affecting the viability and proliferation of cells.

The silver dissolving solution may thus be used to remove or dissolve silver grains attached to cells or particles which were detached from the photosesitizable substrate using enzyme based cell detaching methods, as disclosed hereinabove, such as, but not limited to, pepsin treatment, or papain treatment, or trypsin treatment, or the like, or cells or particles which were detached from the photosesitizable substrate using other detachment methods, such as but not limited to the dissolving of the matrix or a portion thereof by matrix depolymerization (as in the case of alginate based matrices disclosed hereinabove).

For example, when using alginate based matrices as disclosed herein, the target cells or particles may be detached from the alginate based matrix by dissolving the matrix itself or a part thereof using sodium citrate or other suitable calcium sequestering agents solution to remove the calcium ions. In such a case, the collected target particles or cells may have silver grains attached thereto. The $K_3(Fe(CN)_6)/NH_4SCN$ solution described hereinabove, may thus be used to detach the silver grains from the separated target particles or cells.

It is noted that other suitable metal dissolving solutions formulated for dissolving different metal grains different than silver metal grains may be used in cases were the light sensitive matrix comprises photosensitizable metal compounds other than silver compounds.

EXPERIMENT 14

Viability of Cells Detached from the Matrix and of the Washed Out Cells

Two Ca-alginate matrices on cellulose nitrate filters were prepared and placed within holders as disclosed in detail hereinabove, in the section entitled "Preparation of Ca-alginate matrix on membrane and methods of cells processing using Ca-alginate matrix".

Three pellets each containing $4 \times 10^6$ EL4 cells were prepared by centrifugation (5 minutes at 400 g) from a 100% viability cells suspension (as determined by the trypan blue method, as is known in the art). The cells in one of the pellets were suspended in 1 milliliter of PBS and were kept on ice (sample 3) for the entire duration of the experiment. Sample 3, thus served as the control sample of non-treated cells.

The two other pellets were each suspended in 1 milliliter of PBS to form samples 1 and 2. Samples 1 and 2 were placed in two separate holders, as disclosed hereinabove, such that each sample was in contact with the upper surface of the alginate matrix held in the holder. In both samples 1 and 2, the cells were allowed to sediment towards the alginate matrix for 20 minutes. After the sedimentation period ended, the holder including sample 1 was exposed to ambient light conditions, while the holder including sample 2 remained in the dark.

For development of both samples, the flask in which the holder was immersed was washed twice with DDW, while avoiding turbulence of the cells above the membrane. Next, a Phenidon/ascorbic acid/Tris developer (prepared as disclosed in detail in EXPERIMENT 12 hereinabove) was added to the flasks in which the two holders were positioned such that the developer solution was in contact with the lower surface of each of the alginate matrices of the membranes. The holders were left in the developer solution for 15 minutes during which solutes in the developer solution could diffuse upward through the membrane and form silver grains (in the light exposed sample 2) that strongly attach the cells to the alginate matrix. The developer solution was then discarded.

In sample 2 (the sample which was not exposed to light), the cells were collected at this point from the alginate matrix by washing with PBS.

In sample 1 (the sample which was exposed to light for inducing attachment), in contrast, the surface of the matrix was washed with PBS and then 1 milliliter of 0.5 mM EDTA solution in PBS was placed for 1 minute on the upper surface of the alginate matrix to detach attached cells as disclosed in detail hereinabove. The EDTA/PBS solution including the detached cells was then collected into a PMP tube.

Cells of all samples were centrifuged for 5 minutes at 400 g. The cells of sample 1 were further treated for 2 minutes with the $K_3(Fe(CN)_6)/NH_4SCN$ silver dissolving solution (prepared as disclosed in detail in EXPERIMENT 13 hereinabove), and recentrifuged (for 5 minutes at 400 g). Aliquotes of 20 microliters from each of the samples 1-3 were mixed with 20 microliters of 0.4% trypan blue and the viable cells were counted under the microscope, using a hemacytometer.

The results of EXPERIMENT 14 are shown in TABLE 8 below.

TABLE 8

| SAMPLE NUMBER | CELL VIABILITY (%) | % RECOVERY |
|---|---|---|
| 1 | 72% | 40% |
| 2 | 68% | 95% |
| 3 | 92% | — |

As shown in TABLE 8 above, approximately 70% cell viability may be achieved using the procedure described in this experiment. The recovery of the cells which were not attached to the matrix by development following exposure to light (the cells of sample 2) is higher than the recovery of the cells that were attached to the matrix by development following exposure to light, and then detached from the alginate matrix (sample 1).

It will be appreciated that there are many applications for the cell separation methods of the present invention. For example, one non-limiting clinical application is the separation of fetal erythroblasts from peripheral maternal blood for early diagnosis and screening of Down syndrome of the fetus. In accordance with one preferred embodiment of the present invention, a mixture of cells obtained from peripheral maternal blood may be incubated with a peroxidase conjugate of a specific antibody directed against epsilon globin chains which are expressed in fetal erythroblasts but not in adult maternal erythrocytes.

The peroxidase-antibody conjugate may then specifically bind and label the fetal erythroblasts. The fetal erythroblast cells may then be separated from the maternal cells by sedimenting all the cells on a light sensitive layer as disclosed hereinabove and then performing the development (using the peroxidase/luminol/$H_2O_2$/p-coumaric acid method disclosed in detail hereinabove) and washing stages as disclosed in detail hereinabove. After washing, the purified fetal erythroblasts adhering to the light sensitive layer may be harvested and then analyzed for chromosomal abnormalities using FISH as is known in the art. Alternatively, the purified fetal erythroblasts adhering to the light sensitive layer may be directly processed for FISH and analyzed without removing the separated fetal cells from the light sensitive layer. For example, this may be implemented using microscope slides coated with a light sensitive layer, as disclosed hereinabove.

It is noted that the above disclosed application is given by way of example only and that many other applications may be implemented by suitable modifications of the above disclosed methods for particle or cell separation, such modifications may include but are not limited to, modifications of the specific photophoric probes used (such as, the use of various types of antibody-conjugates, different amplification methods, different antibody sandwich methods, different types of light sensitive layers, different types of the light sensitive metal salts, different methods for inducing the localized producing of light in the vicinity of the target cells or target particles, use of various phosphors such as but not limited to anti-stokes phosphor particles, and up-converting phosphor particles in conjunction with infra-red light irradiation as disclosed hereinabove, and other modifications).

It is further noted that the photophoric probes of the present invention are not limited to probes comprising chemiluminescent, or bioluminescent, or fluorescent moieties or particles or the like, or moieties which catalyze or assist the formation of substances which mediate chemiluminescent or bioluminescent reactions or other different light producing or light emitting reactions or processes in the medium contacting the photosensitive matrix or layer or substrate of the present invention, as disclosed in detail hereinabove. Other different agents may also be used as part of the photophoric probes.

For example, thermoluminescent or electroluminescent agents or particles or moieties or compounds may be included in or may form a part of the photophoric probes usable in the methods and devices disclosed in the present invention. In thermoluminescent materials energy may be stored in a photophoric probe by irradiation or otherwise as is known in the art. The stored energy may be released as photons upon subsequent heating of a photophoric probe including such a thermoluminescent material or phosphor particle or agent.

For example, if the photophoric probe comprises a thermoluminescent part or agent or particle or moiety, the photosensitization of the light sensitive matrix or substrate or layer may be performed by suitably heating or increasing the temperature of the fluid or solution contacting the light sensitive matrix or substrate or layer, or alternatively by heating or increasing the temperature of the light sensitive matrix or substrate or layer, using any suitable heating methods or heating devices known in the art. The increase in temperature may induce the production of light by the thermoluminescent part of the photophoric probe resulting in photosensitization of the light sensitive matrix or layer or substrate in the vicinity of the particles to which the photophoric probe is attached or bound.

In another example, if the photophoric probe comprises an electroluminescent part or agent or particle or moiety, the photosensitization of the light sensitive matrix or substrate or layer may be performed by suitably applying an electrical voltage or field to or accross the light sensitive matrix or substrate or layer, as is known in the art using any suitable heating methods or heating devices known in the art. The application of this electrical field or voltage may induce the production of light by the electroluminescent part of the photophoric probe resulting in photosensitization of the light sensitive matrix or layer or substrate in the vicinity of the particles to which the photophoric probe is attached or bound. A non limiting example for an electroluminescent phosphor which may be used in constructing the photophoric probes of the present invention, are manganese-doped zinc sulfide phosphor particles which are known in the art. It is, however, noted that other suitable types of electroluminescent agents or electrofluorescing materials known in the art may also be used in implementing the probes of the present invention.

It is noted that while the non limiting example of a method of the presence invention utilizes a combination of peroxidase based photophoric probe, and a luminol based chemiluminescence reaction, many other different types of photophoric probes coupled with other different light emitting or chemiluminescent reactions known in the art may be used for implementing the methods of the present invention.

For example, in accordance with another embodiment of the invention, a photophoric probe comprising alkaline phosphatase may be used in conjunction with 1,2 dioxetane based chemiluminescent substrates. Examples of such 1,2 dioxetane based chemiluminescent alkaline-phosphatase substrates are the CDP-Star®, CSPD®, and AMPPD® substrates for alkaline phosphatase, commercially available from Applied Biosystems, CA, U.S.A.

In another example, in accordance with another embodiment of the invention, photophoric probes comprising alkaline phosphatase may be used in conjunction with dioxetane based chemiluminescent alkaline-phosphatase substrates and/or compositions such as, for example, the Lumigen® PPD {4-methoxy-4(3-phosphatephenyl)spyro[1,2-dioxetane-3,2'-adamantane], disodium salt} substrate or the Lumi-Phos® Plus formulation, commercially available from Lumigen Inc., MI, USA.

In another example, in accordance with another embodiment of the invention, a photophoric probe comprising the enzyme galactosidase may be used in conjunction with 1,2 dioxetane based chemiluminescent substrates. Examples of such 1,2 dioxetane based chemiluminescent galactosidase substrates are the Galacton-Star®, Galacton-Plus®, and Galacton® substrates for galactosidase, commercially available from Applied Biosystems, CA, U.S.A.

In another example, in accordance with another embodiment of the invention, a photophoric probe comprising the enzyme β-glucuronidase may be used in conjunction with 1,2 dioxetane based chemiluminescent substrates. An example of such 1,2 dioxetane based chemiluminescent β-glucuronidase substrates is the Glucuron®, substrate for β-glucuronidase, commercially available from Applied Biosystems, CA, U.S.A.

Such substrates may or may not be used with luminescence enhancers, as is known in the art. An example for such luminescence enhancers is the Nitro-Block-II™, commercially available from Applied Biosystems, CA, U.S.A.

Furthermore, the methods of the present invention are not intended to be limited by any of the specific probes or chemiluminescent reactions or chemistries shown in the experiments or disclosed herein. Rather, any suitable light emitting probe, and any suitable probe capable of causing or initiating or catalyzing or otherwise participating in a reaction which produces light may be adapted for use in the methods devices and systems of the present invention, and is considered to be within the scope of the present invention.

Such modifications and variations and of the present invention are considered to be within the scope and spirit of the present invention.

What is claimed is:

1. A method for physically separating cells, the method comprising:
   providing a liquid comprising a living cell mixture suspended therein, wherein said living cell mixture comprises target cells and non-target cells;
   labeling said target cells with a photophoric probe adapted to label said target cells to the exclusion of said non-target cells to form labeled target cells in said liquid, said photophoric probe capable of being controllably activated to produce localized emission of light in the vicinity of said labeled target cells;
   providing a light sensitive substrate comprising a photosensitizable metal compound;
   applying said liquid to said light sensitive substrate such that said labeled target cells are adjacent to said light sensitive substrate;
   activating said photophoric probe to produce localized emission of light in the vicinity of said labeled target cells, said light photosensitizes a portion of said light sensitive substrate to form photosensitized portion of said substrate;
   developing said photosensitized portions, wherein developing comprises applying to said substrate a developing solution formulated to substantially allow said living cells to remain viable after exposure to said developing solution;
   forming metal grains from said metal compound whereby said labeled target cells adhere to said metal grains;
   removing non-target cells of said mixture from the substrate, thereby separating said non-target cells from said labeled target cells adhered to the metal grains.

2. The method according to claim 1, wherein activating said photophoric probe to produce light or to induce the production of light in the vicinity of said labeled target cell comprises using a photoactivation method, a chemical activation method, a thermal activation method or an electrical activation method.

3. The method according to claim 1, wherein said step of activating comprises inducing said photophoric probe to participate in a light producing chemical reaction.

4. The method according to claim 1, wherein said photosensitizable metal compound comprises a photosensitizable metal salt.

5. The method according to claim 4 wherein said photosensitizable metal salt comprises a silver halide.

6. The method according to claim 1, further comprising the step of detaching from said substrate at least one of said labeled target cells adhered to said substrate.

7. The method according to claim 6, further comprising the step of collecting said detached at least one target cell from said substrate.

8. The method according to claim 7, further comprising treating the collected, detached target cell with a metal dissolving solution for dissolving metal grains attached to said collected, detached target cell.

9. The method according to claim 8, wherein said photosensitizable metal compound comprises a photosensitizable silver compound, said metal grains are silver metal grains, and wherein said metal dissolving solution is a solution comprising $K_3Fe(CN)_6$ and $NH_4SCN$.

10. The method according to claim 6, wherein said step of detaching comprises applying a detaching agent to said substrate.

11. The method according to claim 10, wherein said detaching agent is n-hexane, or a solution comprising an enzyme capable of detaching the target cell attached to said substrate.

12. The method according to claim 11, wherein said enzyme is a proteolytic enzyme.

13. The method according to claim 12, wherein said proteolytic enzyme is pepsin, trypsin, papain, or combination thereof.

14. The method according to claim 10, wherein said substrate comprises a polymerized calcium alginate matrix and said detaching agent comprises a solution containing a calcium sequestering agent.

15. The method according to claim 14, wherein said calcium sequestering agent comprises sodium citrate, EDTA, or EDTA salts.

16. The method according to claim 1, wherein said target cells to be separated or sorted, are eukaryotic cells, prokaryotic cells, mammalian cells, non-mammalian cells, viable cells, pathogenic organisms, non-pathogenic organisms, bacterial cells, viruses, nanobacteria, unicellular organisms, or multicellular organisms.

17. A method for physically separating cells, the method comprising:
   providing a liquid comprising a living cell mixture suspended therein, wherein said living cell mixture comprises target cells and non-target cells;
   labeling said target cells with a photophoric probe adapted to label said target cells to the exclusion of said non-target cells to form labeled target cells in said liquid, said photophoric probe capable of being controllably activated to produce localized emission of light in the vicinity of said selectively labeled target cells;
   providing a light sensitive substrate, said substrate comprising a photosensitizable metal compound;
   applying said liquid to said light sensitive substrate such that said labeled target cells are adjacent to, or in contact with, the surface of said light sensitive substrate;
   activating said photophoric probe to produce localized emission of light in the vicinity of said labeled target cells, said light photosensitizes portions of said light sensitive substrate to form photosensitized portions of said substrate;

developing said photosensitized portions, wherein developing comprises applying to said substrate a developing solution formulated to substantially allow said living cells to remain viable after exposure to said developing solution;

forming metal grains in said photosensitized portions from said metal compound whereby said labeled target cells adhere to said metal grains;

separating said non-target cells from said target cells adhered to the metal grains by removing non-target cells from the substrate.

18. The method according to claim 17, wherein said step of activating comprises using a photoactivation method, a chemical activation method, a thermal activation method or an electrical activation method.

19. The method according to claim 17, wherein said step of activating comprises inducing said photophoric probe to participate in a light-producing chemical reaction.

20. The method according to claim 17, wherein said photosensitizable metal compound comprises a silver halide.

21. The method according to claim 20, wherein said silver halide is silver chloride, silver bromide, silver iodide or a combination thereof.

22. The method according to claim 17, wherein said photophoric probe comprises:

a first affinity probe capable of specifically and selectively binding to said target cell or to a second affinity probe bound to said target cell; and a second portion linked to said first affinity probe and capable of being controllably induced to emit light or cause the emission of light in the vicinity of said selectively labeled target cell.

23. The method according to claim 22, wherein said first affinity probe is an antibody, a fragment thereof, a toxin having an affinity for at least a portion of a target cell of said target cells, an oligonucleotide probe, a protein based affinity probe, a glycoprotein based affinity probe, a hapten or molecule having an affinity for at least a portion of said target cell.

24. The method according to claim 22, wherein said second portion of said photophoric probe is a chemiluminescent moiety or agent, a fluorescent moiety or agent, an upconverting moiety, particle or agent, an inorganic two photon upconverting anti-stokes phosphor particle, a two photon upconverting dye, a bioluminescent protein, a bioluminescent molecule, a thermoluminescent moiety, agent or particle or an electroluminescent moiety, agent or particle.

25. The method according to claim 22, wherein said second portion of said photophoric probe comprises an enzyme capable of participating activating or catalyzing a chemiluminescent chemical reaction, resulting in the production of light.

26. The method according to claim 22, wherein said second portion of said photophoric probe comprises aequorin or obelin.

27. The method according to claim 22, wherein said second portion of said photophoric probe comprises an enzyme selected from a peroxidase, a phosphatase, an alkaline-phosphatase, a galactosidase, or a β-glucuronidase.

28. The method according to claim 22, wherein said second portion of said photophoric probe comprises an enzyme capable of catalyzing a chemical reaction for producing a reaction product capable of reacting with a chemical in a chemiluminescent reaction, resulting in the production of light.

29. The method according to claim 17, further comprising treating the detached target cell with a metal dissolving solution for dissolving metal grains attached to said target cell.

30. The method according to claim 29, wherein said photosensitizable metal compound comprises a photosensitizable silver compound, said metal grains are silver metal grains, and wherein said metal dissolving solution is a solution comprising $K_3(Fe(CN)_6)$ and $NH_4SCN$.

31. The method according to claim 17, further comprising detaching from said substrate a living cell attached to said substrate.

32. The method according to claim 31, further comprising collecting said living cell.

33. The method according to claim 32, further comprising washing said living cell to remove most of said developing solution.

34. The method according to claim 17, further comprising the step of detaching from said substrate at least one of said labeled target cells adhered to said substrate.

35. The method according to claim 34, further comprising collecting the detached target cells.

36. The method according to claim 34, wherein detaching comprises applying a detaching agent to said substrate.

37. The method according to claim 36, wherein said detaching agent is n-hexane or a solution comprising an enzyme capable of detaching the target cell attached to said substrate.

38. The method according to claim 37, wherein said enzyme is a proteolytic enzyme.

39. The method according to claim 38, wherein said proteolytic enzyme is pepsin, trypsin, papain or a combination thereof.

40. The method according to claim 36, wherein said detaching agent is formulated for dissolving portions of said metal grains.

41. The method according to claim 17, wherein said target cells to be separated or sorted are eukaryotic cells, prokaryotic cells, mammalian cells, non-mammalian cells, viable cells, pathogenic organisms, non-pathogenic organisms, bacterial cells, viruses, nanobacteria, unicellular organisms, or multicellular organisms.

42. A method for physically separating cells, the method comprising:

providing a liquid containing a mixture of different live cells suspended therein, said mixture comprises target cells and non-target cells;

labeling said non-target cells of said mixture with a photophoric probe adapted to label said non-target cells to the exclusion of said target cells to form labeled non-target cells in said mixture, said photophoric probe is capable of being controllably activated to produce localized emission of light in the vicinity of said labeled non-target cells;

providing a light sensitive substrate, said substrate comprises at least one photosensitizable metal compound;

applying said liquid to said light sensitive substrate such that most labeled non-target cells are adjacent to, or in contact with, the surface of said light sensitive substrate;

activating said photophoric probe to produce localized emission of light in the vicinity of said labeled non-target cells, said light photosensitizes portions of said light sensitive substrate to form photosensitized portions;

developing said photosensitized portions to form metal grains from said metal compound, wherein developing comprises applying to said substrate a developing solution formulated to substantially allow said living cells to remain viable after exposure to said developing solution, whereby said labeled non-target cells adhere to said metal grains; and separating said target cells from said non-target cells adhered to said metal grains by collecting the liquid from the substrate.

43. The method according to claim 42, wherein said step of activating comprises using a photoactivation method, a chemical activation method, a thermal activation method or an electrical activation method.

44. The method according to claim 42, wherein said step of activating comprises inducing said photophoric probe to participate in a light-producing chemical reaction.

45. The method according to claim 42, wherein said photosensitizable metal compound comprises a silver halide.

46. The method according to claim 45, wherein said silver halide is silver chloride, silver bromide, silver iodide or a combination thereof.

47. The method according to claim 42, wherein said photophoric probe comprises:
a first affinity probe capable of specifically and selectively binding to said non-target cell or to a second affinity probe bound to said non-target cell; and
a second portion linked to said first affinity probe and capable of being controllably induced to emit light or to cause the emission of light in the vicinity of a non-target cell to which said photophoric probe is bound.

48. The method according to claim 47, wherein said first affinity probe is an antibody or a fragment thereof, a toxin having an affinity for a portion of said non-target cell, an oligonucleotide probe, a protein based affinity probe, a glycoprotein based affinity probe, a hapten or a molecule having an affinity for a portion of said non-target cell.

49. The method according to claim 47, wherein said second portion of said photophoric probe is a chemiluminescent moiety or agent, a fluorescent moiety or agent, an upconverting moiety, particle or agent, an inorganic two photon upconverting anti-stokes phosphor particle, a two photon upconverting dye, a bioluminescent protein, a bioluminescent molecule, a thermoluminescent moiety, agent or particle or an electroluminescent moiety, agent or particle.

50. The method according to claim 47, wherein said second portion of said photophoric probe comprises an enzyme capable of participating, activating or catalyzing a chemiluminescent chemical reaction resulting in the production of light.

51. The method according to claim 47, wherein said second portion of said photophoric probe comprises aequorin or obelin.

52. The method according to claim 47, wherein said second portion of said photophoric probe comprises an enzyme, which is a peroxidase, a phosphatase, an alkaline-phosphatase, a galactosidase or a β-glucuronidase.

53. The method according to claim 47, wherein said second portion of said photophoric probe comprises an enzyme capable of catalyzing a chemical reaction for producing a reaction product capable of reacting with a chemical in a chemiluminescent reaction resulting in the production of light.

54. The method according to claim 42, wherein said step of collecting cells comprises obtaining a mixture of cells having a concentration of said target cells that is higher relative to the concentration of said non-target cells.

55. The method according to claim 42, wherein said target cells are eukaryotic cells, prokaryotic cells, mammalian cells, non-mammalian cells, viable cells, pathogenic organisms, non-pathogenic organisms, bacterial cells, viruses, nanobacteria, unicellular organisms, or multicellular organisms.

* * * * *